(12) United States Patent
Boyle et al.

(10) Patent No.: US 8,716,287 B2
(45) Date of Patent: May 6, 2014

(54) PHARMACEUTICAL COMPOUNDS

(75) Inventors: Robert George Boyle, Cambridge (GB); David Winter Walker, Linton (GB); Richard Justin Boyce, Newmarket (GB)

(73) Assignee: Sentinel Oncology Limited, Cambridge (GB)

( * ) Notice: Subject to any disclaimer, the term of this patent is extended or adjusted under 35 U.S.C. 154(b) by 0 days.

(21) Appl. No.: 13/697,743

(22) PCT Filed: May 12, 2011

(86) PCT No.: PCT/GB2011/000739
§ 371 (c)(1),
(2), (4) Date: Nov. 13, 2012

(87) PCT Pub. No.: WO2011/141716
PCT Pub. Date: Nov. 17, 2011

(65) Prior Publication Data
US 2013/0065900 A1 Mar. 14, 2013

Related U.S. Application Data

(60) Provisional application No. 61/334,306, filed on May 13, 2010.

(30) Foreign Application Priority Data

May 13, 2010 (GB) .................................... 1008005.9

(51) Int. Cl.
*A61K 31/535* (2006.01)
*C07D 241/00* (2006.01)

(52) U.S. Cl.
USPC ................. 514/235.8; 514/255.06; 544/336; 544/120

(58) Field of Classification Search
USPC ............... 514/235.8, 255.06; 544/336, 120
See application file for complete search history.

(56) References Cited

U.S. PATENT DOCUMENTS

| | | | |
|---|---|---|---|
| 7,056,925 B2 | 6/2006 | Li et al. | |
| 7,067,506 B2 * | 6/2006 | Keegan et al. | 514/183 |
| 7,608,618 B2 | 10/2009 | Kesicki et al. | |
| 7,799,782 B2 * | 9/2010 | Munson et al. | 514/234.5 |
| 2003/0069284 A1 | 4/2003 | Keegan et al. | |
| 2004/0034038 A1 | 2/2004 | Li et al. | |
| 2004/0259885 A1 | 12/2004 | Li et al. | |
| 2005/0096324 A1 | 5/2005 | Tao et al. | |
| 2005/0176733 A1 * | 8/2005 | Boyle et al. | 514/255.05 |
| 2005/0215556 A1 | 9/2005 | Lin et al. | |
| 2010/0105683 A1 | 4/2010 | Keegan et al. | |
| 2010/0260868 A1 | 10/2010 | Humphries et al. | |

FOREIGN PATENT DOCUMENTS

| | | |
|---|---|---|
| WO | 02/070494 A1 | 9/2002 |
| WO | 03/101444 A1 | 12/2003 |
| WO | 2004/014876 A1 | 2/2004 |
| WO | 2005/047294 A1 | 5/2005 |
| WO | 2005/072733 A1 | 8/2005 |
| WO | 2006/012308 A1 | 2/2006 |
| WO | 2006/014359 A2 | 2/2006 |
| WO | 2006/021002 A2 | 2/2006 |
| WO | 2006/105262 A1 | 10/2006 |
| WO | 2006/120573 A2 | 11/2006 |
| WO | 2006/131835 A2 | 12/2006 |
| WO | 2007/144579 A1 | 12/2007 |
| WO | 2008/015423 A1 | 2/2008 |
| WO | 2008/059259 A2 | 5/2008 |
| WO | 2008/067027 A2 | 6/2008 |
| WO | 2010/149394 A1 | 12/2010 |

OTHER PUBLICATIONS

International Search Report for International Application No. PCT/GB2011/000739, dated Aug. 1, 2011.
UK Intellectual Property Office combined search and examination report on GB1008005.9, dated Aug. 23, 2010.
Chen et al., Molecular Cancer, 2009, 8, 24.
Blasina et al., Molecular Cancer Therapeutics, 2008: 7(8), 2394-2404.
Ashwell et al., Clin. Cancer Res. 2008; 14(13), 4032-4037.
Ashwell et al., Expert Opin. Investig. Drugs, 2008, 17(9), 1331-1340.
Li et al., Bioorganic & Medicinal Chemistry Letters, 2006, 16, 2293-2298.
Li et al., Bioorganic & Medicinal Chemistry Letters, 2007, 17, 6499-6504.
Tao et al., Bioorganic & Medicinal Chemistry Letters, 2007, 17, 6593-6601.
Chen et al., Int. J. Cancer, 2006, 119, 2784-2794.
Wang et al., J. Med. Chem., 2005, 48, 3118-3121.
Wang et al., J. Med. Chem., 2007, 50, 1514-1527.

(Continued)

*Primary Examiner* — Rei-tsang Shiao
(74) *Attorney, Agent, or Firm* — Heslin Rothenberg Farley & Mesiti P.C.

(57) ABSTRACT

A compound of the formula (I):

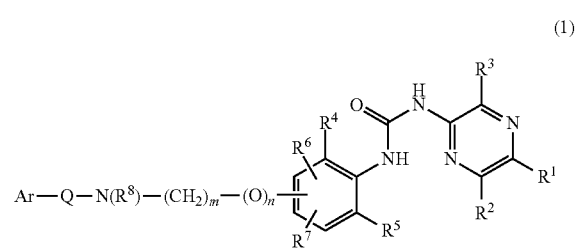

(I)

22 Claims, No Drawings

(56) References Cited

OTHER PUBLICATIONS

Tao et al., Synlett, 2007, 18, 2855-2858.
Tse et al., Clinical Cancer Research, 2007, 13, 1955.
Dai et al., Clinical Cancer Research, 2010, 16, 376.
Hirose et al., Journal of Neurosurgery, 2004, 100, 1060.
Sorensen et al., Nature Cell Biology, 2005, 7, 195.
Mitchell et al., Clinical Cancer Research, 2010, 16, 2076.
McCabe et al., Cancer Research, 2006, 16, 8109.
Dai et al., Blood, 2008, 112, 2439.
Dai et al., Blood, 2005, 105, 1706.
Hahn et al., Molecular Cancer Therapeutics, 2005, 4, 475.
Dai et al., Blood, 2011, 117, 1947.
Bao et al., Nature, 2006, 444, 756.
Yang et al., Biochem. Biophys. Research Commun., 2011, 406, 53.
Cavalier et al., Cancer Research, 2009, 89, 8652.
Pires et al., Cell Cycle, 2010, 9, 2502.

\* cited by examiner

PHARMACEUTICAL COMPOUNDS

CROSS REFERENCE TO RELATED APPLICATIONS

This application is a national stage filing under section 371 of International Application No. PCT/GB2011/000739, filed on May 12, 2011, and published in English on Nov. 17, 2011 as WO 2011/141716, and claims priority to British Application No. 1008005.9, filed on May 13, 2010, and to U.S. Provisional Application No. 61/334,306, filed on May 13, 2010. The entire disclosures of each of the prior applications are hereby incorporated herein by reference.

This invention relates to compounds that inhibit or modulate the activity of Chk-1 kinase. Also provided are pharmaceutical compositions containing the compounds and the therapeutic uses of the compounds.

BACKGROUND OF THE INVENTION

Chk-1 is a serine/threonine kinase involved in the induction of cell cycle checkpoints in response to DNA damage and replicative stress [*Clin. Can. Res.* 2007; 13(7)]. Cell cycle checkpoints are regulatory pathways that control the order and timing of cell cycle transitions. Most cancer cells have impaired G1 checkpoint activation due to a defective p53 tumor suppressor protein. Hahn et al., "Rules for making human tumor cells" *N. Engl. J. Med.* 2002; 347: 1593-603 and Hollstein et al., "p53 mutations in human cancers" *Science* 1991; 253: 49-53) have reported that tumours are associated with mutations in the p53 gene, a tumour suppressor gene found in about 50% of all human cancers Chk-1 inhibition abrogates the intra S and G2/M checkpoints and has been shown to selectively sensitise tumour cells to well known DNA damaging agents. Examples of DNA damaging agents where this sensitising effect has been demonstrated include Gemcitabine, Pemetrexed, Cytarabine, Irinotecan, Camptothecin, Cisplatin, Carboplatin [*Clin. Cancer Res.* 2010, 16, 376], Temozolomide [*Journal of Neurosurgery* 2004, 100, 1060], Doxorubicin [*Bioorg. Med. Chem. Lett.* 2006; 16:421-6], Paclitaxel [WO2010149394] Hydroxy urea [*Nat. Cell. Biol.* 2005 February; 7(2):195-20] and ionising radiation [*Clin. Cancer Res.* 2010, 16, 2076].

Recently published data have also shown that Chk-1 inhibitors may act synergistically with PARP inhibitors [*Cancer Res.;* 66: (16)], Mek inhibitors [*Blood.* 2008 Sep. 15; 112(6): 2439-2449], Farnesyltransferase inhibitors [*Blood.* 2005 Feb. 15; 105(4):1706-16], Rapamycin [*Mol. Cancer Ther.* 2005 March; 4(3):457-70] and Src inhibitors [*Blood.* 2011 Feb. 10; 117(6):1947-57].

Resistance to chemotherapy and radiotherapy, a clinical problem for conventional therapy, has been associated with activation of the DNA damage response in which Chk-1 has been implicated (Chk-1 activation is associated with radioresistance in glioblastoma [*Nature;* 2006; 444(7):756-760] and the inhibition of Chk-1 sensitises lung cancer brain metastases to radiotherapy [*Biochem. Biophys. Res. Commun.* 2011 March 4; 406(1):53-8].

It is also envisaged that Chk-1 inhibitors, either as single agents or in combination, may be useful in treating tumour cells in which constitutive activation of DNA damage and checkpoint pathways drive genomic instability. This phenotype is associated with complex karyotypes in samples from patients with acute myeloid leukemia (AML) [*Cancer Research* 2009, 89, 8652]. In vitro antagonisation of the Chk-1 kinase with a small molecule inhibitor or by RNA interference strongly reduces the clonogenic properties of high-DNA damage level AML samples. In contrast Chk-1 inhibition has no effect on normal hematopoietic progenitors. Furthermore, recent studies have shown that the tumour microenvironment drives genetic instability [*Nature;* 2008; (8):180-192] and loss of Chk-1 sensitises cells to hypoxia/reoxygenation [*Cell Cycle;* 2010; 9(13):2502]. In neuroblastoma, a kinome RNA interference screen demonstrated that loss of Chk-1 inhibited the growth of eight neuroblastoma cell lines. Tumour cells deficient in Fanconi anemia DNA repair have shown sensitivity to Chk-1 inhibition [*Molecular Cancer* 2009, 8:24].

Various attempts have been made to develop inhibitors of Chk-1 kinase. For example, WO 03/10444 and WO 2005/072733 (both in the name of Millennium) disclose aryl/heteroaryl urea compounds as Chk-1 kinase inhibitors. US2005/215556 (Abbott) discloses macrocyclic ureas as kinase inhibitors. WO 02/070494, WO2006014359 and WO2006021002 (all in the name of Icos) disclose aryl and heteroaryl ureas as Chk-1 inhibitors.

SUMMARY OF THE INVENTION

The present invention provides compounds having activity as Chk-1 kinase inhibitors.

Accordingly, in a first embodiment (Embodiment 1.0), the invention provides a compound of the formula (1):

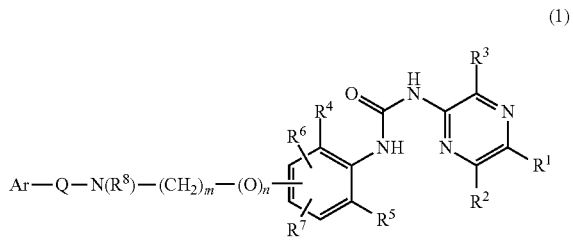

or a salt, N-oxide or tautomer thereof,
wherein $R^1$ is cyano or $C_{1-4}$ alkyl;
$R^2$ is hydrogen or $C_{1-4}$ alkyl;
$R^3$ is hydrogen or $C_{1-4}$ alkyl;
$R^4$ and $R^5$ are the same or different and each is selected from hydrogen, saturated $C_{1-4}$ hydrocarbyl and saturated $C_{1-4}$ hydrocarbyloxy;
$R^6$ and $R^7$ are the same or different and each is selected from hydrogen, halogen, CN, $C_{1-4}$ alkyl and $C_{1-4}$ alkoxy wherein the $C_{1-4}$ alkyl and $C_{1-4}$ alkoxy are each optionally substituted with hydroxy, $C_{1-2}$ alkoxy or by one or more flourine atoms;
$R^8$ is hydrogen or $C_{1-4}$ alkyl;
Q is an alkylene chain of 1 to 4 carbon atoms in length between the moiety Ar and the nitrogen atom N, wherein one or more of the 1 to 4 carbon atoms of the alkylene chain may optionally be substituted with one or two $C_{1-4}$ alkyl groups, or wherein one carbon atom of the 1 to 4 carbon atoms of the alkylene chain may optionally be substituted with a group —$CH_2CH_2$— which together with the said one carbon atom forms a cyclopropyl group;
m is 1, 2, 3 or 4;
n is 0 or 1; and
Ar is a monocyclic or bicyclic aryl or heteroaryl group of 5 to 10 ring members containing 0, 1, 2, 3 or 4 heteroatom ring members selected from O, N and S, the aryl or heteroaryl group being optionally substituted with one to four substituents $R^{13}$ which are the same or different;

R$^{13}$ is selected from:
  halogen;
  cyano;
  nitro;
  a carbocyclic or heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$; and
  a group R$^a$-R$^b$;
R$^a$ is a bond, O, CO, X$^1$C(X$^2$), C(X$^2$)X$^1$, X$^1$C(X$^2$)X$^1$, S, SO, SO$_2$, NR$^c$, SO$_2$NR$^c$ or NR$^c$SO$_2$;
R$^b$ is:
  hydrogen;
    a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$;
    an acyclic C$_{1-12}$ hydrocarbyl group optionally substituted with one or more substituents selected from hydroxy; oxo; halogen; cyano; nitro; carboxy; amino; mono- or di-C$_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$; wherein one or more but not all of the carbon atoms of the acyclic C$_{1-12}$ hydrocarbyl group may optionally be replaced by O, S, SO, SO$_2$, NR$^c$, X$^1$C(X$^2$), C(X$^2$)X$^1$ or X$^1$C(X$^2$)X$^1$;
R$^c$ is:
  hydrogen;
    a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$;
    an acyclic C$_{1-12}$ hydrocarbyl group optionally substituted with one or more substituents selected from hydroxy; oxo; halogen; cyano; nitro; carboxy; amino; mono- or di-C$_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$; wherein one or more but not all of the carbon atoms of the acyclic C$_{1-12}$ hydrocarbyl group may optionally be replaced by O, S, SO, SO$_2$, NH, N—C$_{1-4}$ alkyl, C(O)O, OC(O), NH(CO), C(O)NH, NH(CO)NH, N(C$_{1-4}$alkyl)C(O), C(O)N(C$_{1-4}$ alkyl)
X$^1$ is O, S or NR$^c$; and
X$^2$ is =O, =S or =NR$^c$;
wherein R$^{14}$ is selected from R$^{13}$ provided that when the substituents R$^{14}$ contain a carbocyclic or heterocyclic group, the said carbocyclic or heterocyclic group is unsubstituted or substituted with one or more substituents R$^{15}$; and
R$^{15}$ is selected from R$^{13}$ except that any carbocyclic or heterocyclic groups constituting or forming part of R$^{15}$ may not bear a substituent containing or consisting of a carbocyclic or heterocyclic group;
provided that when m is 1, n is 0 and R$^1$ is cyano.

Particular and preferred compounds of the formula (1) are as defined in the following embodiments:

Embodiment 1.0A

A compound according to Embodiment 1.0 wherein m is 1, 2 or 3.

Embodiment 1.1

A compound according to Embodiment 1.0 having the formula (1)

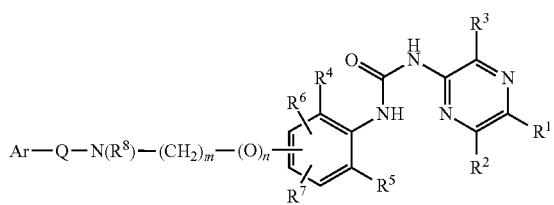

(1)

or a salt, N-oxide or tautomer thereof,
wherein R$^1$ is cyano or C$_{1-4}$ alkyl;
R$^2$ is hydrogen or C$_{1-4}$ alkyl;
R$^3$ is hydrogen or C$_{1-4}$ alkyl;
R$^4$ and R$^5$ are the same or different and each is selected from hydrogen, C$_{1-4}$ alkyl and C$_{1-4}$ alkoxy;
R$^6$ and R$^7$ are the same or different and each is selected from hydrogen, halogen, CN, C$_{1-4}$ alkyl and C$_{1-4}$ alkoxy wherein the C$_{1-4}$ alkyl and C$_{1-4}$ alkoxy are each optionally substituted with hydroxy, C$_{1-2}$ alkoxy or by one or more flourine atoms;
R$^8$ is hydrogen or C$_{1-4}$ alkyl;
Q is an alkylene chain of 1 to 4 carbon atoms in length between the moiety Ar and the nitrogen atom N, wherein one or more of the 1 to 4 carbon atoms of the alkylene chain may optionally be substituted with one or two methyl groups;
m is 1, 2 or 3;
n is 0 or 1; and
Ar is a monocyclic or bicyclic aryl or heteroaryl group of 5 to 10 ring members containing 0, 1, 2, 3 or 4 heteroatom ring members selected from O, N and S, the aryl or heteroaryl group being optionally substituted with one to four substituents R$^{13}$ which are the same or different;
R$^{13}$ is selected from:
  halogen;
  cyano;
  nitro;
  a carbocyclic or heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$; and
  a group R$^a$-R$^b$;
R$^a$ is a bond, O, CO, X$^1$C(X$^2$), C(X$^2$)X$^1$, X$^1$C(X$^2$)X$^1$, S, SO, SO$_2$, NR$^c$, SO$_2$NR$^c$ or NR$^c$SO$_2$;
R$^b$ is:
  hydrogen;
    a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents R$^{14}$;

an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; wherein one or more but not all of the carbon atoms of the acyclic $C_{1-12}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is:
hydrogen;
a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; wherein one or more but not all of the carbon atoms of the acyclic $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$alkyl)C(O), C(O)N($C_{1-4}$ alkyl)

$X^1$ is O, S or $NR^c$; and
$X^2$ is =O, =S or =$NR^c$;
wherein $R^{14}$ is selected from $R^{13}$ provided that when the substituents $R^{14}$ contain a carbocyclic or heterocyclic group, the said carbocyclic or heterocyclic group is unsubstituted or substituted with one or more substituents $R^{15}$; and
$R^{15}$ is selected from $R^{13}$ except that any carbocyclic or heterocyclic groups constituting or forming part of $R^{15}$ may not bear a substituent containing or consisting of a carbocyclic or heterocyclic group;
provided that when m is 1, n is 0 and $R^1$ is cyano.

Embodiment 1.2

A compound according to any one of Embodiments 1.0 to 1.1 wherein Ar is an optionally substituted monocyclic aryl or heteroaryl group.

Embodiment 1.3

A compound according to Embodiment 1.2 wherein Ar is selected from optionally substituted phenyl and optionally substituted five and six membered heteroaryl groups containing one, two or three heteroatom ring members selected from O, N and S.

Embodiment 1.4

A compound according to Embodiment 1.3 wherein Ar is optionally substituted phenyl or an optionally substituted five or six membered heteroaryl group selected from pyridine, pyrazine, pyridazine, pyrimidine, triazine, pyrrole, furan, thiophene, imidazole, furazan, oxazole, oxadiazole, oxatriazole, isoxazole, thiazole, isothiazole, pyrazole, triazole and tetrazole.

Embodiment 1.5

A compound according to Embodiment 1.4 wherein Ar is optionally substituted phenyl or an optionally substituted five or six membered heteroaryl group selected from pyridine, pyrazine, pyridazine, pyrimidine, furan, thiophene, imidazole, oxazole, isoxazole, thiazole, isothiazole and pyrazole.

Embodiment 1.6

A compound according to Embodiment 1.5 wherein Ar is selected from phenyl, pyridine, furan and thiophene, each optionally substituted with one or more substituents $R^{13}$ as defined in Embodiment 1.1.

Embodiment 1.7

A compound according to Embodiment 1.6 wherein Ar is optionally substituted phenyl or optionally substituted pyridine.

Embodiment 1.8

A compound according to Embodiment 1.7 wherein Ar is optionally substituted phenyl.

Embodiment 1.9

A compound according to any one Embodiments 1.0 to 1.8 wherein Ar is unsubstituted or is substituted with one to three substituents $R^{13}$.

Embodiment 1.10

A compound according to Embodiment 1.9 wherein Ar is unsubstituted or is substituted with one or two substituents $R^{13}$.

Embodiment 1.11

A compound according to any one of Embodiments 1.0 to 1.10 wherein each $R^{13}$ is independently selected from a group $R^{13a}$ consisting of halogen; cyano; nitro; a monocyclic carbocyclic or heterocyclic group having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$; or a group $R^{a1}$-$R^{b1}$; $R^{a1}$ is a bond, O, CO, $X^{1a}C(X^{2a})$, $C(X^{2a})X^{1a}$, $X^{1a}C(X^{2a})X^{1a}$, S, SO, $SO_2$, $NR^{c1}$, $SO_2NR^{c1}$ or $NR^{c1}SO_2$;
$R^{b1}$ is:
hydrogen;
a carbocyclic and heterocyclic group having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$;
an acyclic $C_{1-8}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and monocyclic carbocyclic and heterocyclic groups having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$; wherein one or more carbon atoms of the acyclic $C_{1-8}$ hydrocarbyl group may optionally be replaced by O, S, SO, $SO_2$, $NR^{c1}$, $X^{1a}C(X^{2a})$, $C(X^{2a})X^{1a}$ or $X^{1a}C(X^{2a})X^{1a}$;

$R^{c1}$ is:
   hydrogen;
   a carbocyclic and heterocyclic group having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$;
   an acyclic $C_{1-8}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$; wherein one or more but not all of the carbon atoms of the $C_{1-8}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$alkyl)C(O), C(O)N($C_{1-4}$alkyl)

$X^{1a}$ is O, S or $NR^{c1}$; and
$X^{2a}$ is =O, =S, or =$NR^{c1}$;
wherein $R^{14a}$ is selected from $R^{13a}$ provided that when the substituents $R^{14a}$ contain a monocyclic carbocyclic or heterocyclic group having from 3 to 10 ring members, the said carbocyclic or heterocyclic group is unsubstituted or substituted with one or more substituents $R^{15a}$; and
$R^{15a}$ is selected from $R^{13a}$ except that any carbocyclic or heterocyclic groups constituting or forming part of $R^{15a}$ may not bear a substituent containing or consisting of a carbocyclic or heterocyclic group.

Embodiment 1.12

A compound according to Embodiment 1.11 wherein each $R^{13a}$ is independently selected from chlorine; fluorine; cyano; a 3 to 8 membered non-aromatic carbocyclic or heterocyclic ring containing 1 or two heteroatom ring members selected from O, N and S and being optionally substituted with one or more substituents $R^{14a}$; a five or six membered aryl or heteroaryl group containing 1, 2 or 3 heteroatom ring members selected from O, N and S and being optionally substituted with one or more substituents $R^{14a}$; and a group $R^{a1}$-$R^{b1}$.

Embodiment 1.13

A compound according to any one of Embodiments 1.0 to 1.12 wherein each $R^{15}$ or $R^{15a}$ does not contain a carbocyclic or heterocyclic group but is otherwise selected from $R^{13}$ or $R^{13a}$ respectively.

Embodiment 1.14

A compound according to any one of Embodiments 1.0 to 1.13 wherein each $R^{14}$ or $R^{14a}$ does not contain a carbocyclic or heterocylic group but is otherwise selected from $R^{14}$ or $R^{14a}$ respectively.

Embodiment 1.15

A compound according to Embodiment 1.11 wherein each $R^{13a}$ is independently selected from:
   halogen;
   a group $R^{a2}$—$C_{1-8}$ acyclic hydrocarbyl;
   a group $R^{a2}$—$C_{1-8}$ acylic hydrocarbyl-$Cy^1$;
   $C_{1-8}$ acyclic hydrocarbyl;
   a group $C_{1-8}$ acyclic hydrocarbyl-$Cy^1$;
   amino;
   carbamoyl;
   cyano;
   a three to eight membered non-aromatic carbocyclic or heterocyclic ring containing up to two heteroatoms selected from O, N and S and being optionally substituted with $C_{1-4}$ alkyl, oxo or $C_{1-4}$alkoxycarbonyl;
   a five or six membered aryl or heteroaryl ring optionally substituted with one or more halogen, $C_{1-4}$ alkyl or $C_{1-4}$ alkoxy groups wherein the $C_{1-4}$ alkyl or $C_{1-4}$ alkoxy groups are each optionally further substituted with one or more fluorine atoms or by hydroxy or $C_{1-2}$ alkoxy;
wherein each acyclic hydrocarbyl moiety is optionally interrupted by an atom or group selected from O, S, S(O), $SO_2$, NH, NMe, $CO_2$, and C(=O) and each acyclic hydrocarbyl moiety is optionally substituted with one or more substituents selected from fluorine, chlorine, hydroxy or $C_{1-2}$ alkoxy;
$R^{a2}$ is a bond, O, CO, $X^{1b}C(X^{2b})$, $C(X^{2b})X^{1b}$, $X^{1b}C(X^{2b})X^{1b}$, S, SO, $SO_2$, $NR^{c2}$, $SO_2NR^{c2}$ or $NR^{c2}SO_2$;
$X^{1b}$ is O, S, NH or NMe; and
$X^2$ is =O, =S, =NH or NMe;
$R^{c2}$ is hydrogen or $C_{1-4}$ hydrocarbyl; and
$Cy^1$ is:
   a three to eight membered non-aromatic carbocyclic or heterocyclic ring containing up to two heteroatoms selected from O, N and S and being optionally substituted with $C_{1-4}$alkyl, $C_{1-4}$ alkoxy, oxo, $C_{1-4}$alkoxycarbonyl; $C_{1-4}$ alkylsulphonyl; wherein the alkyl and alkoxy groups in each case are optionally substituted with one or more substituents selected from fluorine, hydroxy and $C_{1-2}$ alkoxy; or
   a five or six membered aryl or heteroaryl ring optionally substituted with one or more halogen, $C_{1-4}$ alkyl or $C_{1-4}$ alkoxy groups wherein the $C_{1-4}$ alkyl or $C_{1-4}$ alkoxy groups are each optionally further substituted with one or more fluorine atoms or by hydroxy or $C_{1-2}$ alkoxy.

Embodiment 1.15A

A compound according to any one of Embodiments 1.0 to 1.15 wherein $R^c$, $R^{c1}$ and $R^{c2}$ are each selected from hydrogen and $C_{1-4}$ alkyl.

Embodiment 1.16

A compound according to Embodiment 1.11 wherein each $R^{13a}$ is independently selected from:
   fluorine;
   chlorine;
   a group $R^{a3}$—$C_{1-6}$ acyclic hydrocarbyl;
   a group $R^{a3}$—$C_{1-6}$ acyclic hydrocarbyl-$Cy^{1a}$;
   $C_{1-6}$ acyclic hydrocarbyl;
   a group $C_{1-6}$ acyclic hydrocarbyl-$Cy^{1a}$;
   amino;
   carbamoyl;
   cyano;

a three to seven membered non-aromatic carbocyclic or heterocyclic ring containing up to two heteroatoms selected from O, N and S and being optionally substituted with $C_{1-4}$ alkyl, oxo or $C_{1-4}$alkoxycarbonyl;

a five or six membered aryl or heteroaryl ring optionally substituted with one or more halogen, $C_{1-4}$ alkyl or $C_{1-4}$ alkoxy groups wherein the $C_{1-4}$ alkyl or $C_{1-4}$ alkoxy groups are each optionally further substituted with one or more fluorine atoms or by hydroxy or $C_{1-2}$ alkoxy;

wherein each hydrocarbyl moiety is optionally interrupted by an atom or group selected from O, S, S(O), $SO_2$, NH, NMe, $CO_2$, and C(=O) and each hydrocarbyl moiety is optionally substituted with one or more substituents selected from fluorine, chlorine, hydroxy or $C_{1-2}$ alkoxy;

$R^{a3}$ is a bond, O, CO, S, SO, $SO_2$, NH, N—$C_{1-4}$alkyl, C(O)O, OC(O), NH(CO), C(O)NH, NH(CO)NH, N($C_{1-4}$alkyl)C(O), C(O)N($C_{1-4}$alkyl), $SO_2$NH or $NHSO_2$; and $Cy^{1a}$ is:

a three to seven membered non-aromatic carbocyclic or heterocyclic ring containing up to two heteroatoms selected from O, N and S and being optionally substituted with $C_{1-4}$ alkyl, $C_{1-4}$ alkoxy, oxo, $C_{1-4}$ alkoxycarbonyl; $C_{1-4}$ alkylsulphonyl; wherein the alkyl and alkoxy groups in each case are optionally substituted with one or more substituents selected from fluorine, hydroxy and $C_{1-2}$ alkoxy; or a five or six membered aryl or heteroaryl ring optionally substituted with one or more halogen, $C_{1-4}$ alkyl or $C_{1-4}$ alkoxy groups wherein the $C_{1-4}$ alkyl or $C_{1-4}$ alkoxy groups are each optionally further substituted with one or more fluorine Embodiment 1.17

A compound according to Embodiment 1.11 wherein each $R^{13a}$ is independently selected from halogen; $C_{1-8}$ alkyl optionally substituted with one or more fluorine atoms or by hydroxy or $C_{1-2}$ alkoxy; $C_{1-8}$ alkoxy optionally further substituted with one or more fluorine atoms or by hydroxy or $C_{1-2}$ alkoxy; $C_{1-8}$ acylamino; amino; mono-$C_{1-8}$ alkylamino; di-$C_{1-8}$ alkylamino; carbamoyl; $C_{1-8}$ alkylcarbamoyl; di-$C_{1-8}$ alkylcarbamoyl; cyano; $C_{1-8}$ alkoxycarbonyl; a three to eight membered non-aromatic carbocyclic or heterocyclic ring containing up to two heteroatoms selected from O, N and S and being optionally substituted with one or more $C_{1-4}$ alkyl, oxo or $C_{1-4}$ alkoxycarbonyl substituents; a five or six membered aryl or heteroaryl ring optionally substituted with one or more halogen, $C_{1-4}$ alkyl or $C_{1-4}$ alkoxy groups; and where each alkyl or alkoxy group is optionally interrupted by an atom or group selected from O, S, 5(O), $SO_2$, NH, NMe, $CO_2$, and C(=O).

Embodiment 1.17A

A compound according to Embodiment 1.17 wherein the three to eight membered non-aromatic carbocyclic or heterocyclic ring is a morpholinyl, piperidinyl, piperazinyl, homopiperazinyl, N—$C_{1-3}$-alkylpiperazinyl or N—$C_{1-3}$alkylhomopiperazinyl group, each said group being optionally substituted with one to four $C_{1-3}$ alkyl group substituents.

Embodiment 1.17B

A compound according to Embodiment 1.17A wherein Ar is a phenyl group bearing a single substituent which is a piperidinyl, piperazinyl, homopiperazinyl, N—$C_{1-3}$-alkylpiperazinyl or N—$C_{1-3}$alkylhomopiperazinyl group.

Embodiment 1.17C

A compound according to Embodiment 1.17B wherein Ar is a phenyl group bearing a single substituent which is a piperazinyl, homopiperazinyl, N—$C_{1-3}$-alkylpiperazinyl or N—$C_{1-3}$alkylhomopiperazinyl group.

Embodiment 1.17D

A compound according to Embodiment 1.17C wherein Ar is a phenyl group bearing a single substituent which is a piperazinyl or N—$C_{1-3}$-alkylpiperazinyl group.

Embodiment 1.17E

A compound according to Embodiment 1.17C wherein the N—$C_{1-3}$-alkylpiperazinyl group is a 4-methylpiperazinyl group.

Embodiment 1.17F

A compound according to Embodiment 1.17D wherein Ar is a phenyl group bearing a single substituent which is a piperazinyl group.

Embodiment 1.17G

A compound according to any one of Embodiments 1.0 to 1.17A which is other than a compound wherein Ar is a phenyl group bearing a single substituent which is a piperazinyl, homopiperazinyl, N—$C_{1-3}$-alkylpiperazinyl or N—$C_{1-3}$-alkylhomopiprazinyl, piperazinyl group.

Embodiment 1.18

A compound according to Embodiment 1.11 wherein each $R^{13a}$ is independently selected from chlorine, fluorine, $C_{1-4}$ alkyl, $C_{1-4}$ alkoxy, $C_{1-4}$ acylamino, amino, mono-$C_{1-4}$ alkylamino, di-$C_{1-4}$ alkylamino, carbamoyl, $C_{1-4}$ alkylcarbamoyl, di-$C_{1-4}$ alkylcarbamoyl, cyano, $C_{1-4}$ alkoxycarbonyl, morpholinyl, piperidinyl, piperazinyl, N—$C_{1-3}$-alkylpiperazinyl, phenyl, pyridyl, furanyl, thienyl and pyrazolyl, wherein the $C_{1-4}$ alkyl and $C_{1-4}$ alkoxy substituents are each optionally further substituted with one or more fluorine atoms or by hydroxy or $C_{1-2}$ alkoxy, and wherein the phenyl, pyridyl, furanyl, thienyl and pyrazolyl substituents are each optionally further substituted with one or more halogen, $C_{1-4}$ alkyl or $C_{1-4}$ alkoxy groups.

Embodiment 1.18A

A compound according to Embodiment 1.11 wherein each $R^{13a}$ is independently selected from chlorine, fluorine, $C_{1-4}$ alkyl, $C_{1-4}$ alkoxy, $C_{1-4}$ acylamino, amino, mono-$C_{1-4}$ alkylamino, di-$C_{1-4}$ alkylamino, carbamoyl, $C_{1-4}$ alkylcarbamoyl, di-$C_{1-4}$ alkylcarbamoyl, cyano, $C_{1-4}$ alkoxycarbonyl, morpholinyl, piperidinyl, phenyl, pyridyl, furanyl, thienyl and pyrazolyl, wherein the $C_{1-4}$ alkyl and $C_{1-4}$ alkoxy substituents are each optionally further substituted with one or more fluorine atoms or by hydroxy or $C_{1-2}$ alkoxy, and wherein the phenyl, pyridyl, furanyl, thienyl and pyrazolyl substituents are each optionally further substituted with one or more halogen, $C_{1-4}$ alkyl or $C_{1-4}$ alkoxy groups.

Embodiment 1.18B

A compound according to Embodiment 1.11 wherein each $R^{13a}$ is independently selected from chlorine, fluorine, $C_{1-4}$ alkyl, $C_{1-4}$ alkoxy, $C_{1-4}$ acylamino, amino, mono-$C_{1-4}$ alkylamino, di-$C_{1-4}$ alkylamino, carbamoyl, $C_{1-4}$ alkylcarbamoyl, di-$C_{1-4}$ alkylcarbamoyl, cyano, $C_{1-4}$ alkoxycarbonyl, morpholinyl, piperidinyl, piperazinyl, homopiperazinyl, N—$C_{1-3}$-alkylpiperazinyl, N—$C_{1-3}$-alkylhomopiperazinyl, phenyl, pyridyl, furanyl, thienyl and pyrazolyl, wherein the $C_{1-4}$ alkyl and $C_{1-4}$ alkoxy substituents are each optionally further substituted with one or more fluorine atoms or by hydroxy or $C_{1-2}$ alkoxy, and wherein the phenyl, pyridyl, furanyl, thienyl and pyrazolyl substituents are each optionally further substituted with one or more halogen, $C_{1-4}$ alkyl or $C_{1-4}$ alkoxy groups.

Embodiment 1.19

A compound according to Embodiment 1.11 wherein each $R^{13a}$ is independently selected from chlorine, fluorine, cyano, $C_{1-4}$ alkyl and $C_{1-4}$ alkoxy wherein the $C_{1-4}$ alkyl and $C_{1-4}$ alkoxy are each optionally substituted with one or more fluorine atoms.

Embodiment 1.20

A compound according to Embodiment 1.19 wherein Ar is unsubstituted or bears one or two substituents $R^{13a}$ independently selected from chlorine, fluorine, cyano, methyl, methoxy, trifluoromethyl, difluoromethyl, trifluoromethoxy and difluoromethoxy.

Embodiment 1.20A

A compound according to Embodiment 1.20 wherein Ar is unsubstituted or bears one or two substituents $R^{13a}$ independently selected from fluorine and methoxy.

Embodiment 1.21

A compound according to Embodiment 1.20 wherein Ar is unsubstituted or bears one or two fluorine atom substituents.

Embodiment 1.21A

A compound according to Embodiment 1.21 wherein Ar bears a single fluorine atom substituent.

Embodiment 1.21B

A compound according to Embodiment 1.21 wherein Ar is unsubstituted or bears one or two methoxy substituents.

Embodiment 1.21B

A compound according to Embodiment 1.21B wherein Ar bears a single methoxy substituent.

Embodiment 1.22

A compound according to any one of Embodiments 1.1 to 1.21 wherein $R^1$ is cyano or methyl.

Embodiment 1.23

A compound according to Embodiment 1.22 wherein $R^1$ is cyano.

Embodiment 1.24

A compound according to Embodiment 1.22 wherein $R^1$ is methyl.

Embodiment 1.25

A compound according to any one of Embodiments 1.0 to 1.24 wherein $R^2$ is hydrogen or methyl.

Embodiment 1.26

A compound according to Embodiment 1.25 wherein $R^2$ is hydrogen.

Embodiment 1.27

A compound according to any one of Embodiments 1.0 to 1.26 wherein $R^3$ is hydrogen or methyl.

Embodiment 1.28

A compound according to Embodiment 1.27 wherein $R^3$ is hydrogen.

Embodiment 1.29

A compound according to any one of Embodiments 1.0 to 1.28 wherein $R^4$ is selected from hydrogen, methyl and methoxy.

Embodiment 1.30

A compound according to Embodiment 1.29 wherein $R^4$ is hydrogen or methoxy.

Embodiment 1.31

A compound according to Embodiment 1.30 wherein $R^4$ is hydrogen.

Embodiment 1.31A

A compound according to any one of Embodiments 1.0 to 1.28 wherein $R^4$ is selected from saturated $C_{1-4}$ hydrocarbyl and saturated $C_{1-4}$ hydrocarbyloxy.

Embodiment 1.31B

A compound according to Embodiment 1.31A wherein $R^4$ is saturated $C_{1-4}$ hydrocarbyl.

Embodiment 1.31C

A compound according to Embodiment 1.31B wherein the saturated $C_{1-4}$ hydrocarbyl is selected from methyl, ethyl, propyl, isopropyl and cyclopropyl.

Embodiment 1.31D

A compound according to Embodiment 1.31C wherein the saturated $C_{1-4}$ hydrocarbyl is selected from methyl, ethyl and isopropyl.

Embodiment 1.31E

A compound according to Embodiment 1.31A wherein $R^4$ is saturated $C_{1-4}$ hydrocarbyloxy.

Embodiment 1.31F

A compound according to Embodiment 1.31E wherein the saturated $C_{1-4}$ hydrocarbyloxy is selected from methoxy, ethoxy, propoxy, isopropoxy and cyclopropyloxy.

Embodiment 1.31G

A compound according to Embodiment 1.31F wherein the saturated $C_{1-4}$ hydrocarbyloxy is selected from methoxy, ethoxy and isopropyloxy.

Embodiment 1.32

A compound according to any one of Embodiments 1.0 to 1.31 wherein $R^5$ is selected from hydrogen, methyl and methoxy.

Embodiment 1.33

A compound according to Embodiment 1.32 wherein $R^5$ is hydrogen or methoxy.

Embodiment 1.34

A compound according to Embodiment 1.33 wherein $R^5$ is hydrogen.

Embodiment 1.34A

A compound according to any one of Embodiments 1.0 to 1.31G wherein $R^5$ is selected from saturated $C_{1-4}$ hydrocarbyl and saturated $C_{1-4}$ hydrocarbyloxy.

Embodiment 1.34B

A compound according to Embodiment 1.34A wherein $R^5$ is saturated $C_{1-4}$ hydrocarbyl.

Embodiment 1.34C

A compound according to Embodiment 1.34B wherein the saturated $C_{1-4}$ hydrocarbyl is selected from methyl, ethyl, propyl, isopropyl and cyclopropyl.

Embodiment 1.34D

A compound according to Embodiment 1.34C wherein the saturated $C_{1-4}$ hydrocarbyl is selected from methyl, ethyl and isopropyl.

Embodiment 1.34E

A compound according to Embodiment 1.34A wherein $R^5$ is saturated $C_{1-4}$ hydrocarbyloxy.

Embodiment 1.34F

A compound according to Embodiment 1.34E wherein the saturated $C_{1-4}$ hydrocarbyloxy is selected from methoxy, ethoxy, propoxy, isopropoxy and cyclopropyloxy.

Embodiment 1.34G

A compound according to Embodiment 1.34F wherein the saturated $C_{1-4}$ hydrocarbyloxy is selected from methoxy, ethoxy and isopropyloxy.

Embodiment 1.35

A compound according to any one of Embodiments 1.0 to 1.34 wherein $R^6$ is selected from hydrogen, halogen, CN, $C_{1-2}$ alkyl and $C_{1-2}$ alkoxy wherein the $C_{1-2}$ alkyl and $C_{1-2}$ alkoxy are each optionally substituted with hydroxy, $C_{1-2}$ alkoxy or by one or more flourine atoms.

Embodiment 1.36

A compound according to Embodiment 1.35 wherein $R^6$ is selected from hydrogen, chlorine, fluorine, CN, methyl and methoxy wherein the methyl and methoxy groups are each optionally substituted with two or three flourine atoms.

Embodiment 1.37

A compound according to Embodiment 1.36 wherein $R^6$ is hydrogen or chlorine.

Embodiment 1.38

A compound according to Embodiment 1.37 wherein $R^6$ is hydrogen.

Embodiment 1.39

A compound according to Embodiment 1.37 wherein $R^6$ is chlorine.

Embodiment 1.40

A compound according to any one of Embodiments 1.0 to 1.39 wherein $R^7$ is selected from hydrogen, halogen, CN, $C_{1-2}$ alkyl and $C_{1-2}$ alkoxy wherein the $C_{1-2}$ alkyl and $C_{1-2}$ alkoxy are each optionally substituted with hydroxy, $C_{1-2}$ alkoxy or by one or more flourine atoms.

Embodiment 1.41

A compound according to Embodiment 1.40 wherein $R^7$ is selected from hydrogen, chlorine, fluorine, CN, methyl and methoxy wherein the methyl and methoxy groups are each optionally substituted with two or three flourine atoms.

Embodiment 1.42

A compound according to Embodiment 1.41 wherein $R^7$ is hydrogen or chlorine.

Embodiment 1.43

A compound according to Embodiment 1.42 wherein $R^7$ is hydrogen.

Embodiment 1.44

A compound according to Embodiment 1.42 wherein $R^7$ is chlorine.

Embodiment 1.45

A compound according to any one of Embodiments 1.0 to 1.44 wherein $R^6$ is located at a position on the benzene ring meta with respect to the ureido group.

Embodiment 1.46

A compound according to any one of Embodiments 1.0 to 1.45 wherein $R^7$ is located at a position on the benzene ring meta with respect to the ureido group.

Embodiment 1.47

A compound according to any one of Embodiments 1.0 to 1.46 wherein n is 0.

Embodiment 1.48

A compound according to any one of Embodiments 1.0 to 1.46 wherein n is 1.

Embodiment 1.49

A compound according to any one of Embodiments 1.0 to 1.48 wherein m is 2.

Embodiment 1.50

A compound according to any one of Embodiments 1.0 to 1.48 wherein m is 3.

Embodiment 1.50A

A compound according to any one of Embodiments 1.0 to 1.48 wherein m is 4.

Embodiment 1.50B

A compound according to any one of Embodiments 1.0 to 1.48 wherein m is 2, 3 or 4.

Embodiment 1.50C

A compound according to any one of Embodiments 1.0 to 1.48 wherein m is 2 or 3.

Embodiment 1.51

A compound according to any one of Embodiments 1.0 to 1.508 wherein the alkylene chain Q is 1 to 3 carbon atoms in length.

Embodiment 1.52

A compound according to Embodiment 1.51 wherein the alkylene chain Q is 1 or 2 carbon atoms in length.

Embodiment 1.53

A compound according to Embodiment 1.52 wherein the alkylene chain Q is 1 carbon atom in length.

Embodiment 1.54

A compound according to Embodiment 1.52 wherein the alkylene chain Q is 2 carbon atoms in length.

Embodiment 1.55

A compound according to Embodiment 1.51 wherein the alkylene chain Q is 3 carbon atoms in length.

Embodiment 1.56

A compound according to any one of Embodiments 1.0 to 1.55 wherein the alkylene chain Q has the formula $-(CH_2)_j-$ where j is 1 to 4.

Embodiment 1.56A

A compound according to Embodiment 1.56 wherein j is 1.

Embodiment 1.56B

A compound according to Embodiment 1.56 wherein j is 2.

Embodiment 1.56C

A compound according to Embodiment 1.56 wherein j is 3.

Embodiment 1.56D

A compound according to Embodiment 1.56 wherein j is 4.

Embodiment 1.57

A compound according to any one of Embodiments 1.0 to 1.55 wherein one or more of the 1-4 carbon atoms in the alkylene chain Q is substituted with one or two methyl groups.

Embodiment 1.57A

A compound according to any one of Embodiments 1.0 and 1.2 to 1.55 wherein one or more of the 1 to 4 carbon atoms of the alkylene chain Q is substituted with one or two $C_{1-4}$ alkyl groups, provided that at least one $C_{2-4}$ alkyl group substituent is present.

Embodiment 1.57B

A compound according to Embodiment 1.57A wherein the $C_{2-4}$ alkyl group is selected from ethyl, propyl and isopropyl.

Embodiment 1.57C

A compound according to Embodiment 1.57B wherein the $C_{2-4}$ alkyl group is selected from ethyl and isopropyl.

Embodiment 1.57D

A compound according to any one of Embodiments 1.0 to 1.57C wherein 0, 1, 2, 3 or 4 $C_{1-4}$ alkyl group substituents are present on the alkylene chain Q.

Embodiment 1.57E

A compound according to Embodiment 1.57D wherein 0, 1 or 2 $C_{1-4}$ alkyl group substituents are present on the alkylene chain Q.

Embodiment 1.57F

A compound according to any one of Embodiments 1.0 and 1.2 to 1.55 wherein one carbon atom of the 1 to 4 carbon atoms of the alkylene chain is substituted with a group $-CH_2CH_2-$ which together with the said one carbon atom forms a cyclopropyl group.

Embodiment 1.58

A compound according to Embodiment 1.57 wherein a single one of the 1-4 carbon atoms in the alkylene chain Q is substituted with one or two methyl groups.

Embodiment 1.59

A compound according to Embodiment 1.58 wherein the alkylene chain Q is represented by —CHMe-.

Embodiment 1.59A

A compound according to Embodiment 1.59 wherein the compound has an R-stereochemical configuration with regard to the group —CHMe-.

Embodiment 1.59B

A compound according to Embodiment 1.59 wherein the compound has an S-stereochemical configuration with regard to the group —CHMe-.

Embodiment 1.60

A compound according to Embodiment 1.58 wherein the alkylene chain Q is represented by —CMe$_2$-.

Embodiment 1.61

A compound according to any one of Embodiments 1.0 to 1.60 wherein $R^8$ is hydrogen or methyl.

Embodiment 1.62

A compound according to Embodiment 1.61 wherein $R^8$ is hydrogen.

Embodiment 1.63

A compound according to Embodiment 1.61 wherein $R^8$ is methyl.

Embodiment 1.64

A compound according to any one of Embodiments 1.0 to 1.19, 1.25 to 1.47 and 1.51 to 1.63 wherein m is 1, n is 0 and $R^1$ is cyano.

Embodiment 1.65

A compound according to any one of Embodiments 1.0 to 1.64 wherein the compound of formula (1) has the formula (2):

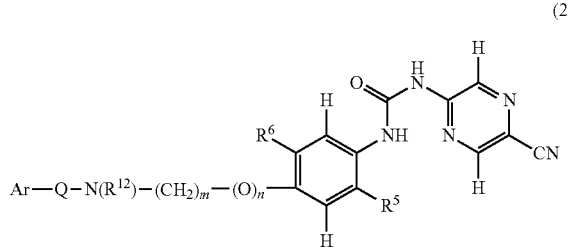

(2)

or a salt, N-oxide or tautomer thereof.

Embodiment 1.65A

A compound according to any one of Embodiments 1.0 to 1.2, 1.9 to 1.17 and 1.22 to 1.64 wherein Ar is selected from:
benzodioxolyl;
unsubstituted phenyl; and
phenyl substituted with one or two substituents selected from halogen; $C_{1-4}$ alkoxy optionally substituted with one or more fluorine atoms; $C_{1-4}$ alkyl optionally substituted with one or more fluorine atoms; and 6-membered saturated heterocyclic rings containing two heteroatoms, one of which is nitrogen and the other of which is selected from nitrogen and oxygen, and wherein the heterocyclic ring is optionally substituted with $C_{1-4}$ alkyl.

Embodiment 1.65B

A compound according to Embodiment 1.65A wherein Ar is selected from benzodioxolyl; unsubstituted phenyl; and phenyl substituted with one or two substituents selected from fluorine, chlorine, methoxy, trifluoromethyl, trifluoromethoxy, morpholinyl, piperazinyl and N-methylpiperazinyl.

Embodiment 1.65C

A compound according to Embodiment 1.65B wherein Ar is selected from unsubstituted phenyl; and phenyl substituted with one or two substituents selected from fluorine, chlorine, methoxy, trifluoromethyl, trifluoromethoxy, morpholinyl, piperazinyl and N-methylpiperazinyl.

Embodiment 1.65D

A compound according to Embodiment 1.65B wherein Ar is selected from unsubstituted phenyl; 2-fluorophenyl; 3-fluorophenyl; 4-fluorophenyl; 2,3-difluorophenyl; 2,4-difluorophenyl; 2,5-difluorophenyl; 2-chlorophenyl; 3-chlorophenyl; 4-chlorophenyl; 2-chlorophenyl; 4-trifluoromethoxyphenyl; 2-methoxyphenyl; 3-methoxyphenyl; 4-methoxphenyl; 4-morpholin-4-ylphenyl; 4-(4-methylpiperazin-4-yl)phenyl; 4-piperazin-1-ylphenyl; and benzo[1,3]dioxol-5-yl.

Embodiment 1.65E

A compound according to Embodiment 1.65B wherein Ar is selected from unsubstituted phenyl; 2-fluorophenyl; 3-fluorophenyl; 4-fluorophenyl; 2,4-difluorophenyl; 4-chlorophenyl; 2-chlorophenyl; 4-trifluoromethoxyphenyl; 2-methoxyphenyl; 3-methoxyphenyl; 4-methoxphenyl; 4-morpholin-4-ylphenyl; 4-(4-methylpiperazin-4-yl)phenyl; 4-piperazin-1-ylphenyl; and benzo[1,3]dioxol-5-yl.

Embodiment 1.66

A compound according to Embodiment 1.65 wherein the compound of formula (2) has the formula (3):

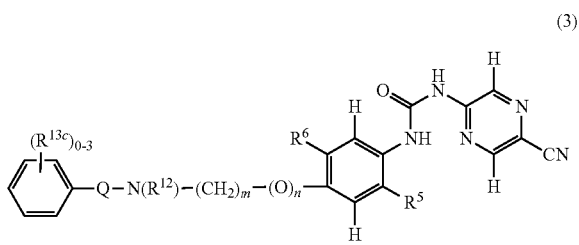

(3)

or a salt, N-oxide or tautomer thereof;

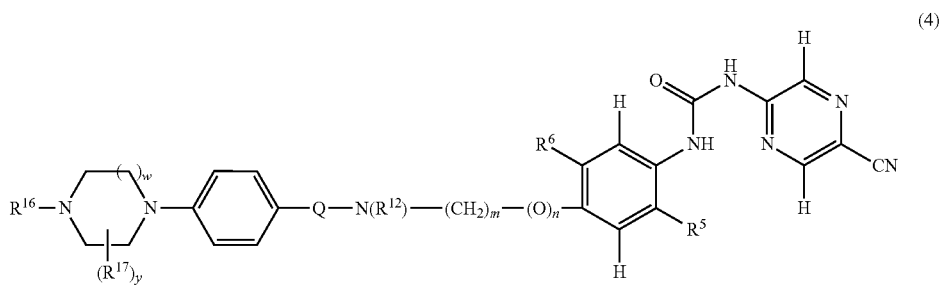

(4)

wherein $R^{13c}$ is a group $R^{13}$ or $R^{13a}$ as defined in any one of the preceding Embodiments.

Embodiment 1.66A

A compound according to Embodiment 1.66 wherein 0, 1 or 2 substituents $R^{13c}$ are present and are selected from halogen; $C_{1-4}$ alkoxy optionally substituted with one or more fluorine atoms; $C_{1-4}$ alkyl optionally substituted with one or more fluorine atoms; and 6-membered saturated heterocyclic rings containing two heteroatoms, one of which is nitrogen and the other of which is selected from nitrogen and oxygen, and wherein the heterocyclic ring is optionally substituted with $C_{1-4}$ alkyl.

Embodiment 1.66B

A compound according to Embodiment 1.66A wherein 0, 1 or 2 substituents $R^{13c}$ are present and are selected from fluorine, chlorine, methoxy, trifluoromethyl, trifluoromethoxy, morpholinyl, piperazinyl and N-methylpiperazinyl.

Embodiment 1.66C

A compound according to Embodiment 1.66B wherein either no substituent $R^{13c}$ is present or one or two substituents $R^{13c}$ are present and are selected from 2-fluoro; 3-fluoro; 4-fluoro; 2,3-difluoro; 2,4-difluoro; 2,5-difluoro; 2-chloro; 3-chloro; 4-chloro; 2-chloro; 4-trifluoromethoxy; 2-methoxy; 3-methoxy; 4-methoxy; 4-morpholin-4-yl; 4-(4-methylpiperazin-4-yl); and 4-piperazin-1-yl.

Embodiment 1.66D

A compound according to Embodiment 1.66C wherein either no substituent $R^{13c}$ is present or one or two substituents $R^{13c}$ are present and are selected from 2-fluoro; 3-fluoro; 4-fluoro; 2,4-difluoro; 4-chloro; 2-chloro; 4-trifluoromethoxy; 2-methoxy; 3-methoxy; 4-methoxy; 4-morpholin-4-yl; 4-(4-methylpiperazin-4-yl); and 4-piperazin-1-yl.

Embodiment 1.66E

A compound according to Embodiment 1.66 wherein the compound of formula (3) has the formula (4):

or a salt, N-oxide or tautomer thereof;
wherein w is 1 or 2; y is 0, 1, 2, 3 or 4; $R^{16}$ is hydrogen or $C_{1-3}$ alkyl; and $R^{17}$ is $C_{1-3}$ alkyl.

Embodiment 1.66F

A compound according to Embodiment 1.66E wherein $R^{16}$ is methyl.

Embodiment 1.66G

A compound according to Embodiment 1.66E wherein $R^{16}$ is hydrogen.

Embodiment 1.66H

A compound according to any one of Embodiments 1.66E to 1.66G wherein $R^{17}$ is methyl.

Embodiment 1.66J

A compound according to any one of Embodiments 1.66E to 1.66H wherein y is 0.

Embodiment 1.66K

A compound according to any one of Embodiments 1.66E to 1.66H wherein y is 1, 2, 3 or 4.

Embodiment 1.66L

A compound according to any one of Embodiments 1.66E to 1.66K wherein w is 1.

Embodiment 1.66M

A compound according to any one of Embodiments 1.66E to 1.66K wherein w is 2.

Embodiment 1.67

A compound according to any one of Embodiments 1.66 to 1.66M wherein $R^5$ is hydrogen or methoxy; $R^6$ is hydrogen or chlorine; n is 0 or 1; m is 1 or 2 provided that when n is 1 then m is 2; $R^{12}$ is hydrogen or methyl; Q is $CH_2$, $CH(CH_3)$ or $CH_2CH_2$; 0-2 moieties $R^{13c}$ are present on the benzene ring and, when present, are selected from chlorine, fluorine, methoxy, trifluoromethyl and trifluoromethoxy.

Embodiment 1.68

A compound according to Embodiment 1.67 wherein $R^5$ is hydrogen or methoxy; $R^6$ is hydrogen or chlorine; n is 0; m is 1 or 2; $R^{12}$ is hydrogen; Q is $CH_2$, $CH(CH_3)$ or $CH_2CH_2$; 0-2 moieties $R^{13c}$ are present on the benzene ring and, when present, are selected from chlorine, fluorine and methoxy.

Embodiment 1.69

A compound according to Embodiment 1.68 wherein $R^5$ is methoxy; $R^6$ is hydrogen; n is 0; m is 1 or 2; $R^{12}$ is hydrogen; Q is $CH_2$; 0-1 moieties $R^{13c}$ are present on the benzene ring and, when present, are selected from chlorine, fluorine and methoxy.

Embodiment 1.70

A compound according to Embodiment 1.69 wherein 0-1 moieties $R^{13c}$ are present on the benzene ring and, when present, are selected from fluorine.

Embodiment 1.70A

A compound according to Embodiment 1.69 wherein 0-1 moieties $R^{13c}$ are present on the benzene ring and, when present, are selected from methoxy.

Embodiment 1.71

A compound according to Embodiment 1.0 or Embodiment 1.1 which is selected from the compounds:
1-[4-(2-benzylamino-ethyl)-phenyl]-3-(5-cyano-pyrazin-2-yl)-urea;
1-(5-cyano-pyrazin-2-yl)-3-{4-[2-(4-fluoro-benzylamino)-ethyl]-phenyl}-urea;
1-(5-cyano-pyrazin-2-yl)-3-{4-[2-(2,4-difluoro-benzylamino)-ethyl]-phenyl}-urea;
1-{3-chloro-4-[2-(4-fluoro-benzylamino)-ethyl]-phenyl}-3-(5-cyano-pyrazin-2-yl)-urea;
1-{3-chloro-4-[2-(2,4-difluoro-benzylamino)-ethyl]-phenyl}-3-(5-cyano-pyrazin-2-yl)-urea;
1-{3-chloro-4-[2-(2,4-difluoro-benzylamino)-ethoxy]-phenyl}-3-(5-cyano-pyrazin-2-yl)-urea;
1-(3-chloro-4-(2-(4-fluorophenethylamino)ethyl)phenyl)-3-(5-cyanopyrazin-2-yl)urea;
1-{3-chloro-4-[2-(4-chloro-benzylamino)-ethyl]-phenyl}-3-(5-cyano-pyrazin-2-yl)-urea;
1-{3-chloro-4-[2-(3-fluoro-benzylamino)-ethyl]-phenyl}-3-(5-cyano-pyrazin-2-yl)-urea;
1-{3-chloro-4-[2-(2-chloro-benzylamino)-ethyl]-phenyl}-3-(5-cyano-pyrazin-2-yl)-urea;
1-(3-chloro-4-{2-[(4-fluoro-benzyl)-methyl-amino]-ethyl}-phenyl)-3-(5-cyano-pyrazin-2-yl)-urea;
1-{3-chloro-4-[2-(3-methoxy-benzylamino)-ethyl]-phenyl}-3-(5-cyano-pyrazin-2-yl)-urea;
1-{3-chloro-4-[2-(3-chloro-benzylamino)-ethyl]-phenyl}-3-(5-cyano-pyrazin-2-yl)-urea;
1-{3-chloro-4-[2-(4-trifluoromethoxy-benzylamino)-ethyl]-phenyl}-3-(5-cyano-pyrazin-2-yl)-urea;
1-{3-chloro-4-[2-(4-methoxy-benzylamino)-ethyl]-phenyl}-3-(5-cyano-pyrazin-2-yl)-urea;
1-{3-chloro-4-[2-(2-methoxy-benzylamino)-ethyl]-phenyl}-3-(5-cyano-pyrazin-2-yl)-urea;
1-{3-chloro-4-[2-(4-trifluoromethyl-benzylamino)-ethyl]-phenyl}-3-(5-cyano-pyrazin-2-yl)-urea;
1-(3-chloro-4-{2-[(S)-1-(4-fluoro-phenyl)-ethylamino]ethyl}-phenyl)-3-(5-cyano-pyrazin-2-yl)-urea;
1-[4-(benzylamino-methyl)-2-methoxy-phenyl]-3-(5-cyano-pyrazin-2-yl)-urea;
1-{5-chloro-4-[2-(3-fluoro-benzylamino)-ethyl]-2-methoxy-phenyl}-3-(5-cyano-pyrazin-2-yl)-urea;
1-(5-cyano-pyrazin-2-yl)-3-{4-[2-(4-fluoro-benzylamino)-ethyl]-2-methoxy-phenyl}-urea;
1-(5-cyano-pyrazin-2-yl)-3-{4-[2-(4-fluoro benzylamino)-ethoxy]-2-methoxy-phenyl}-urea;
1-{3-chloro-4-[2-(2-fluoro-benzylamino)-ethyl]-phenyl}-3-(5-cyano-pyrazin-2-yl)-urea;
1-(3-chloro-4-{2-[(R)-1-(4-fluoro-phenyl)-ethylamino]ethyl}-phenyl)-3-(5-cyano-pyrazin-2-yl)-urea;
1-{3-chloro-4-[2-(4-morpholin-4-yl-benzylamino)-ethyl]-phenyl}-3-(5-cyano-pyrazin-2-yl)-urea;
1-{3-chloro-4-[2-(4-fluoro-benzylamino)-ethoxy]-phenyl}-3-(5-cyano-pyrazin-2-yl)-urea;
1-(3-chloro-4-{2-[2-(2,4-difluoro-phenyl)-ethylamino]ethyl}-phenyl)-3-(5-cyano-pyrazin-2-yl)-urea;
1-(3-chloro-4-{2-[(4-fluoro-benzyl)-methyl-amino]-ethyl}-phenyl)-3-(5-cyano-pyrazin-2-yl)-urea;
1-[4-(benzylamino-methyl)-phenyl]-3-(5-cyano-pyrazin-2-yl)-urea;
1-(5-cyano-pyrazin-2-yl)-3-{4-[2-(2,4-difluoro-benzylamino)-ethyl]-2-methoxy-phenyl}-urea;
1-(5-cyano-pyrazin-2-yl)-3-(4-{2-[2-(4-fluoro-phenyl)-ethylamino]ethyl}-2-methoxy-phenyl)-urea;
1-[4-(2-benzylamino-ethyl)-2-methoxy-phenyl]-3-(5-methyl-pyrazin-2-yl)-urea;
1-(5-cyano-pyrazin-2-yl)-3-{4-[2-(2,4-difluoro-benzylamino)-ethoxy]-2-methoxy-phenyl}-urea;
1-(5-Cyano-pyrazin-2-yl)-3-{3-[2-(4-fluoro-benzylamino)-ethyl]-phenyl}-urea;
1-(3-Chloro-4-{2-[4-(4-methyl-piperazin-1-yl)-benzylamino]ethyl}-phenyl)-3-(5-cyano-pyrazin-2-yl)-urea;
1-(5-Cyano-pyrazin-2-yl)-3-{4-[2-(4-fluoro-benzylamino)-ethyl]-3-methyl-phenyl}-urea;
1-{5-Chloro-4-[2-(4-fluoro-benzylamino)-ethyl]-2-methoxy-phenyl}-3-(5-cyano-pyrazin-2-A-urea;
1-(3-Chloro-4-{2-[3-(4-methyl-piperazin-1-yl)-benzylamino]ethyl}-phenyl)-3-(5-cyano-pyrazin-2-yl)-urea;
1-{3-Chloro-4-[2-(3-morpholin-4-yl-benzylamino)-ethyl]-phenyl}-3-(5-cyano-pyrazin-2-yl)-urea;
1-{3-Chloro-4-[2-(3,4-difluoro-benzylamino)-ethyl]-phenyl}-3-(5-cyano-pyrazin-2-yl)-urea;
1-{3-Bromo-4-[2-(4-fluoro-benzylamino)-ethyl]-phenyl}-3-(5-cyano-pyrazin-2-yl)-urea;
1-{5-Bromo-4-[2-(4-fluoro-benzylamino)-ethyl]-2-methoxy-phenyl}-3-(5-cyano-pyrazin-2-A-urea;
1-(5-Cyano-pyrazin-2-yl)-3-(4-{2-[(R)-1-(4-fluoro-phenyl)-ethylamino]ethyl}-2-methoxy-phenyl)-urea;

1-(5-Cyano-pyrazin-2-yl)-3-(4-{2-[(S)-1-(4-fluoro-phenyl)-ethylamino]ethyl}-2-methoxy-phenyl)-urea;
1-{5-Chloro-2-ethoxy-4-[2-(4-fluoro-benzylamino)-ethyl]-phenyl}-3-(5-cyano-pyrazin-2-yl)-urea;
1-{5-Chloro-4-[2-(4-fluoro-benzylamino)-ethyl]-2-isopropoxy-phenyl}-3-(5-cyano-pyrazin-2-yl)-urea;
1-{5-Chloro-4-[2-(4-fluoro-benzylamino)-ethoxy]-2-methoxy-phenyl}-3-(5-cyano-pyrazin-2-A-urea;
1-{5-Chloro-2-methoxy-4-[2-(3-methoxy-benzylamino)-ethyl]-phenyl}-3-(5-cyano-pyrazin-2-yl)-urea;
1-{5-Chloro-2-methoxy-4-[2-(4-methoxy-benzylamino)-ethyl]-phenyl}-3-(5-cyano-pyrazin-2-yl)-urea;
1-(5-Chloro-2-methoxy-4-{2-[4-(4-methyl-piperazin-1-yl)-benzylamino]ethyl}-phenyl)-3-(5-cyano-pyrazin-2-yl)-urea;
1-(5-Cyano-pyrazin-2-yl)-3-(2-methoxy-4-{2-[4-(4-methyl-piperazin-1-yl)-benzylamino]-ethyl}-phenyl)-urea;
1-(5-Chloro-2-methoxy-4-{2-[(S)-1-(4-piperazin-1-yl-phenyl)-ethylamino]ethyl}-phenyl)-3-(5-cyano-pyrazin-2-yl)-urea;
1-(5-Chloro-2-methoxy-4-{2-[(S)-1-(4-methoxy-phenyl)ethylamino]ethyl}-phenyl)-3-(5-cyano-pyrazin-2-yl)-urea;
1-(4-{2-[(Benzo[1,3]-dioxol-5-ylmethyl)-amino]ethyl}-5-chloro-2-methoxy-phenyl)-3-(5-cyano-pyrazin-2-yl)-urea;
1-{5-Chloro-2-methoxy-4-[2-(2-methoxy-benzylamino)-ethyl]-phenyl}-3-(5-cyano-pyrazin-2-yl)-urea;
1-[4-(Benzylamino-methyl)-5-chloro-2-methoxy-phenyl]-3-(5-cyano-pyrazin-2-yl)-urea;
1-(5-Cyano-pyrazin-2-yl)-3-{4-[(4-fluoro-benzylamino)-methyl]-2-methoxy-phenyl}-urea;
1-(5-Cyano-pyrazin-2-yl)-3-{4-[(3-fluoro-benzylamino)-methyl]-2-methoxy-phenyl}-urea;
1-(5-Cyano-pyrazin-2-yl)-3-{4-[(2-fluoro-benzylamino)-methyl]-2-methoxy-phenyl}-urea;
1-(5-Cyano-pyrazin-2-yl)-3-{2-methoxy-4-[(4-methoxy-benzylamino)-methyl]-phenyl}-urea;
1-(5-Cyano-pyrazin-2-yl)-3-{2-methoxy-4-[(3-methoxy-benzylamino)-methyl]-phenyl}-urea;
1-(5-Cyano-pyrazin-2-yl)-3-{2-methoxy-4-[(2-methoxy-benzylamino)-methyl]-phenyl}-urea;
1-{5-Chloro-4-[(4-fluoro-benzylamino)-methyl]-2-methoxy-phenyl}-3-(5-cyano-pyrazin-2-yl)-urea;
1-{5-Chloro-2-methoxy-4-[2-(4-piperazin-1-yl-benzylamino)-ethyl]-phenyl}-3-(5-cyano-pyrazin-2-yl)-urea;
1-(5-Chloro-2-methoxy-4-{2-[(S)-1-(3-methoxy-phenyl)ethylamino]ethyl}-phenyl)-3-(5-cyano-pyrazin-2-yl)-urea and;
and salts and tautomers thereof.

Embodiment 1.72

A compound according to any one of Embodiments 1.0 to 1.71 which is in the form of a salt.

Embodiment 1.73

A compound according to Embodiment 1.72 wherein the salt is an acid addition salt.

Embodiment 1.74

A compound according to claim 1.72 or claim 1.73 wherein the salt is a pharmaceutically acceptable salt.

Embodiment 1.75

A compound according to any one of Embodiments 1.0 to 1.74 having a molecular weight of up to 1000.

Embodiment 1.76

A compound according to Embodiment 1.75 having a molecular weight of less than 750.

Embodiment 1.77

A compound according to Embodiment 1.76 having a molecular weight of less than 700.

Embodiment 1.78

A compound according to Embodiment 1.77 having a molecular weight of less than 650.

Embodiment 1.79

A compound according to Embodiment 1.78 having a molecular weight of less than 600 or less than 550.

Embodiment 1.80

A compound according to Embodiment 1.79 having a molecular weight of less than 525, for example, 500 or less.

Definitions

In this application, the following definitions apply, unless indicated otherwise.

References to "carbocyclic" and "heterocyclic" groups as used herein shall, unless the context indicates otherwise, include both aromatic and non-aromatic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

Heterocyclic groups may have from 1 to 5 heteroatom ring members selected from O, S and N and oxidised forms thereof. More typically, the heterocyclic group may have 1, 2, 3 or 4 heteroatom ring members selected from O, N and S, for example 1, 2 or 3 and more usually 1 or 2 heteroatom ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring.

The term non-aromatic group embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a $C=C$, $C\equiv C$ or $N=C$ bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings. Each ring may contain up to about four heteroatoms typically selected from nitrogen, sulphur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 1, 2 or 3 ring heteroatoms;
  c) a pyrimidine ring fused to a 5- or 6-membered ring containing 1 or 2 ring heteroatoms;
  d) a pyrrole ring fused to a 5- or 6-membered ring containing 1, 2 or 3 ring heteroatoms;
  e) a pyrazole ring fused to a 5- or 6-membered ring containing 1 or 2 ring heteroatoms;
  f) a pyrazine ring fused to a 5- or 6-membered ring containing 1 or 2 ring heteroatoms;
  g) an imidazole ring fused to a 5- or 6-membered ring containing 1 or 2 ring heteroatoms;
  h) an oxazole ring fused to a 5- or 6-membered ring containing 1 or 2 ring heteroatoms;
  i) an isoxazole ring fused to a 5- or 6-membered ring containing 1 or 2 ring heteroatoms;
  j) a thiazole ring fused to a 5- or 6-membered ring containing 1 or 2 ring heteroatoms;
  k) an isothiazole ring fused to a 5- or 6-membered ring containing 1 or 2 ring heteroatoms;
  l) a thiophene ring fused to a 5- or 6-membered ring containing 1, 2 or 3 ring heteroatoms;
  m) a furan ring fused to a 5- or 6-membered ring containing 1, 2 or 3 ring heteroatoms;
  n) a cyclohexyl ring fused to a 5- or 6-membered ring containing 1, 2 or 3 ring heteroatoms; and
  o) a cyclopentyl ring fused to a 5- or 6-membered ring containing 1, 2 or 3 ring heteroatoms.

Examples of bicyclic heteroaryl groups containing a six membered ring fused to a five membered ring include but are not limited to benzfuran, benzthiophene, benzimidazole, benzoxazole, benzisoxazole, benzthiazole, benzisothiazole, isobenzofuran, indole, isoindole, indolizine, indoline, isoindoline, purine (e.g., adenine, guanine), indazole, benzodioxole and pyrazolopyridine groups.

Examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzothiene, dihydrobenzofuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur.

The heterocylic groups can contain, for example, cyclic ether moieties (e.g as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine). Other examples of non-aromatic heterocyclic groups include cyclic amide moieties (e.g. as in pyrrolidone) and cyclic ester moieties (e.g. as in butyrolactone).

Examples of monocyclic non-aromatic heterocyclic groups include 5-, 6- and 7-membered monocyclic heterocyclic groups. Particular examples include morpholine, thiomorpholine and its S-oxide and S,S-dioxide, piperidine (e.g. 1-piperidinyl, 2-piperidinyl, 3-piperidinyl and 4-piperidinyl), N-alkyl piperidines such as N-methyl piperidine, piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine, N-ethyl piperazine and N-isopropylpiperazine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Examples of halogen substituents include fluorine, chlorine, bromine and iodine. Fluorine and chlorine are particularly preferred.

In the definition of the compounds of the formula (1) above and as used hereinafter, the term "hydrocarbyl" is a generic term encompassing aliphatic, alicyclic and aromatic groups having an all-carbon backbone, except where otherwise stated.

In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, can be substituted with one or more substituents as defined herein. The examples and preferences expressed below apply to each of the hydrocarbyl substituent groups or hydrocarbyl-containing substituent groups referred to in the various definitions of substituents for compounds of the formula (1) unless the context indicates otherwise.

The term "acyclic hydrocarbyl" refers generically to acyclic groups which are either saturated (i.e. alkyl groups) or are unsaturated (i.e. groups containing double and triple bonds or mixtures thereof). Examples of acyclic hydrocarbyl groups are alkyl, alkenyl and alkynyl groups.

Generally by way of example, the hydrocarbyl groups can have up to twelve carbon atoms, unless the context requires otherwise. Within the sub-set of hydrocarbyl groups having 1 to 12 carbon atoms, particular examples are $C_{1-8}$ hydrocarbyl groups, $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

An acyclic $C_{1-12}$ hydrocarbyl group may be linear or branched and may contain 0, 1, 2, 3 or 4 multiple (i.e. double or triple) bonds.

Typically, the acyclic $C_{1-12}$ hydrocarbyl group contains 0, 1 or 2 multiple bonds.

In one subset of acyclic $C_{1-12}$ hydrocarbyl groups, there are no multiple bonds (i.e. the acyclic $C_{1-12}$ hydrocarbyl groups are alkyl groups).

In another subset of acyclic $C_{1-12}$ hydrocarbyl groups, there are 1 or 2 multiple bonds.

This subset encompasses $C_{2-12}$ alkenyl groups, $C_{2-12}$ alkynyl groups and $C_{2-12}$ alkenyl-alkynyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-8}$ alkyl groups, such as $C_{1-4}$ alkyl groups (e.g. $C_{1-3}$ alkyl groups or $C_{1-2}$ alkyl groups).

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Where a hydrocarbyl group is not limited to "acyclic hydrocarbyl", it may cover acyclic hydrocarbyl groups as defined above and also hydrocarbyl groups that consist of or contain a cyclic hydrocarbon moiety such as a cycloalkyl or cycloalkenyl group or an aryl group such as a benzene ring.

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of carbocyclic aryl groups include substituted and unsubstituted phenyl, naphthyl, indane and indene groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

The term "non-aromatic hydrocarbyl group" as used herein refers to hydrocarbon groups which are either acyclic (as described above) or consist of or contain one or more non-aromatic cyclic groups such as cycloalkyl or cycloalkenyl. Examples of non-aromatic hydrocarbyl groups include alkyl, alkenyl, alkynyl, cycloalkyl, cycloalkenyl, cycloalkylalkyl, cycloalkenylalkyl, alkylcycloalkyl, alkylcycloalkenyl, cycloalkylalkenyl, cycloalkylalkynyl, alkylcycloalkylalkenyl and alkylcycloalkylalkynyl.

It will be understood that the range of groups covered by the terms "hydrocarbyl group" and "non-aromatic hydrocarbyl group" will be limited by the number of carbon atoms present. Thus, the term $C_{1-4}$ hydrocarbyl will cover inter alia methyl, ethyl, propyl, isopropyl, butyl, isobutyl, ter-butyl, vinyl, allyl, butenyl, isobutenyl, butadienyl, ethynyl, propargyl, butynyl, cyclopropyl, methylcyclopropyl, cyclopropylmethyl and cyclopropylmethyl groups.

Where present and where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^cC(S)O$, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, $SC(NR^c)S$, $NR^cC(NR^c)S$, OC(O)$NR^c$, SC(O)$NR^c$, $NR^cC(O)$ $NR^c$, OC(S)$NR^c$, SC(S)$NR^c$, $NR^cC(S)NR^c$, $OC(NR^c)NR^c$, $SC(NR^c)NR^c$, $NR^cC(NR^cNR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted with various substituents as defined herein. For example, the alkoxy groups can be substituted with halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted with, for example, a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted with various groups and atoms as defined herein. Examples of substituted alkyl groups include alkyl groups substituted with one or more halogen atoms such as fluorine and chlorine (particular examples including bromoethyl, chloroethyl, difluoromethyl, 2,2,2-trifluoroethyl and perfluoroalkyl groups such as trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted with a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted with a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted with aryl groups and heteroaryl groups include benzyl, phenethyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Salts

The compounds of the invention may be presented in the form of salts.

The salts (as defined in Embodiments 1.72 to 1.74) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.73) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Geometric Isomers and Tautomers

The compounds of the invention may exist in a number of different geometric isomeric, and tautomeric forms and references to the compounds of formula (1) as defined in Embodiments 1.0 to 1.80 include all such forms. For the avoidance of doubt, where a compound can exist in one of several geometric isomeric or tautomeric forms and only one is specifically described or shown, all others are nevertheless embraced by formula (1) or subgroups, subsets, preferences and examples thereof.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (1) is present as a single optical isomer (e.g. enantiomer or diastereoisomer). In one general embodiment, 99% or more (e.g. substantially all) of the total amount of the compound of the formula (1) may be present as a single optical isomer (e.g. enantiomer or diastereoisomer).

Isotopes

The compounds of the invention as defined in any one of Embodiments 1.0 to 1.80 may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds of the formula (1) as defined in any one of Embodiments 1.0 to 1.80 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Prodrugs

The compounds of the formula (1) as defined in any one of Embodiments 1.0 to 1.80 may be presented in the form of a pro-drug.

By "prodrugs" is meant for example any compound that is converted in vivo into a biologically active compound of the formula (1), as defined in any one of Embodiments 1.0 to 1.80.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Complexes and Clathrates

Also encompassed by formula (1) or subgroups, subsets, preferences and examples thereof are complexes (e.g. inclusion complexes or clathrates with compounds such as cyclodextrins, or complexes with metals) of the compounds.

Biological Activity

The compounds of the formulae (1) and sub-groups thereof are inhibitors of Chk-1 and consequently are expected to be beneficial in combination with various chemotherapeutic agents or radiation for treating a wide spectrum of proliferative disorders. Preferred compounds of the formula (1) are those compounds that have IC$_{50}$ values of less than 1 μM against Chk-1 kinase (e.g. when determined according the assays described herein). More preferred compounds are those that have IC$_{50}$ values of less than 0.1 μM against Chk-1 kinase. Particularly preferred compounds are those that have $IC_{50}$ values of less than 0.01 µM against Chk-1 kinase.

Accordingly, in further embodiments, the invention provides:

Embodiment 2.1

A compound of the formula (1) as defined in any one of Embodiments 1.0 to 1.80 for use in medicine or therapy.

Embodiment 2.2

A compound of the formula (1) as defined in any one of Embodiments 1.0 to 1.80 for use as a Chk-1 kinase inhibitor.

Embodiment 2.3

A compound of the formula (1) for use as defined in Embodiment 2.2 wherein the compound has an $IC_{50}$ values of less than 1 µM against Chk-1 kinase (e.g. when determined according the assays described herein).

Embodiment 2.4

A compound of the formula (1) for use as defined in Embodiment 2.3 wherein the compound has an $IC_{50}$ value of less than 0.1 µM against Chk-1 kinase.

Embodiment 2.5

A compound of the formula (1) for use as defined in Embodiment 2.3 wherein the compound has an $IC_{50}$ value of less than 0.01 µM against Chk-1 kinase.

Embodiment 2.5A

A compound of the formula (1) for use as defined in Embodiment 2.3 wherein the compound has an $IC_{50}$ value of less than 0.001 µM against Chk-1 kinase.

Embodiment 2.6

A compound of the formula (1) as defined in any one of Embodiments 1.0 to 1.80 or 2.3 to 2.6 for use in enhancing a therapeutic effect of radiation therapy or chemotherapy in the treatment of a proliferative disease such as cancer.

Embodiment 2.6A

A compound of the formula (1) as defined in any one of Embodiments 1.0 to 1.80 or 2.3 to 2.6 for use in the treatment of a proliferative disease such as cancer.

Embodiment 2.7

The use of a compound of the formula (1) as defined in any one of Embodiments 1.0 to 1.80 or 2.3 to 2.6 for the manufacture of a medicament for enhancing a therapeutic effect of radiation therapy or chemotherapy in the treatment of a proliferative disease such as cancer.

Embodiment 2.7A

The use of a compound of the formula (1) as defined in any one of Embodiments 1.0 to 1.80 or 2.3 to 2.6 for the manufacture of a medicament for the treatment of a proliferative disease such as cancer.

Embodiment 2.8

A method for the prophylaxis or treatment of a proliferative disease such as cancer, which method comprises administering to a patient in combination with radiotherapy or chemotherapy a compound of the formula (1) as defined in any one of Embodiments 1.0 to 1.80 or 2.3 to 2.6.

Embodiment 2.8A

A method for the prophylaxis or treatment of a proliferative disease such as cancer, which method comprises administering to a patient a compound of the formula (1) as defined in any one of Embodiments 1.0 to 1.80 or 2.3 to 2.6.

Embodiment 2.9

A compound for use, use or method as defined in any one of Embodiments 2.6 to 2.8A wherein the cancer is selected from carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Embodiment 2.10

A compound for use according to Embodiment 2.9 wherein the cancer is selected from breast cancer, colon cancer, lung cancer, ovarian cancer, pancreatic cancer, prostate cancer, glioma, and leukemia.

It is also envisaged that the Chk-1 inhibitors of the invention may be useful in treating tumours in which mutations (e.g. in p53) have led to the G1/S DNA damage checkpoint being lost (see the introductory section of this application). Accordingly in further embodiments, the invention provides:

Embodiment 2.11

A compound of the formula (1) as defined in any one of Embodiments 1.0 to 1.80 or 2.3 to 2.6A for use in the treatment of a patient suffering from a p53 negative or mutated tumour (e.g. a cancer selected from breast cancer, colon cancer, lung cancer, ovarian cancer, pancreatic cancer, prostate cancer, glioma, and leukemia) in combination with radiotherapy or chemotherapy.

Embodiment 2.12

A compound for use according to Embodiment 2.6 or Embodiment 2.9 or Embodiment 2.10 or Embodiment 2.11 wherein, in addition to administration of a compound of the formula (1) as defined in any one of Embodiments 1.0 to 1.80, the treatment comprises administration to a patient of a chemotherapeutic agent selected from etoposide, gemcitabine and SN-38.

Embodiment 2.13

The use of a compound of the formula (1) as defined in any one of Embodiments 1.0 to 1.80 or 2.3 to 2.6A for the manufacture of a medicament for the treatment of a patient suffering from a p53 negative or mutated tumour.

Embodiment 2.14

A method for the treatment of a patient (e.g. a human patient) suffering from a p53 negative or mutated tumour, which method comprises administering to the patient a therapeutically effective amount of a compound of the formula (1) as defined in any one of Embodiments 1.0 to 1.80 or 2.3 to 2.6A.

The Chk-1 inhibitor compounds of the invention may be used in combination with DNA-damaging anti-cancer drugs and/or radiation therapy to treat subjects with multi-drug resistant cancers. A cancer is considered to be resistant to a drug when it resumes a normal rate of tumour growth while undergoing treatment with the drug after the tumour had initially responded to the drug. A tumour is considered to "respond to a drug" when it exhibits a decrease in tumor mass or a decrease in the rate of tumour growth.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.0 to 1.80, which process comprises:

(A) the reaction of a compound of formula (11):

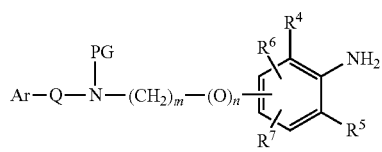

where PG is a protecting group and $R^4$ to $R^{11}$, j, k, m and n are as hereinbefore defined; with a compound of the formula (12):

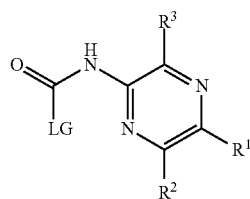

wherein LG is a leaving group such as phenoxy and $R^1$, $R^2$ and $R^3$ are as hereinbefore defined; and thereafter removing the protecting group PG; or (B) the reaction of a compound of the formula (11) with a compound of the formula (13):

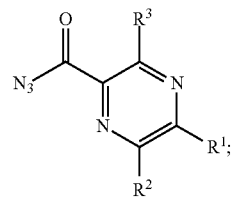

or (C) the reaction of a compound of the formula (11) with a compound of the formula (14):

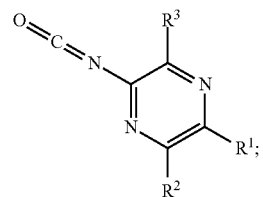

and thereafter optionally converting one compound of the formula (1), into another compound of the formula (1).

The protecting group PG is a group capable of protecting the amino function against unwanted side reactions and examples of such protecting groups are well known to the skilled person, see the reference book (*Protective Groups in Organic Synthesis* (Greene and Wuts) referred to below.

A particularly preferred protecting group PG is the tert-butoxycarbonyl (Boc) group. The Boc group may readily be removed when required by treatment with an acid such as hydrochloric acid or trifluoroacetic acid.

In process variant (A), the leaving group LG can be a halogen such as chlorine or, more preferably, a phenoxy group or substituted phenoxy group such as a para-nitrophenoxy group.

The reaction between a compound of the formula (11) and a compound of the formula (12) where LG is phenoxy is typically carried out with heating (e.g. to a temperature of 80-100° C.) in a polar non-protic solvent such as dimethylformamide.

Compounds of the formula (12) can be prepared by the reaction of a compound of the formula (15):

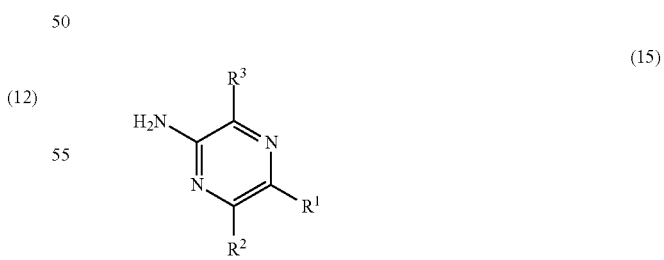

with phenyl chloroformate. The reaction is typically carried out with heating (for example to a temperature of 40-60° C.) in a non-protic solvent such as dichloromethane or tetrahydrofuran or mixtures thereof, in the presence of a non-interfering base such as pyridine.

Compounds of the formula (13) can be prepared from the corresponding carboxylic acid of the formula (13A):

(13A)

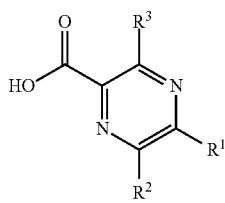

by reaction with diphenylphosphorylazide in a polar non-protic solvent such as tetrahydrofuran (THF) in the presence of a non-interfering base such as triethylamine. The reaction is typically carried out at room temperature.

Alternatively, the azide can be made by forming an acid chloride of the carboxylic acid, and reacting the acid chloride with sodium azide.

Compounds of the formula (14) can be prepared by thermal decomposition of compounds of the formula (13) under Curtius conditions.

Compounds of the formula (11) can be prepared by the reduction of a nitro-compound of the formula (16):

(16)

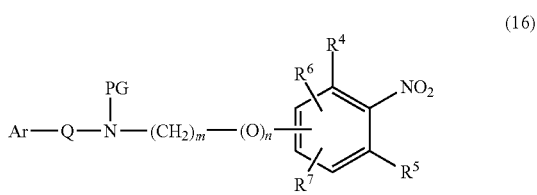

using conditions suitable for reducing a nitro group to an amino group. Reduction of the nitro group can be carried out, for example, using a metal such as zinc powder in the presence of an acid (e.g. a weak acid such as ammonium chloride), or by catalytic hydrogenation over a metal catalyst such as platinum oxide or Raney nickel, or by use of a reducing agent such as an alkali metal dithionite (e.g. sodium dithionite). The skilled person will be well aware of the types of reagents and conditions required for the reduction of the nitro group.

The nitro compounds of the formula (16) can be prepared by various synthetic routes depending on the nature of the elements $R^8$, $R^9$, $R^{10}$, $R^{11}$, j, k, m and n.

For example, compounds wherein n is 0 can be prepared by a reductive amination reaction between a compound of the formula (17):

(17)

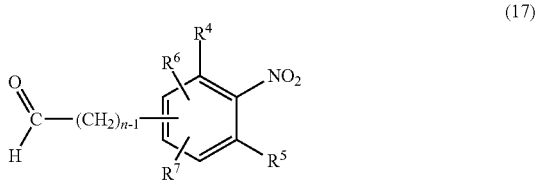

and a compound of the formula (18):

Ar-Q-NH$_2$ (18)

The reductive amination reaction may be carried out using a boron hydride reducing agent such as sodium borohydride or NaB(OAc)$_3$H in accordance with known methods.

Compounds of the formula (17), wherein the aldehyde-containing side chain is attached to the benzene ring at a position para to the nitro group can be prepared by the sequence of reactions shown in Scheme 1 below.

Scheme 1

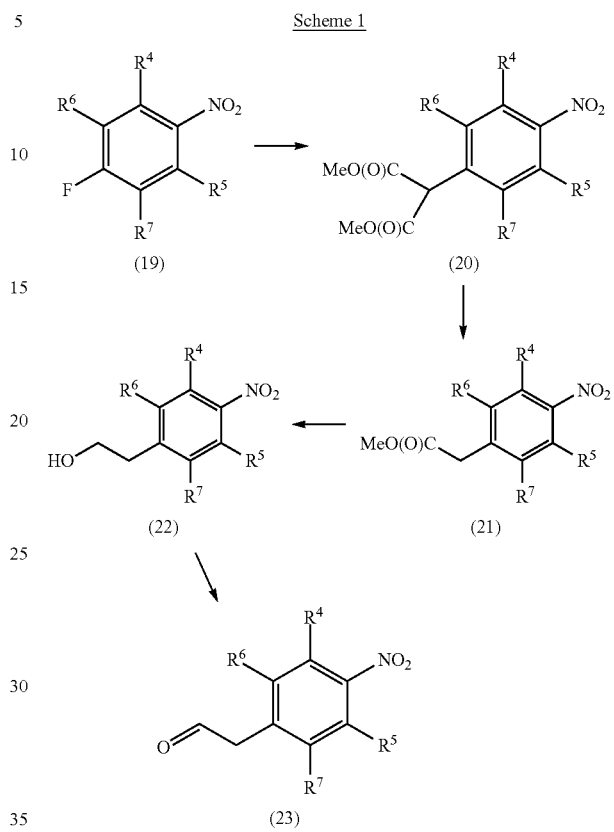

In Scheme 1, the nitro-fluorobenzene (19) is reacted with dimethylmalonate in a polar solvent such as N-methylpyrrolidone in the presence of a base such as sodium hydroxide, usually with heating (for example to a temperature of 70-90° C.), to give the substituted malonic ester (20). The substituted malonic ester (20) may then be subjected to a monohydrolysis/decarboxylation step to give the substituted nitrophenylacetic acid ester (21) by heating in an aqueous DMSO solution containing sodium chloride at a temperature in the range 100-115° C.

The substituted nitrophenylacetic acid ester (21) can be reduced to the alcohol (22) using a boron hydride reagent such as lithium borohydride in a dry polar aprotic solvent such as THF. The alcohol (22) may then be oxidised to the aldehyde (23) using Dess Martin periodinane in a chlorinated solvent such as dichloromethane.

In a variation of the above procedure, the alcohol (22) can be converted to the corresponding bromo compound (24):

(24)

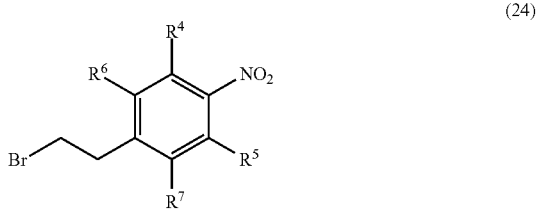

by reaction with PBr₃ in a solvent such as an ether, according to methods well known to the skilled person. Alternatively, the bromo compound (24) can be prepared from the alcohol (22) by reaction with bromine and triphenylphosphine.

The bromo compound (24) can be reacted with the amine (18) to give a compound of formula (16).

Compounds of the formula (16), wherein n is 1 and the oxygen atom is attached to benzene ring at a position para with respect to the nitro group, can be prepared by the reaction of a compound of the formula (25):

(25)

with a compound of the formula (19) (see Scheme 1 for structure of compound (19). The reaction is typically carried out by first reacting the compound of formula (25) with sodium hydride to form an alcoholate anion and then adding the compound of formula (20). The reactions may be conducted in a polar aprotic solvent such as dimethylformamide.

Compounds of formula (19) can be obtained commercially or by using standard synthetic methods well known to the skilled person or analogous thereto, see for example *Advanced Organic Chemistry* by Jerry March, 4th Edition, John Wiley & Sons, 1992, and *Organic Syntheses*, Volumes 1-8, John Wiley, edited by Jeremiah P. Freeman (ISBN: 0-471-31192-8), 1995, and see also the methods described in the experimental section below.

Compounds of the formula (16) wherein $R^8$ and $R^9$ are both hydrogen can be prepared by the reductive amination reaction of an aldehyde compound of the formula (26), where Q' is an alkylene chain of 1 to 3 carbon atoms in length, and an amino compound of the formula (27):

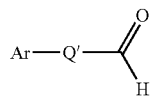

(26)

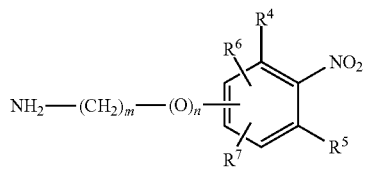

(27)

followed by the reaction of the product with a reagent (such as di-tert-butyl-carbonate) suitable for introducing the protecting group PG. The reductive amination step will typically employ a borohydride reducing agent such as NaB(OAc)₃H as described above.

Compounds of the formula (16) wherein the H₂N—(CH₂)ₘ—(O)ₙ— group is para with respect to the nitro group, n is 0 and m is 2 can be prepared by the reaction of a compound of the formula (28):

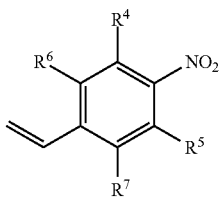

(28)

and a compound of the formula (18) in the presence of hydroquinone (quinol). The reaction may be carried out in an alcoholic solvent such as isopropyl alcohol or n-butanol, typically with heating to a temperature of about 80-90° C.

Compounds of the formula (28) can be prepared by the reaction of a compound of the formula (29):

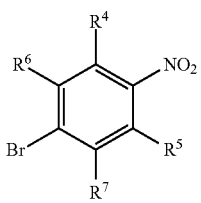

(29)

with potassium ethenyl(trifluoro)borate in the presence of a non-interfering base such as triethylamine and a palladium catalyst such as PdCl₂ (1,1'-bis(diphenylphosphino)-ferrocene).

Compounds of the formula (3) wherein m is 2, n is 0, $R^{12}$ is hydrogen, $R^5$ is methoxy and $R^6$ is chlorine can be prepared by the sequence of reactions shown in Scheme 2 below:

Scheme 2

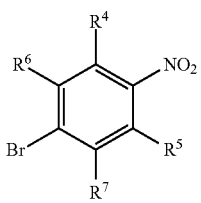

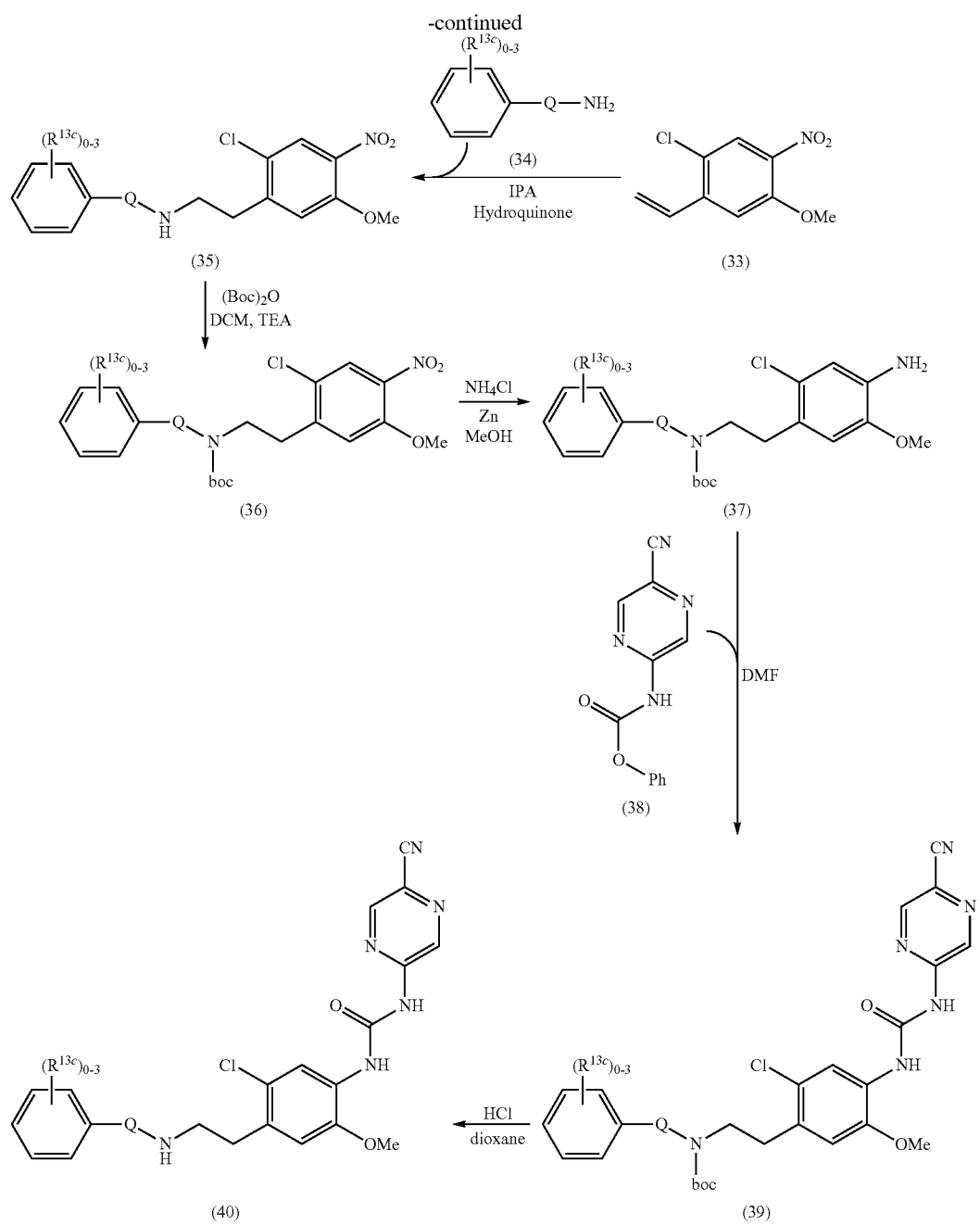

In Scheme 2, the bromo-chloro-fluorobenzene (30) is nitrated by reaction with potassium nitrate in sulphuric acid and the resulting nitro-compound (31) is reacted with sodium methoxide in methanol to give the substituted methoxybenzene (32). The substituted methoxybenzene (32) is then treated with potassium ethenyl(trifluoro)borate in dichloromethane in the presence of triethylamine and the palladium catalyst PdCl$_2$ (1,1'-bis(diphenylphosphino)-ferrocene) to give the vinyl-benzene compound (33). The vinyl-benzene compound (33) is reacted with the phenylalkylamine (34) in the presence of hydroquinone (quinol) in a higher boiling alcohol such as isopropanol or n-butanol at a temperature of about 80-90° C. to give the amine (35). N-Protection of the amine (35) is accomplished using Boc anhydride/triethylamine in dichloromethane to give the N-protected compound (36). The nitro group in the compound (36) is then reduced using zinc and ammonium chloride in methanol to give the amino compound (37). Reaction of the amino compound (37) with the cyanopyrazinyl-carbamic acid ester (38) by heating the reactants together in dimethyl formamide at a temperature of about 80° C. gives the boc-protected compound (39) which is then deprotected using HCl in dioxane to give the product (40).

Once formed, one compound of the formula (1), or a protected derivative thereof, can be converted into another compound of the formula (I) by methods well known to the skilled person. Examples of synthetic procedures for converting one functional group into another functional group are set out in standard texts such as *Advanced Organic Chemistry* and *Organic Syntheses* (see references above) or *Fiesers'*

*Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.0 to 1.80 together with a pharmaceutically acceptable excipient.

The pharmaceutically acceptable excipient can be, for example, a carrier (e.g. a solid, liquid or semi-solid carrier), a diluent or bulking agent, a granulating agent, coating agent, binding agent, disintegrant, lubricating agent, preservative, antioxidant, buffering agent, suspending agent, thickening agent, flavouring agent, sweetener, taste masking agent or any other excipient conventionally used in pharmaceutical compositions. Examples of excipients for various types of pharmaceutical compositions are set out in more detail below.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (1) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; poly-alcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (1) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The compound of formula (1), as defined in any one of Embodiments 1.0 to 1.80, or a prodrug thereof, may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the formula (1) as defined in any one of Embodiments 1.0 to 1.80 as defined herein will be useful either alone or in combination therapy with chemotherapeutic agents (particularly DNA-damaging agents) or radiation therapy in the prophylaxis or treatment of a range of proliferative disease states or conditions. Examples of such disease states and conditions are set out above.

The compounds of formula (1), whether administered alone, or in combination with DNA damaging agents and other anti-cancer agents and therapies, are generally administered to a subject in need of such administration, for example a human or animal patient, preferably a human.

Examples of chemotherapeutic agents that may be co-administered with the compounds of formula (1) as defined in any one of Embodiments 1.0 to 1.80 include:
Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Hypoxia triggered DNA damaging agents (e.g. Tirapazamine)

Particular examples of chemotherapeutic agents that may be administered in combination with the compounds of formula (1) as defined in any one of Embodiments 1.0 to 1.80 include:
nitrogen mustards such as mechlorethamine, cyclophosphamide, ifosfamide, melphalan and chlorambucil;
nitrosoureas such as carmustine, lomustine and semustine;
ethyleneimine/methylmelamine compounds such as triethylenemelamine, triethylene thiophosphoramide and hexamethylmelamine;
alkyl sulphonates such as busulfan;
triazines such as dacarbazine
Antimetabolites such as folates, methotrexate, trimetrexate, 5-fluorouracil, fluorodeoxyuridine, gemcitabine, cytosine arabinoside, 5-azacytidine, 2,2'-difluorodeoxycytidine, 6-mercaptopurine, 6-thioguanine, azathioprine, 2'-deoxycoformycin, erythrohydroxynonyl-adenine, fludarabine phosphate and 2-chlorodeoxyadenosine;
type I topoisomerase inhibitors such as camptothecin, topotecan and irinotecan;
type II topoisomerase inhibitors such as the epipodophylotoxins (e.g. etoposide and teniposide);
antimitotic drugs such as paclitaxel, Taxotere, Vinca alkaloids (e.g. vinblastine, vincristine, vinorelbine) and estramustine (e.g. estramustine phosphate);
antibiotics such as actimomycin D, daunomycin (rubidomycin), doxorubicin (adriamycin), mitoxantrone, idarubicine, bleomycin, mithramycin, mitomycin C and dactinomycin
enzymes such as L-asparaginase;
cytokines and biological response modifiers such as interferon (α, β, γ), interleukin-2G-CSF and GM-CSF:
retinoids such as retinoic acid derivatives (e.g. bexarotene);
radiosensitisers such as metronidazole, misonidazole, desmethylmisonidazole, pimonidazole, etanidazole, nimorazole, nicotinamide, 5-bromodeoxyuridine, 5-iododeoxyuridine and bromodeoxycytidine;
platinum compounds such as cisplatin, carboplatin, spiroplatin, iproplatin, onnaplatin, tetraplatin and oxaliplatin;
anthracenediones such as mitoxantrone;
ureas such as hydroxyurea;
hydrazine derivatives such as N-methylhydrazine and procarbazine;
adrenocortical suppressants such as mitotane and aminoglutethimide;
adrenocorticosteroids and antagonists such as prednisone, dexamethasone and aminoglutethimide;
progestins such as hydroxyprogesterone (e.g. hydroxyprogesterone caproate), medroxyprogesterone (e.g. medroxyprogesterone acetate) and megestrol (e.g. megestrol acetate);
oestrogens such as diethylstilbestrol and ethynyl estradiol;
anti-oestrogens such as tamoxifen;
androgens such as testosterone (e.g. testosterone propionate) and fluoxymesterone;
anti-androgens such as flutamide and leuprolide;
nonsteroidal anti-androgens such as flutamide; and
signal transduction inhibitors such as PARP inhibitors [e.g. as disclosed in *Cancer Res.*; 66: (16)], Mek inhibitors [e.g as disclosed in *Blood.* 2008 Sep. 15; 112(6): 2439-2449], farnesyltransferase inhibitors [e.g. as disclosed in *Blood.* 2005 Feb. 15; 105(4):1706-16], rapamycin and Src inhibitors [e.g as disclosed in *Blood.* 2011 Feb. 10; 117(6):1947-57].

Examples of the chemotherapeutic agents than may be used in combination with the Chk-1 inhibitor compounds of Embodiments 1.0 to 1.80 as defined herein include the chemotherapeutic agents described in Blasina et al., Mol. Cancer Ther., 2008, 7(8), 2394-2404, Ashwell et al., Clin. Cancer Res., 2008, 14(13), 4032-4037, Ashwell et al., Expert Opin. Investig. Drugs, 2008, 17(9), 1331-1340, Trends in Molecular Medicine February 2011, Vol. 17, No. 2 and Clin Cancer Res; 16(2) Jan. 15, 2010.

Particular examples of chemotherapeutic agents that may be used in combination with the Chk-1 inhibitor compounds of Embodiments 1.0 to 1.80 as defined herein include antimetabolites (such as gemcitabine and cytarabine), Topoisomerase-I inhibitors (such as SN38, topotecan, irinotecan), platinum compounds (such as carboplatin and cisplatin), Topoisomerase-II inhibitors (such as doxorubicin and etoposide), thymidylate synthase inhibitors (such as 5-fluoruracil), mitotic inhibitors (such as paclitaxel) and alkylating agents (such as mitomycin C).

A further set of chemotherapeutic agents that may be used in combination with the Chk-1 inhibitor compounds of Embodiments 1.0 to 1.80 as defined herein includes agents that induce stalled replication forks (see Ashwell et al., Clin. Cancer Res., above), and examples of such compounds include gemcitabine, 5-fluorouracil and hydroxyurea.

The compounds of the invention and combinations with chemotherapeutic agents or radiation therapies as described above may be administered over a prolonged term to maintain beneficial therapeutic effects or may be administered for a short period only. Alternatively they may be administered in a pulsatile or continuous manner.

The compounds of the invention will be administered in an effective amount, i.e. an amount which is effective to bring about the desired therapeutic effect either alone (in monotherapy) or in combination with one or more chemotherapeutic agents or radiation therapy. For example, the "effective amount" can be a quantity of compound which, when administered alone or together with a DNA-damaging drug or other anti-cancer drug to a subject suffering from cancer, slows tumour growth, ameliorates the symptoms of the disease and/or increases longevity. More particularly, when used in combination with radiation therapy, with a DNA-damaging drug or other anti-cancer drug, an effective amount of the Chk-1 inhibitor of the invention is the quantity in which a greater response is achieved when the Chk-1 inhibitor is co-administered with the DNA damaging anti-cancer drug and/or radiation therapy compared with when the DNA damaging anti-cancer drug and/or radiation therapy is administered alone. When used as a combination therapy, an "effective amount" of the DNA damaging drug and/or an "effective" radiation dose are administered to the subject, which is a quantity in which anti-cancer effects are normally achieved. The Chk-1 inhibitors of the invention and the DNA damaging anti-cancer drug can be co-administered to the subject as part of the same pharmaceutical composition or, alternatively, as separate pharmaceutical compositions.

When administered as separate pharmaceutical compositions, the Chk-1 inhibitor of the invention and the DNA-damaging anti-cancer drug (and/or radiation therapy) can be administered simultaneously or at different times, provided that the enhancing effect of the Chk-1 inhibitor is retained.

In one embodiment, a compound of any one of Embodiments 1.0 to 1.80 as defined herein is administered before (e.g by up to 8 hours or up to 12 hours or up to one day before) administration of the DNA-damaging anticancer drug.

In another embodiment, a compound of any one of Embodiments 1.0 to 1.80 as defined herein is administered after (e.g by up to 8 hours or up to 12 hours or up to 24 hours or up to 30 hours or up to 48 hours after) administration of the DNA-damaging anticancer drug. In another embodiment, a first dose of a compound of any one of Embodiments 1.0 to 1.80 as defined herein is administered one day after administration of the DNA-damaging anticancer drug and a second dose of the said compound is administered two days after administration of the DNA-damaging anticancer drug.

In a further embodiment, a first dose of a compound of any one of Embodiments 1.0 to 1.80 as defined herein is administered one day after administration of the DNA-damaging anticancer drug, a second dose of the said compound is administered two days after administration of the DNA-damaging anticancer drug, and third dose of the said compound is administered three days after administration of the DNA-damaging anticancer drug.

Particular dosage regimes comprising the administration of a compound of any one of Embodiments 1.0 to 1.80 as defined herein and a DNA-damaging anticancer drug may be as set out in WO2010/118390 (Array Biopharma), the contents of which are incorporated herein by reference.

The amount of Chk-1 inhibitor compound of the invention and (in the case of combination therapy) the DNA damaging anti-cancer drug and radiation dose administered to the subject will depend on the nature and potency of the DNA damaging anti-cancer drug, the type and severity of the disease or condition and on the characteristics of the subject, such as general health, age, sex, body weight and tolerance to drugs. The skilled person will be able to determine appropriate dosages depending on these and other factors. Effective dosages for commonly used anti-cancer drugs and radiation therapy are well known to the skilled person.

A typical daily dose of the compound of formula (1), whether administered on its own in monotherapy or administered in combination with a DNA damaging anticancer drug, can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

Ultimately, however, the quantity of compound administered and the type of composition used will be commensurate with the nature of the disease or physiological condition being treated and will be at the discretion of the physician.

Methods of Diagnosis

Prior to administration of a compound of the formula (1) as defined in any one of Embodiments 1.0 to 1.80, a patient may be screened to determine whether a cancer from which the patient is or may be suffering is one which would be susceptible to treatment with a combination of a chemotherapeutic agent (such as a DNA-damaging agent) and a compound having activity against Chk-1 kinase.

More particularly, a patient may be screened to determine whether a cancer from which the patient is or may be suffering is one which is characterised by a p53 mutation or is a p53 negative cancer.

Cancers which are characterised by p53 mutations or the absence of p53 can be identified, for example, by the methods described in Allred et al., J. Nat. Cancer Institute, Vol. 85, No. 3, 200-206 (1993) and the methods described in the articles listed in the introductory part of this application. For example, p53 protein may be detected by immuno-histochemical methods such as immuno-staining.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

Thus, the compounds of any one of Embodiments 1.0 to 1.80 may be used to treat members of a sub-population of patients who have been screened (for example by testing one or more biological samples taken from the said patients) and have been found to be suffering from a cancer characterised by p53 mutation or a p53 negative cancer.

EXAMPLES

The invention will now be illustrated, but not limited, by reference to the specific embodiments described in the following examples.

In the examples, the following abbreviations are used.
Boc$_2$O di-tert-butyl dicarbonate
DCM dichloromethane
DMF dimethylformamide
DMSO dimethylsulphoxide
EtOAc ethyl acetate
HCl hydrogen chloride
IPA isopropyl alcohol
LiBH$_4$ lithium borohydride
MeOH methanol
Na$_2$SO$_4$ sodium sulfate
NH$_4$Cl ammonium chloride
NMR nuclear magnetic resonance
RT room temperature
TEA triethylamine
TFA trifluoroacetic acid
THF tetrahydrofuran Proton magnetic resonance ($^1$H NMR) spectra were recorded on a Bruker 400 instrument operating at 400 MHz, in DMSO-$d_6$ or MeOH-$d_4$ (as indicated) at 27° C., unless otherwise stated and are reported as follows: chemical shift δ/ppm (multiplicity where s=singlet, d=doublet, t=triplet, q=quartet, m=multiplet, br=broad, number of protons). The residual protic solvent was used as the internal reference.

Liquid chromatography and mass spectroscopy analyses were carried out using the system and operating conditions set out below. Where atoms with different isotopes are present and a single mass quoted, the mass quoted for the compound is the monoisotopic mass (i.e. $^{35}$Cl; $^{79}$Br etc.)

Analytical HPLC/MS Conditions

The LCMS data given in the following examples were obtained using one of Methods B, C, D, E or F below or, where stated, Method A below LCMS Method A Samples were analysed by reverse phase HPLC-MS using a Waters 2795 Alliance HT HPLC, a Micromass ZQ mass spectrometer and a Waters 996 photodiode array UV detector. The LC-MS used electrospray ionisation and one of six different chromatography systems, as follows:

Solvents:
C=1.58 g ammonium formate in 2.5 L water+2.5 mL Ammonia solution
D=2.5 L Acetonitrile+132 mL (5%) solvent C+2.5 mL Ammonia solution
Chromatography:

| Column | Phenomenex Gemini C18, 5 um, 4.6 × 30 mm |
| --- | --- |
| Injection Volume | 5 μL |
| Flow | 2.0 mL/min |
| UV detection | 220 to 400 nm |
| Column Temperature | 35° C. |

| Time (min) | A % | B % | C % | D % |
| --- | --- | --- | --- | --- |
| 0.00 | 0.0 | 0.0 | 95.0 | 5.0 |
| 4.25 | 0.0 | 0.0 | 5.0 | 95.0 |
| 5.80 | 0.0 | 0.0 | 5.0 | 95.0 |
| 5.90 | 0.0 | 0.0 | 95.0 | 5.0 |
| 7.00 | 0.0 | 0.0 | 95.0 | 5.0 |

Mass Spectrometer:

| Ionization mode: | Positive | Negative |
| --- | --- | --- |
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| Interscan delay: | 0.20 seconds | 0.20 seconds |
| Mass range: | 80 to 1000 AMU | 80 to 1000 AMU |

LCMS Method B
Instrument: Shumadzu LCMS 2010 EV
Column: Xbridge $C_{18}$ 250×4.6 mm, 5μ
Wavelength: 266 nm
Flow: 1.0 mL/min
Sample Prep.: 250 ppm in water:Acetonitrile
Mobile Phase: (A) 0.1% TFA in HPLC grade Water
(B) 0.08% TFA in gradient grade methanol

| Time (min) | % A | % B |
| --- | --- | --- |
| 0.01 | 90 | 10 |
| 5.0 | 10 | 90 |
| 8.0 | 0 | 100 |
| 10.0 | 0 | 100 |
| 10.01 | 90 | 10 |
| 12.0 | 90 | 10 |

LCMS Method C

LCMS was carried out using an XBridge $C_{18}$ 150×4.6 mm, 5 micron column at 267 nm. Column flow rate was 1 mL/min and solvents used were 0.1% TFA in HPLC grade water (A) and 0.1% TFA in HPLC grade in acetonitrile (B), with an injection volume of 10 μL. Sample preparation was at 500 ppm in acetonitrile.

| Time (min) | % A | % B |
| --- | --- | --- |
| 0.01 | 90 | 10 |
| 8.00 | 10 | 90 |
| 9.00 | 0 | 100 |
| 12.00 | 0 | 100 |
| 12.01 | 90 | 10 |
| 14.00 | 90 | 10 |

LCMS Method D

LCMS was carried out on an X Bridge $C_{18}$ 150×4.6 mm, 5 micron column at 254 nm. Column flow was 1 mL/min and solvents used were 0.05% $CH_3COONH_4$ in HPLC grade water (A) and 0.05% $CH_3COONH_4$ in HPLC grade methanol (B), with an injection volume of 10 μL.

| Time (min) | % A | % B |
| --- | --- | --- |
| 0.01 | 90 | 10 |
| 5.00 | 10 | 90 |
| 6.00 | 0 | 100 |
| 10.00 | 0 | 100 |
| 10.00 | 90 | 10 |
| 12.00 | 90 | 10 |

LCMS Method E/F

LCMS was carried out using an XBridge C18 50×4.6 mm, 2.5 micron column at 209 nm. Column flow was 1 mL/min and solvents used were 0.1% Ammonium solution in water (A) and 0.1% Ammonium solution in acetonitrile (B), with an injection volume of 30 μL.

| | Method E | | | Method F | |
| --- | --- | --- | --- | --- | --- |
| Time (min) | % A | % B | Time (min) | % A | % B |
| 0.01 | 90 | 10 | 0.01 | 90 | 10 |
| 3.00 | 10 | 90 | 5.00 | 10 | 90 |
| 5.00 | 0 | 100 | 7.00 | 0 | 100 |
| 6.00 | 0 | 100 | 11.00 | 0 | 100 |
| 6.01 | 90 | 10 | 11.01 | 90 | 10 |
| 7.00 | 90 | 10 | 12.00 | 90 | 10 |

Analytical HPLC Conditions

The HPLC data given in the following examples were obtained using one of Methods B, C or D below or, where stated, Method A below HPLC Method A HPLC was carried out on Phenomenex Luna $C_{18}$ 250×4.6 mm, 5 micron at 267 nm. Column flow was 1 mL/min and solvents used were 0.1% TFA in HPLC grade water (A) and 0.1% TFA in Gradient grade methanol (B), with an injection volume of 10 µL. Sample preparation was at 250 ppm in water:methanol.

| Time (min) | % A | % B |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 25.00 | 90 | 10 |

HPLC Method B:

HPLC was carried out on a Waters 600 controller using column X-bridge $C_{18}$ 250×4.6 mm, 5 micron at 267 nm. Column flow was 1 mL/min and solvents used were 0.1% TFA in water (A) and 0.08% TFA in gradient grade acetonitrile (B), with an injection volume of 10 µL. Sample preparation was at 250 ppm in water:methanol.

| Time (min) | % A | % B |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 25.00 | 90 | 10 |

HPLC Method C:

HPLC was carried out on an Agilent-1200 using column X-bridge $C_{18}$ 250×4.6 mm, 5 micron at 267 nm. Column flow was 1 mL/min and solvents used were 0.1% TFA in water (A) and 0.08% TFA in methanol (B), with an injection volume of 10 µL. Sample preparation was at 250 ppm in water:methanol.

| Time (min) | % A | % B |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 25.00 | 90 | 10 |

HPLC Method D:

HPLC was carried out using a Sun fire C18-250*4.6*5u column at 253 nm. Column flow was 1 mL/min and solvents used were 0.1% Formic Acid in water (A) and 0.1% Formic Acid in acetonitrile (B), with an injection volume of 10 µL.

| Time (min) | % A | % B |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 25.00 | 90 | 10 |

Preparative HPLC Conditions

Preparative HPLC Method 1

Instruments: Water 600 controller

Column: Gemini $C_{18}$ 250×19 mm, 5µ

Wavelength: 266 nm

Flow: 21.0 mL/min

Sample Prep.: 30.38 mg/mL in water:Methanol

Mobile Phase: (A) 0.1% TFA in HPLC grade Water
(B) 0.1% TFA in HPLC grade methanol

| Time (min) | % A | % B |
|---|---|---|
| 0.01 | 75 | 25 |
| 5.00 | 45 | 55 |
| 10.00 | 42 | 58 |
| 10.01 | 0 | 100 |
| 12.00 | 0 | 100 |
| 12.01 | 75 | 25 |
| 13.00 | 75 | 25 |

Preparative HPLC Method 2

Instruments: Water 600 controller

Column: Gemini $C_{18}$ 100×21.2 mm, 5µ

Wavelength: 266 nm

Flow: 21.0 mL/min

Sample Prep.: 30.38 mg/mL in water:Methanol

Mobile Phase: (A) 0.1% TFA in HPLC grade Water
(B) 0.1% TFA in HPLC grade acetonitrile

| Time (min) | % A | % B |
|---|---|---|
| 0.01 | 60 | 40 |
| 8.00 | 30 | 70 |
| 8.01 | 60 | 40 |
| 10.00 | 60 | 40 |

Examples 1 to 65

The compounds of Examples 1 to 65 shown in Table 1 below have been prepared. Their NMR, HPLC and LCMS properties and the methods used to prepare them are set out in Table 2.

TABLE 1
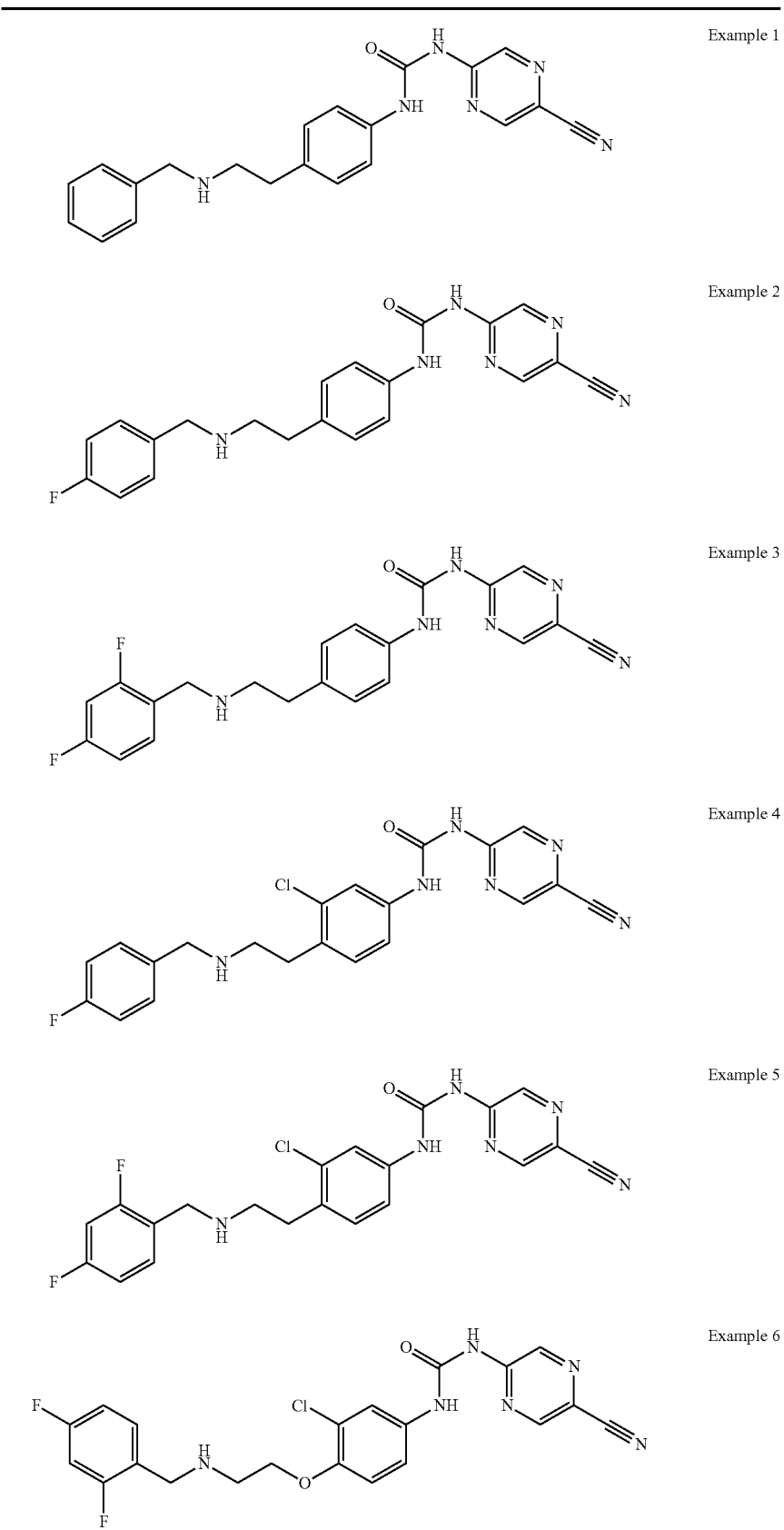
Example 1
Example 2
Example 3
Example 4
Example 5
Example 6

TABLE 1-continued
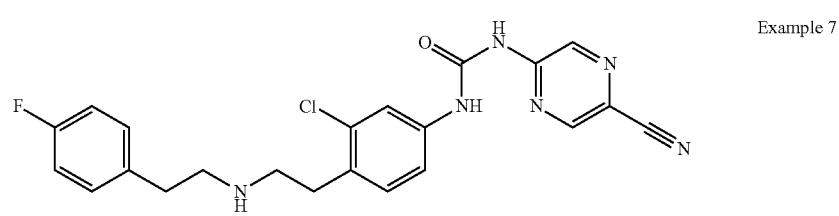
Example 7
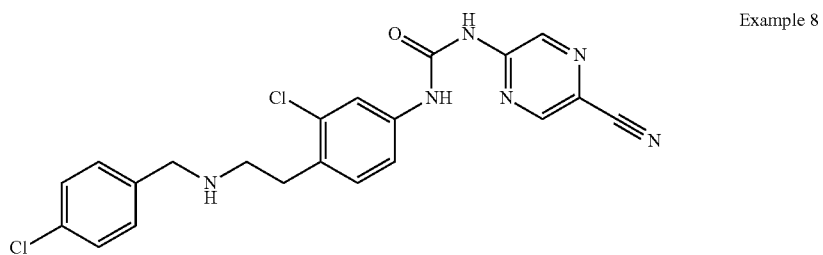
Example 8
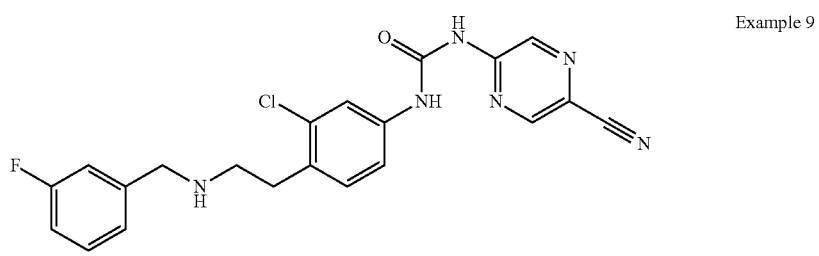
Example 9
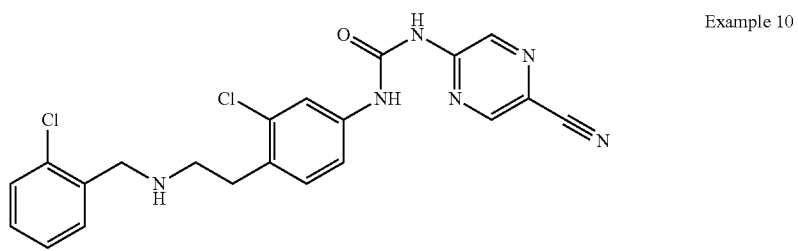
Example 10
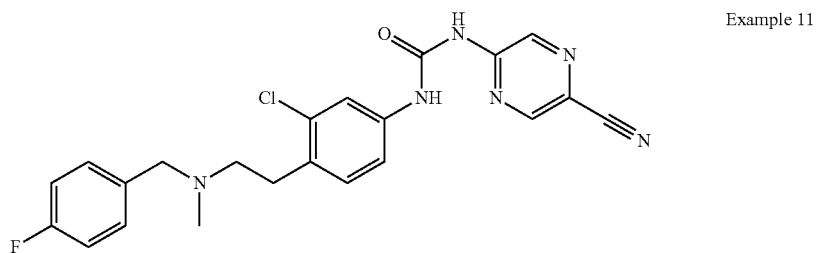
Example 11
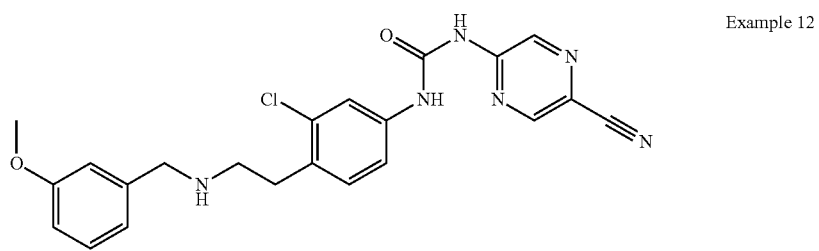
Example 12

TABLE 1-continued
| | |
|---|---|
| 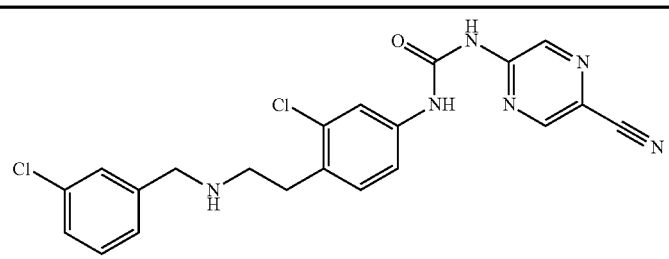 | Example 13 |
| 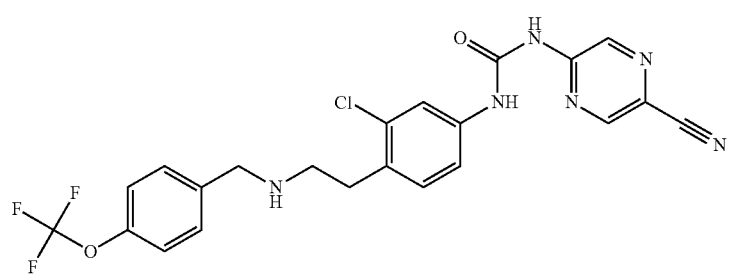 [SMILES: N#Cc1cnc(NC(=O)Nc2ccc(CCNCc3ccc(OC(F)(F)F)cc3)c(Cl)c2)cn1] | Example 14 |
| 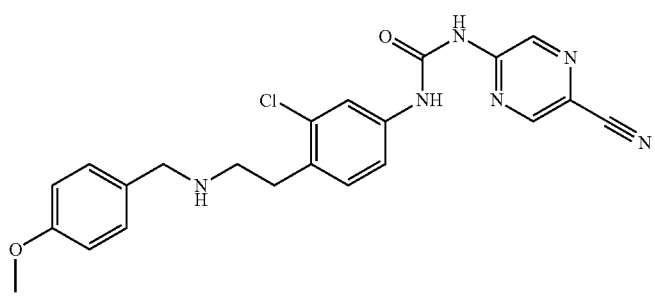 [SMILES: COc1ccc(CNCCc2ccc(NC(=O)Nc3cnc(C#N)cn3)cc2Cl)cc1] | Example 15 |
| 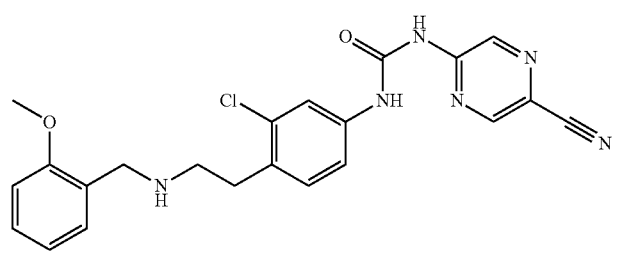 [SMILES: COc1ccccc1CNCCc1ccc(NC(=O)Nc2cnc(C#N)cn2)cc1Cl] | Example 16 |
| 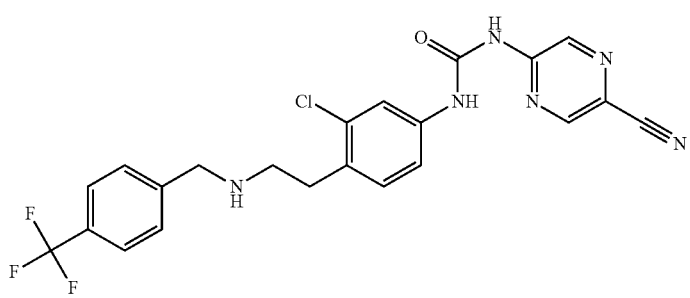 [SMILES: N#Cc1cnc(NC(=O)Nc2ccc(CCNCc3ccc(C(F)(F)F)cc3)c(Cl)c2)cn1] | Example 17 |
| 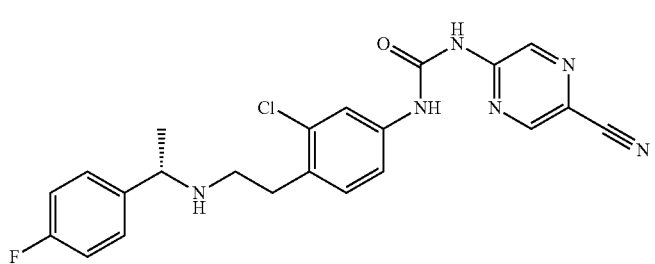 [SMILES: C[C@H](NCCc1ccc(NC(=O)Nc2cnc(C#N)cn2)cc1Cl)c1ccc(F)cc1] | Example 18 |

TABLE 1-continued
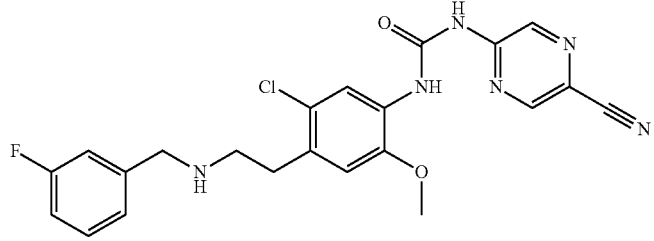 [SMILES: COc1cc(CCNCc2cccc(F)c2)c(Cl)cc1NC(=O)Nc1cnc(C#N)cn1] Example 19
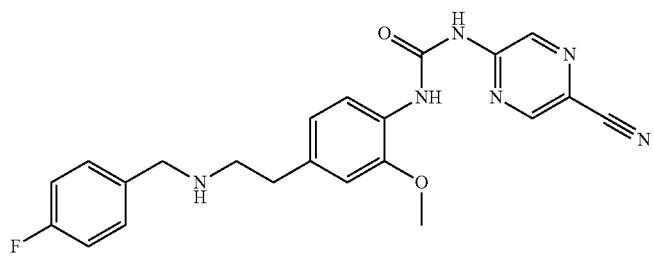 [SMILES: COc1cc(CCNCc2ccc(F)cc2)ccc1NC(=O)Nc1cnc(C#N)cn1] Example 20
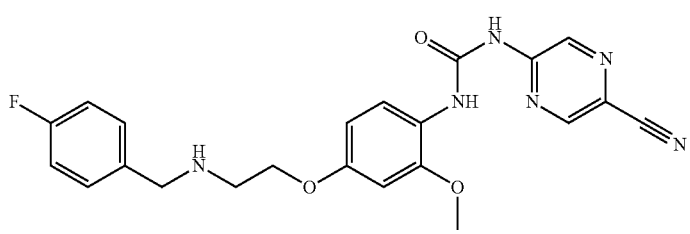 [SMILES: COc1cc(OCCNCc2ccc(F)cc2)ccc1NC(=O)Nc1cnc(C#N)cn1] Example 21
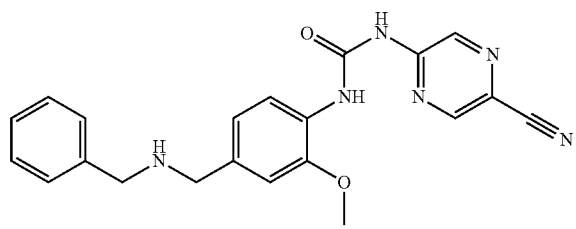 [SMILES: COc1cc(CNCc2ccccc2)ccc1NC(=O)Nc1cnc(C#N)cn1] Example 22
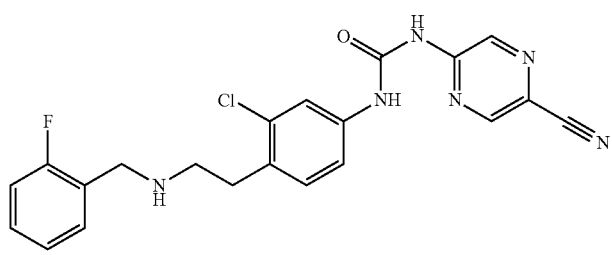 [SMILES: N#Cc1cnc(NC(=O)Nc2ccc(CCNCc3ccccc3F)c(Cl)c2)cn1] Example 23
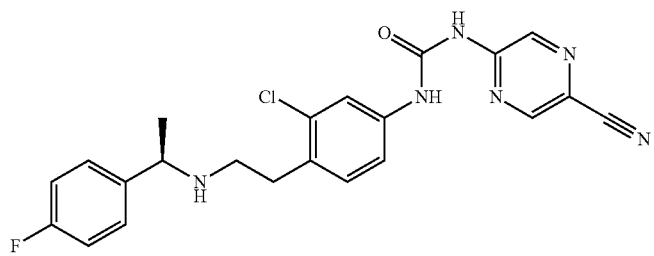 [SMILES: C[C@@H](NCCc1ccc(NC(=O)Nc2cnc(C#N)cn2)cc1Cl)c1ccc(F)cc1] Example 24

TABLE 1-continued
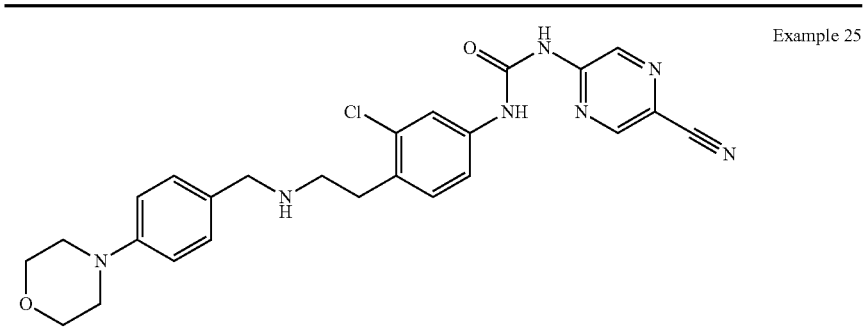
Example 25
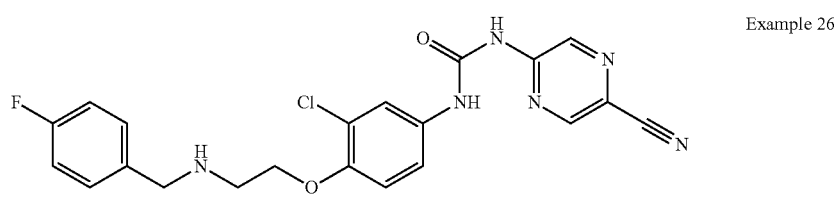
Example 26
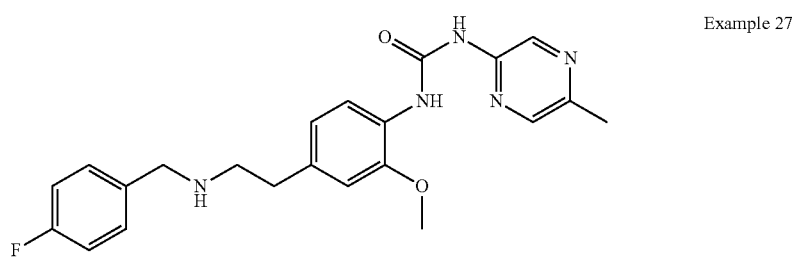
Example 27
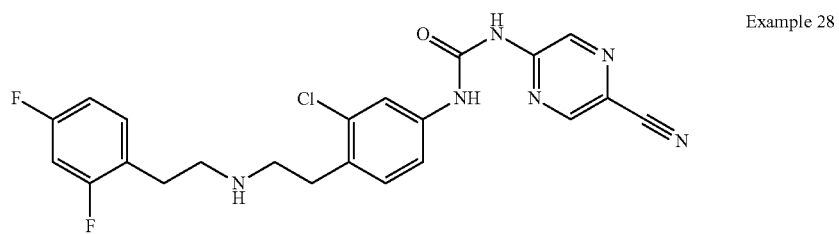
Example 28
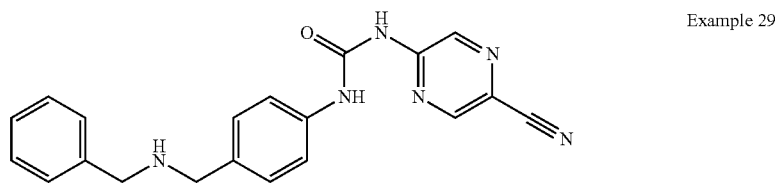
Example 29
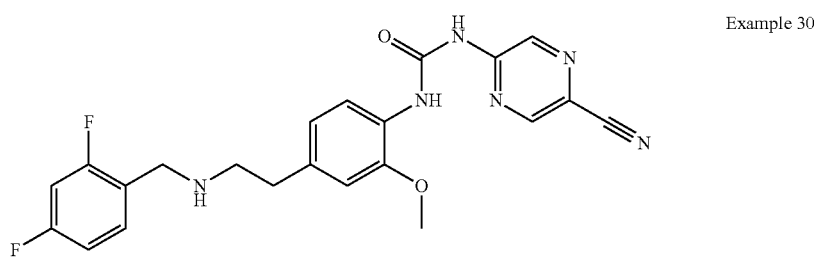
Example 30

TABLE 1-continued
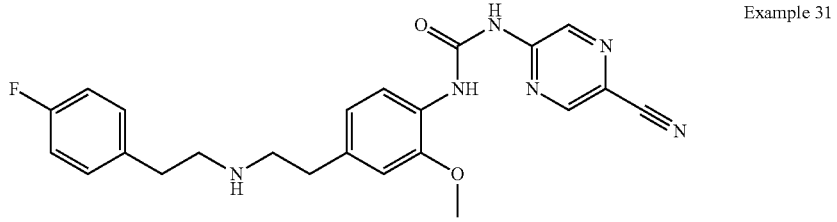
Example 31
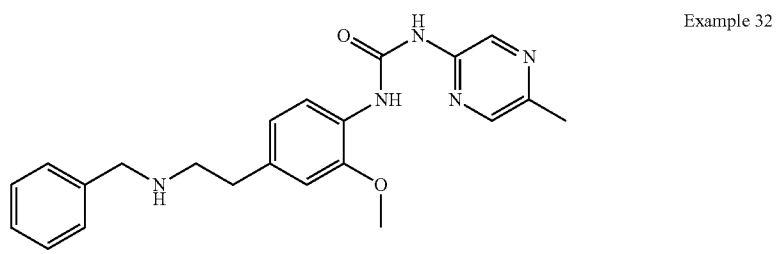
Example 32
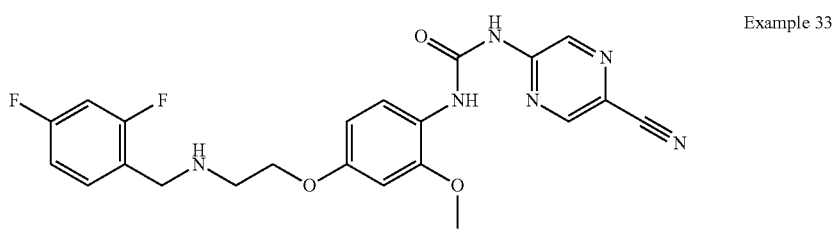
Example 33
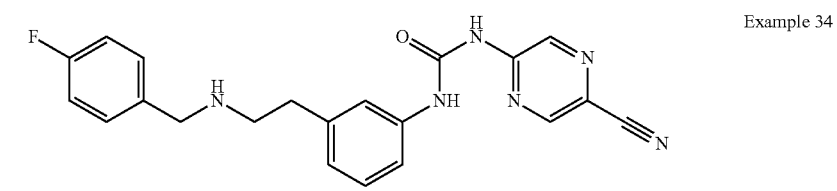
Example 34
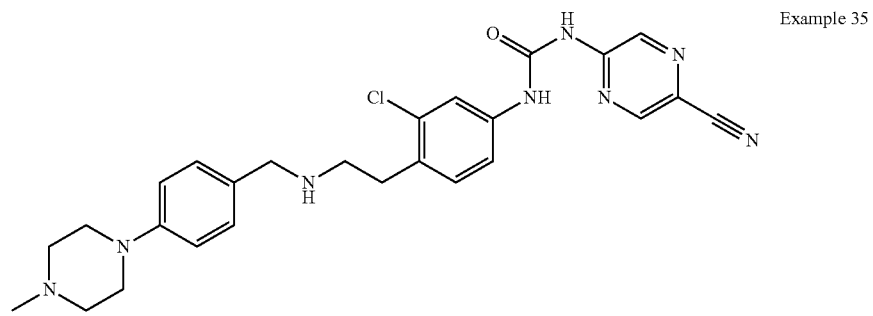
Example 35
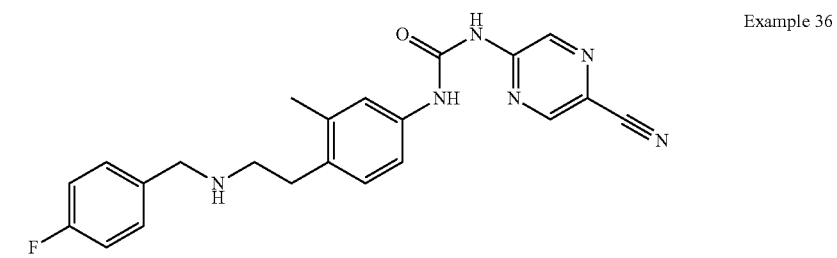
Example 36

TABLE 1-continued
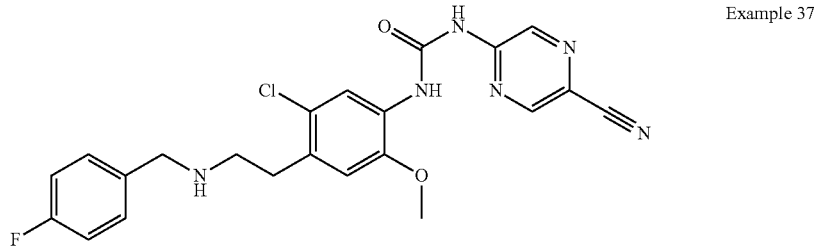
Example 37
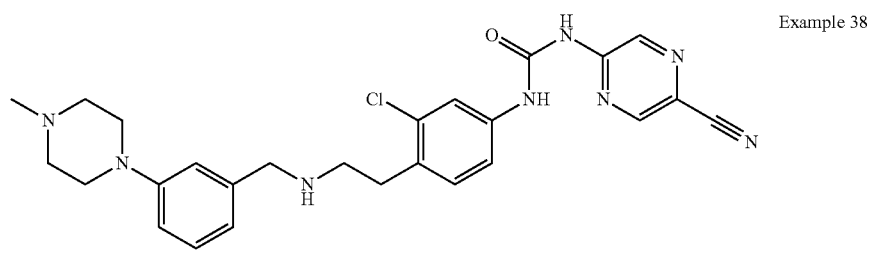
Example 38
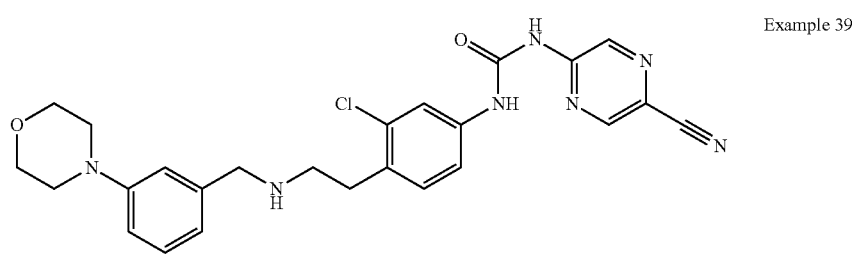
Example 39
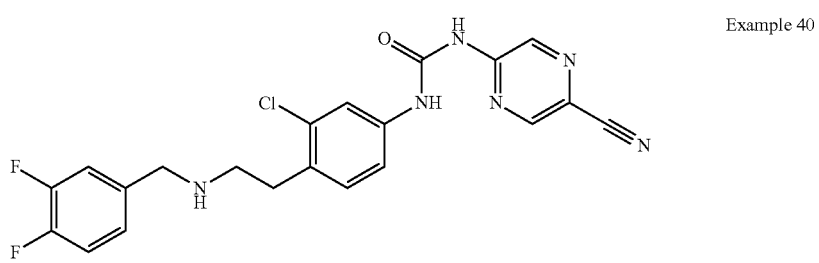
Example 40
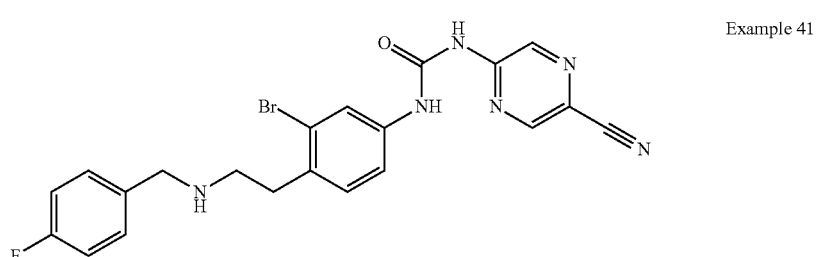
Example 41
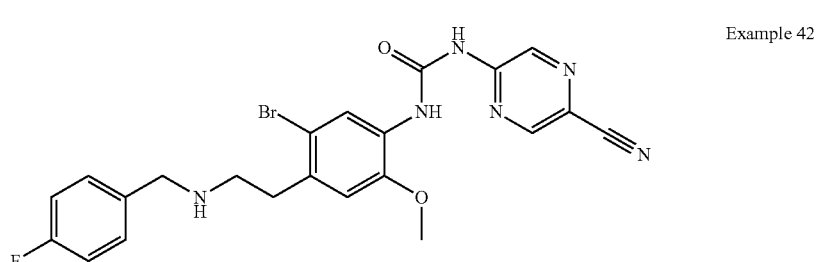
Example 42

TABLE 1-continued
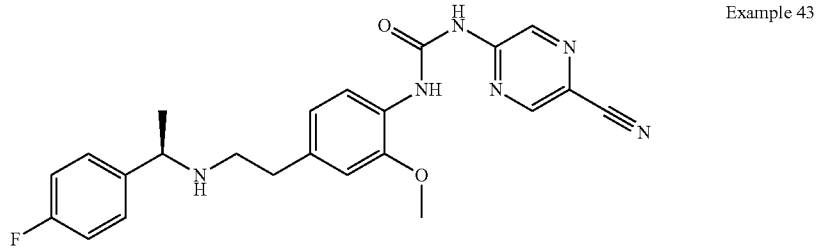
Example 43
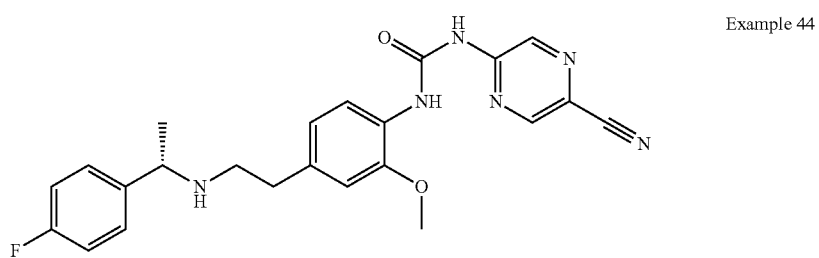
Example 44
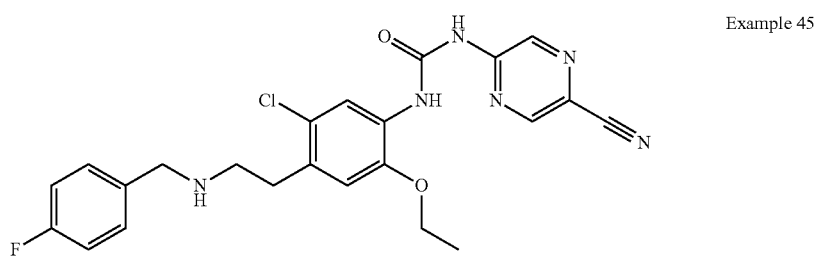
Example 45
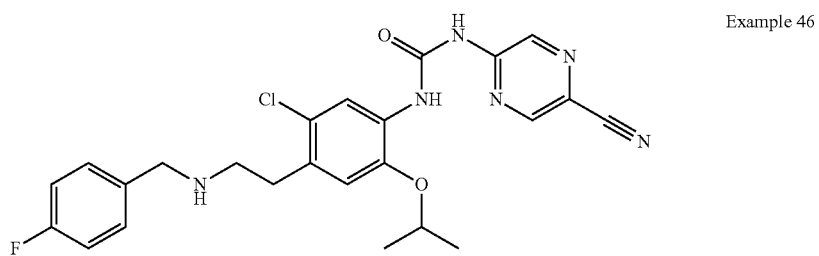
Example 46
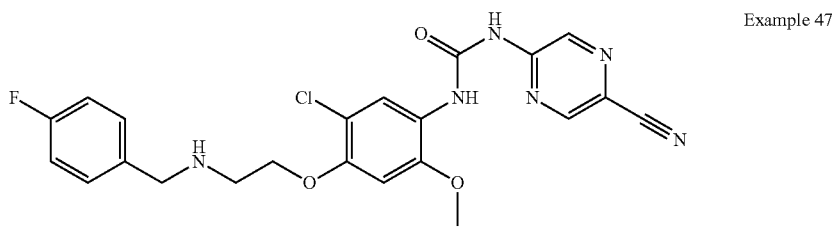
Example 47
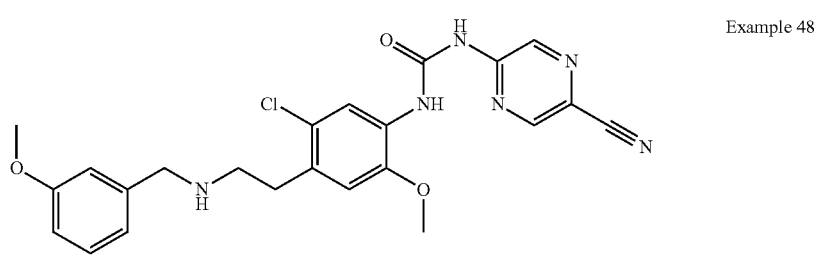
Example 48

TABLE 1-continued
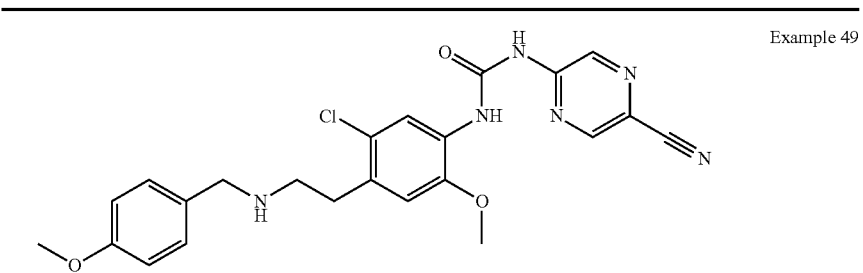
Example 49
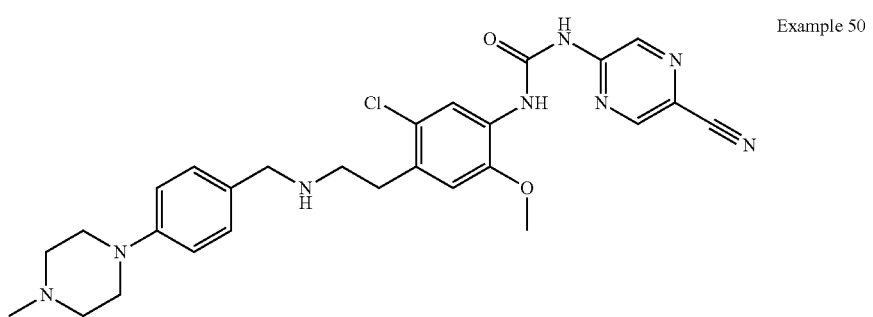
Example 50
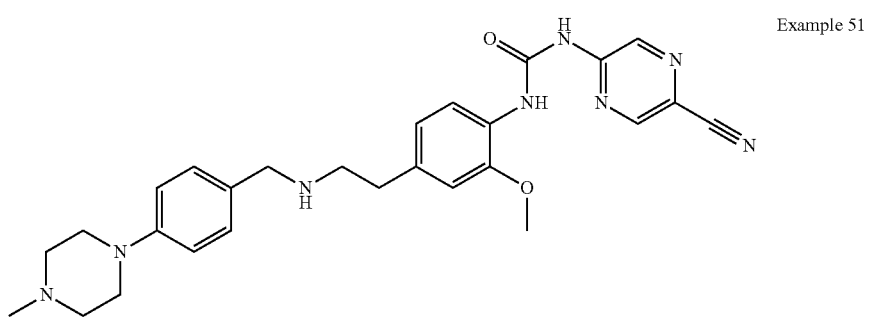
Example 51
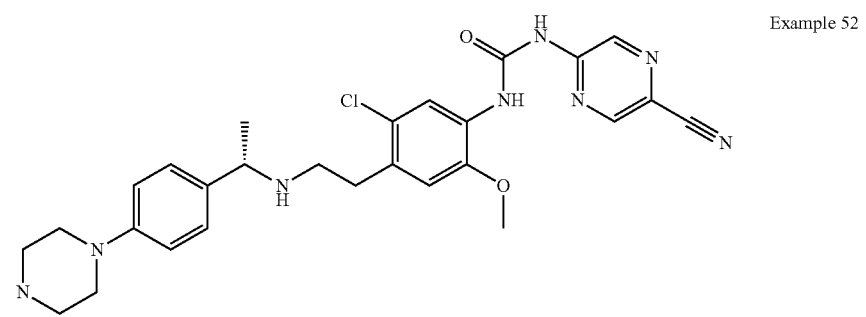
Example 52
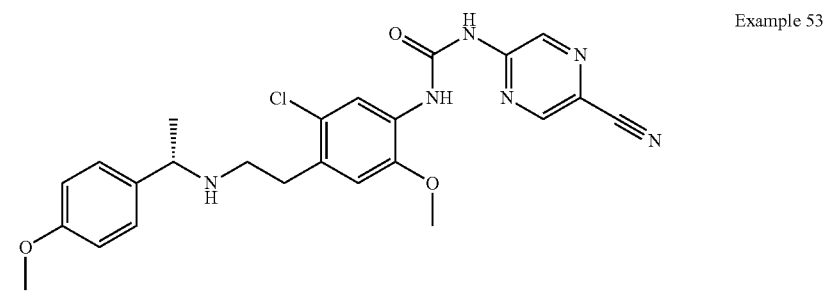
Example 53

TABLE 1-continued
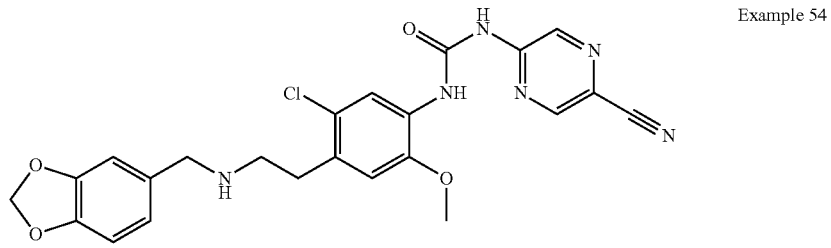
Example 54
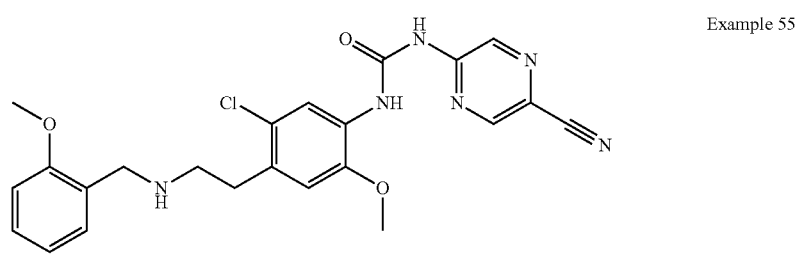
Example 55
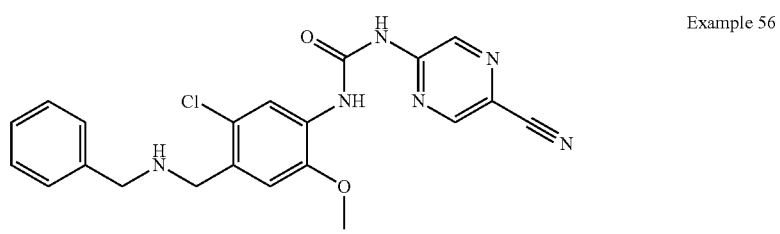
Example 56
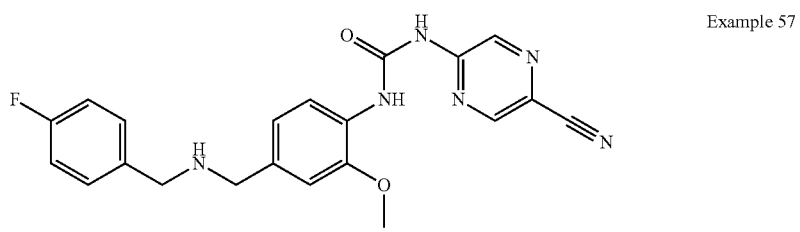
Example 57
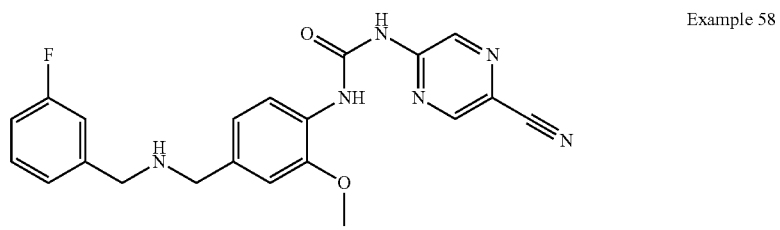
Example 58
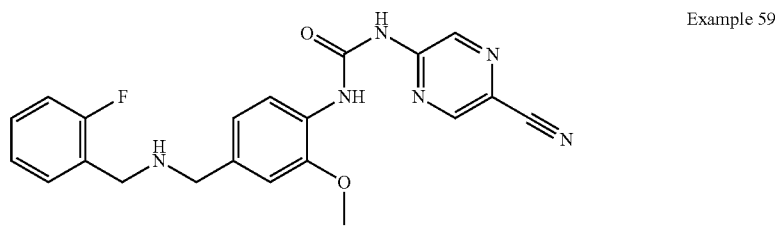
Example 59

TABLE 1-continued
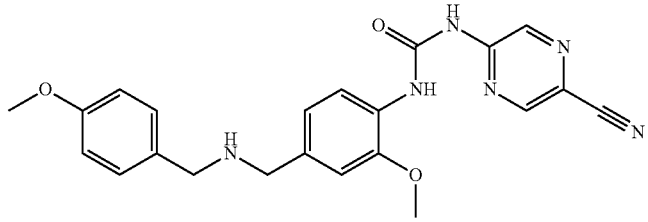 [SMILES: COc1ccc(CNCc2ccc(NC(=O)Nc3cnc(C#N)cn3)c(OC)c2)cc1] Example 60
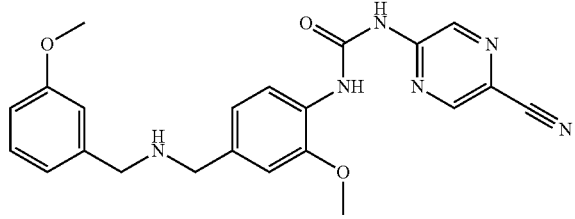 [SMILES: COc1cccc(CNCc2ccc(NC(=O)Nc3cnc(C#N)cn3)c(OC)c2)c1] Example 61
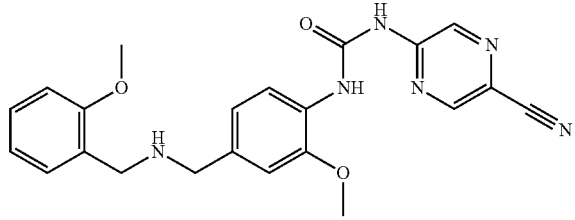 [SMILES: COc1ccccc1CNCc1ccc(NC(=O)Nc2cnc(C#N)cn2)c(OC)c1] Example 62
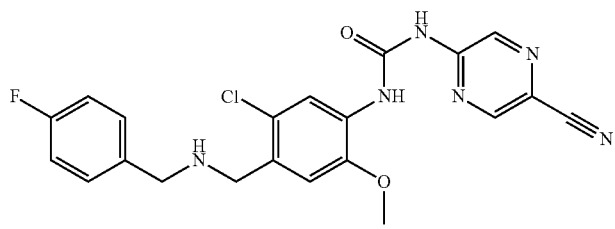 [SMILES: COc1cc(CNCc2ccc(F)cc2)c(Cl)cc1NC(=O)Nc1cnc(C#N)cn1] Example 63
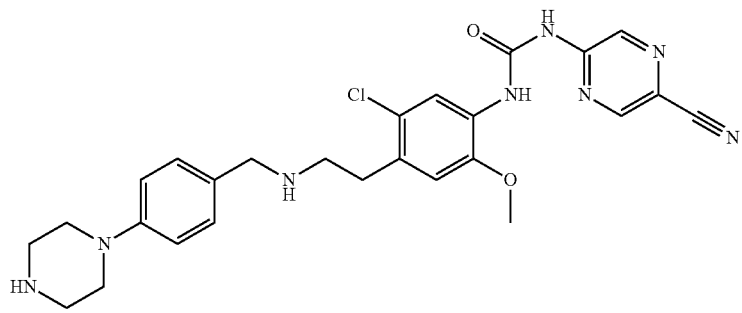 [SMILES: COc1cc(CCNCc2ccc(N3CCNCC3)cc2)c(Cl)cc1NC(=O)Nc1cnc(C#N)cn1] Example 64
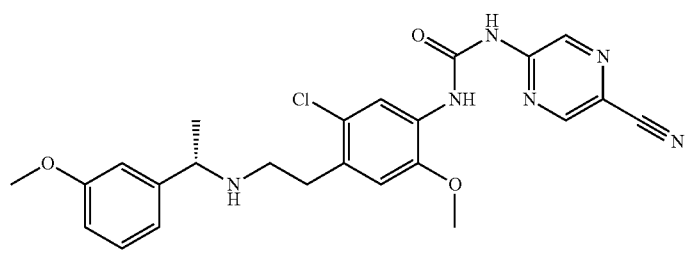 [SMILES: COc1cccc([C@H](C)NCCc2cc(OC)c(NC(=O)Nc3cnc(C#N)cn3)cc2Cl)c1] Example 65

TABLE 2

| Ex No. | Name | Synthetic method | $^1$H NMR | HPLC (RT) | LC (RT) | MS(M$^+$) | Method HPLC | Method MS |
|---|---|---|---|---|---|---|---|---|
| 1 | 1-[4-(2-Benzylamino-ethyl)-phenyl]-3-(5-cyano-pyrazin-2-yl)-urea | A | (DMSO-d$_6$) δ 9.59-9.42 (m, 1H), 9.20 (s, 1H), 8.87 (s, 1H), 7.47-6.99 (m, 10H), 3.85-3.54 (m, 2H), 2.85-2.56 (m, 4H) | | | 373 | | A |
| 2 | 1-(5-Cyano-pyrazin-2-yl)-3-{4-[2-(4-fluoro-benzylamino)-ethyl]-phenyl}-urea | A | (DMSO-d$_6$) δ 10.44-10.33 (br s, 1H), 9.77 (s, 1H), 9.39 (d, 1H), 9.07 (d, 1H), 7.76-7.70 (m, 2H), 7.67 (d, 2H), 7.50 (t, 2H), 7.42 (d, 2H), 4.35 (br s, 2H), 3.34-3.26 (br m, 2H), 3.12-3.03 (br m, 2H) | | 2.67 | 391 | | A |
| 3 | 1-(5-Cyano-pyrazin-2-yl)-3-{4-[2-(2,4-difluoro-benzylamino)-ethyl]-phenyl}-urea | A | (DMSO-d$_6$) δ 10.28-10.01 (br s, 1H), 9.56-9.45 (br s, 1H), 9.18 (d, 1H), 8.86 (d, 1H), 7.45 (q, 1H), 7.40 (d, 2H), 7.22-7.13 (m, 3H), 7.08-7.00 (m, 1H), 3.73-3.60 (br s, 2H), 2.71-2.66 (br s, 4H) | | 2.93 | 409 | | A |
| 4 | 1-{3-Chloro-4-[2-(4-fluoro-benzylamino)-ethyl]-phenyl}-3-(5-cyano-pyrazin-2-yl)-urea | B | (DMSO-d$_6$) δ 9.93 (s, 1H), 9.26 (s, 1H), 8.96 (s, 1H), 7.84 (d, 1H), 7.65-7.55 (m, 3H), 7.47-7.30 (m, 5H), 4.23 (br s, 2H), 3.22-3.02 (m, 4H) | 7.87 | 6.576 | 425 | A | B |
| 5 | 1-{3-Chloro-4-[2-(2,4-difluoro-benzylamino)-ethyl]-phenyl}-3-(5-cyano-pyrazin-2-yl)-urea | B$^a$ | (DMSO-d$_6$) δ 10.26 (d, 1H), 9.72 (d, 1H), 9.16-9.15 (s, 1H), 8.87-8.86 (s, 1H), 7.76-7.74 (s, 1H), 7.62-7.56 (q, 1H), 7.36-7.35 (s, 1H), 7.33-7.30(t, 2H), 7.20-7.15 (t, 1H), 4.12 (s, 2H), 3.05 (s, 2H), 2.97-2.95 (s, 2H). | 10.95 | 6.82 | 443 | A | B |
| 6 | 1-{3-Chloro-4-[2-(2,4-difluoro-benzylamino)-ethoxy]-phenyl}-3-(5-cyano-pyrazin-2-yl)-urea | C | (Methanol-d$_4$) δ 8.67 (s, 1H), 8.66 (s, 1H), 7.74-7.73 (d, 1H), 7.66-7.61 (m, 1H), 7.43-7.40 (dd, 1H), 7.18-7.10 (m, 3H), 4.46 (s, 1H), 4.46-4.36 (d, 2H), 3.58-3.55 (s, 2H) | | 7.06 | 459 | | D |
| 7 | 1-(3-Chloro-4-(2-(4-fluorophenethylamino)ethyl)phenyl)-3-(5-cyanopyrazin-2-yl)urea | B$^b$ | (DMSO d$_6$) δ 9.69 (s, 1H), 9.16-9.15 (s, 1H), 8.86 (s, 1H), 7.71 (s, 1H), 7.28-7.22 (t, 4H), 7.12-7.07 (t, 2H), 2.9-2.85 (m, 6H), 2.76-2.72 (t, 2H) | 11.05 | | | C | |
| 8 | 1-{3-Chloro-4-[2-(4-chloro-benzylamino)-ethyl]-phenyl}-3-(5-cyano-pyrazin-2-yl)-urea | B | (DMSO d$_6$) δ 9.61 (s, 1H), 9.14 (s, 1H), 8.85 (s, 1H), 7.68 (s, 1H), 7.32-7.26 (m, 5H), 3.68 (s, 2H), 2.78-2.76 (t, 2H) and 2.65-2.59 (t, 2H) | 8.122 | 6.915 | 443 | B | B |
| 9 | 1-{3-Chloro-4-[2-(3-fluoro-benzylamino)-ethyl]-phenyl}-3-(5-cyano-pyrazin-2-yl)-urea | B | (DMSO d$_6$) δ 9.63 (s, 1H), 9.17 (s, 1H), 8.88 (s, 1H), 7.71 (s, 1H), 7.36-7.26 (m, 3H), 7.15-7.12 (d, 2H), 7.05-7.00 (t, 1H), 3.74 (s, 2H), 2.82-2.79 (t, 2H) and 2.70-2.66 (t, 2H) | 7.828 | | 425 | B | A |
| 10 | 1-{3-Chloro-4-[2-(2-chloro-benzylamino)-ethyl]-phenyl}-3-(5-cyano-pyrazin-2-yl)-urea | B | (DMSO d$_6$) δ 8.17 (s, 1H), 7.85 (s, 1H), 6.90 (s, 1H), 6.61-6.42 (m, 6H), 3.11 (s, 2H), 2.12 (t, 2H) and 2.04 (t, 2H) | 7.955 | | 441 | B | A |
| 11 | 1-(3-Chloro-4-{2-[(4-fluoro-benzyl)-methyl-amino]-ethyl}-phenyl)-3-(5-cyano-pyrazin-2-yl)-urea | B | (DMSO d$_6$) δ 10.24 (s, 1H), 9.63 (s, 1H), 9.17 (s, 1H), 8.88 (s, 1H), 7.69 (s, 1H), 7.29-7.25 (m, 4H), 7.12-7.08 (t, 2H), 3.51 (s, 2H), 2.85-2.82 (t, 2H) and 2.21 (s, 3H) | 7.858 | | 439 | B | A |
| 12 | 1-{3-Chloro-4-[2-(3-methoxy-benzylamino)-ethyl]-phenyl}-3-(5-cyano-pyrazin-2-yl)-urea | B | (DMSO d$_6$) δ 9.63 (s, 1H), 9.17 (s, 1H), 8.88 (s, 1H), 7.71 (s, 1H), 7.31-7.18 (m, 3H), 6.89-6.76 (d, 3H), 3.69 (s, 1H), 3.367 (s, 2H), 2.82-2.79 (t, 2H) and 2.71-2.67 (t, 2H) | 7.823 | | 437 | B | A |
| 13 | 1-{3-Chloro-4-[2-(3-chloro-benzylamino)-ethyl]-phenyl}-3-(5-cyano-pyrazin-2-yl)-urea hydrochloride | D | (DMSO d$_6$) δ 10.37 (s, 1H), 10.06 (s, 1H), 9.21 (s, 1H), 9.16 (s, 1H), 8.88 (s, 1H), 7.76 (s, 1H), 7.66 (s, 1H), 7.50 (s, 3H), 7.39-7.33 (q, 2H), 4.22 (s, 2H) and 3.21-3.07 (t, 4H) | 8.030 | 6.450 | 443 | B | C |
| 14 | 1-{3-Chloro-4-[2-(4-trifluoromethoxy-benzylamino)-ethyl]-phenyl}-3-(5-cyano-pyrazin-2-yl)-urea | D | (DMSO d$_6$) δ 10.31(s, 1H), 9.78 (s, 1H), 9.18 (s, 1H), 8.99 (s, 1H), 8.88 (s, 1H), 7.77 (s, 1H), 7.66-7.63 (d, 2H), 7.49-7.47 (d, 2H), 7.39-7.32 (m, 2H) 4.26 (s, 2H) and 3.05-3.01 (t, 4H) | 9.731 | | 491 | B | A |
| 15 | 1-{3-Chloro-4-[2-(4-methoxy-benzylamino)-ethyl]-phenyl}-3-(5-cyano-pyrazin-2-yl)-urea | D | (DMSO d$_6$) δ 10.34(s, 1H), 9.95 (s, 1H), 9.20 (s, 1H), 8.93 (s, 1H), 7.76 (s, 1H), 7.44-7.31 (m, 4H),7.01-6.99 (d, 2H), 4.11 (s, 2H), 3.77 (s, 3H) and 3.06-3.03 (t, 4H) | 8.958 | | 437 | B | A |
| 16 | 1-{3-Chloro-4-[2-(2-methoxy-benzylamino)-ethyl]-phenyl}-3-(5-cyano-pyrazin-2-yl)-urea | D | (DMSO d$_6$) δ 10.35 (s, 1H), 10.01 (s, 1H), 9.20 (s, 1H), 8.88 (s, 1H), 8.86 (s, 1H), 7.76 (s, 1H), 7.45-7.33 (m, 4H), 7.12-7.10 (d, 1H), 7.03-7.00 (t, 1H), 4.17 (s, 2H), 3.85 (s, 3H) and 3.17-3.04 (m, 4H) | 8.924 | | 437 | B | A |
| 17 | 1-{3-Chloro-4-[2-(4-trifluoromethyl-benzylamino)-ethyl]-phenyl}-3-(5-cyano-pyrazin-2-yl)-urea hydrochloride | D | (DMSO d$_6$) δ 10.35 (s, 1H), 10.03 (s, 1H), 9.21 (s, 1H), 9.20 (s, 1H), 8.88 (s, 1H), 7.86-7.75 (m, 5H), 7.39-7.33 (m, 2H), 4.31 (s, 2H) and 3.16-3.04 (m, 4H) | 9.406 | 7.065 | 475 | B | D |

TABLE 2-continued

| Ex No. | Name | Synthetic method | $^1$H NMR | HPLC (RT) | LC (RT) | MS(M$^+$) | Method HPLC | MS |
|---|---|---|---|---|---|---|---|---|
| 18 | 1-(3-Chloro-4-{2-[(S)-1-(4-fluoro-phenyl)-ethylamino]-ethyl}-phenyl)-3-(5-cyano-yrazin-2-yl)-urea hydrochloride | D | (DMSO d$_6$) δ 10.36 (s, 1H), 10.08 (s, 1H), 9.52 (s, 1H), 9.20 (s, 2H), 8.87 (s, 1H), 7.72 (s, 1H), 7.64-7.60 (m, 2H), 7.35-7.27 (m, 4H), 4.50-4.45 (q, 1H), 3.07-2.78 (m, 4H) and 1.59-1.58 (d, 3H) | 8.029 | | 439 | B | A |
| 19 | 1-{5-Chloro-4-[2-(3-fluoro-benzylamino)-ethyl]-2-methoxy-phenyl}-3-(5-cyano-pyrazin-2-yl)-urea hydrochloride | E | (DMSO d$_6$) δ 10.81 (s, 1H), 10.03 (s, 1H), 9.22 (s, 2H), 9.04 (s, 1H), 8.94 (S, 1H), 8.26 (s, 1H), 7.55-7.27 (m, 4H), 7.09 (s, 1H), 4.24 (s, 2H), 3.94 (s, 3H), 3.16 (s, 2H) and 3.09-3.05 (d, 2H) | 9.08 | 6.943 | 457 | B | D |
| 20 | 1-(5-Cyano-pyrazin-2-yl)-3-{4-[2-(4-fluoro-benzylamino)-ethyl]-2-methoxy-phenyl}-urea | F | (DMSO d$_6$) δ 10.70 (s, 1H), 9.86 (s, 1H), 9.03 (s, 1H), 8.92 (s, 1H), 8.86 (s, 2H), 8.11-8.09 (d, 1H), 7.57-7.54 (q, 2H), 7.34-7.29 (t, 2H), 6.96 (s, 1H), 6.85-6.83 (d, 1H), 4.19 (s, 2H), 3.92 (s, 3H), 3.18 (s, 2H) and 2.93-2.89 (t, 2H) | 6.815 | 6.211 | 421 | C | D |
| 21 | 1-(5-Cyano-pyrazin-2-yl)-3-{4-[2-(4-fluoro benzylamino)-ethoxy]-2-methoxy-phenyl}-urea | C | (DMSO d$_6$) δ 10.59 (s, 1H), 9.68 (s, 1H), 8.99 (s, 1H), 8.88 (s, 1H), 7.97-7.95 (d, 1H), 7.47 (s, 2H), 7.20 (s, 2H), 6.65 (s, 1H), 6.54-6.52 (d, 1H), 4.11 (s, 2H), 3.98 (s, 2H), 3.87 (s, 3H) and 3.06 (s, 2H) | 6.510 | 8.579 | 437 | B | D |
| 22 | 1-[4-(Benzylamino-methyl)-2-methoxy-phenyl]-3-(5-cyano-pyrazin-2-yl)-urea | G | (DMSO d$_6$) δ 10.86-10.50 (1H, br s), 9.86 (1H, br s), 9.04 (1H, d), 8.93 (1H, d), 8.08 (1H, d), 7.40-7.30 (4H, m), 7.25 (1H, t), 7.09 (1H, br d), 6.92 (1H, br d), 3.91 (3H, s) and 3.72 (4H, d) | 8.442 | | 389 | A | A |
| 23 | 1-{3-Chloro-4-[2-(2-fluoro-benzylamino)-ethyl]-phenyl}-3-(5-cyano-pyrazin-2-yl)-urea | D | (DMSO d$_6$) δ 9.62 (s, 1H), 9.14 (s, 1H), 8.85 (s, 1H), 7.71-7.69 (s, 1H), 7.42-7.39 (t, 1H), 7.29-7.23 (m, 3H), 7.14-7.08 (m, 2H), 3.74 (s, 2H), 2.80-2.77 (t, 2H) and 2.70-2.67 (t, 2H) | 8.803 | 6.751 | 425 | B | D |
| 24 | 1-(3-Chloro-4-{2-[(R)-1-(4-fluoro-phenyl)-ethylamino]-ethyl}-phenyl)-3-(5-cyano-pyrazin-2-yl)-urea hydrochloride | D | (DMSO d$_6$) δ 10.37 (s, 1H), 10.11 (s, 1H), 9.55 (s, 1H), 9.213 (s, 1H), 9.21 (s, 1H), 8.88-8.87 (s, 1H), 7.73-7.72 (d, 1H), 7.65-7.61 (m, 2H), 7.36-7.28 (m, 4H), 4.50-4.45 (m, 1H), 3.17-2.73 (m, 4H) and 1.56-1.54 (d, 3H) | 8.986 | | 439 | B | A |
| 25 | 1-{3-Chloro-4-[2-(4-morpholin-4-yl-benzylamino)-ethyl]-phenyl}-3-(5-cyano-pyrazin-2-yl)-urea | D | (DMSO d$_6$) δ 9.62 (s, 1H), 9.14 (s, 1H), 8.85 (s, 1H), 7.69 (s, 1H), 7.27 (s, 2H), 7.17-7.15 (d, 2H), 6.87-6.85 (d, 2H), 3.71-3.69 (t, 4H), 3.64 (s, 2H), 3.05-3.03 (t, 4H), 2.80-2.78 (d, 2H) and 2.71-2.65 (d, 2H) | 7.446 | 6.116 | 492 | B | D |
| 26 | 1-{3-Chloro-4-[2-(4-fluoro-benzylamino)-ethoxy]-phenyl}-3-(5-cyano-pyrazin-2-yl)-urea | C | (DMSO d$_6$) δ 10.21 (s, 1H), 9.56 (s, 1H), 9.14 (s, 1H), 8.87 (s, 1H), 7.72-7.71 (d, 1H), 7.49-7.46 (t, 2H), 7.37-7.34 (dd, 1H), 7.24-7.15 (m, 3H), 4.20 (s, 2H, —CH2), 4.04 (s, 2H) and 3.16-3.12 (s, 2H) | 7.862 | | 441 | B | A |
| 27 | 1-{4-[2-(4-Fluoro-benzylamino)-ethyl]-2-methoxy-phenyl}-3-(5-methyl-pyrazin-2-yl)-urea hydrochloride | D | (DMSO d$_6$) δ 9.96 (s, 1H), 9.13 (br s, 2H), 8.77 (s, 1H), 8.22 (s, 1H), 8.11-8.09 (d, 1H), 7.61-7.58 (t, 2H), 7.32-7.28 (t, 1H), 6.94-6.93 (s, 1H), 6.81-6.79 (d, 1H), 4.19-4.16 (t, 2H), 3.91 (s, 3H), 3.16 (br s, 2H), 2.95-2.91 (t, 2H) and 2.42 (s, 3H) | 7.086 | | 410 | B | A |
| 28 | 1-(3-Chloro-4-{2-[2-(2,4-difluoro-phenyl)-ethylamino]-ethyl}-phenyl)-3-(5-cyano-pyrazin-2-yl)-urea | D | (DMSO d$_6$) δ 9.63 (s, 1H), 9.15 (s, 1H), 8.86 (s, 1H, -ArH), 7.69 (s, 1H), 7.35-7.26 (m, 3H), 7.16-7.11 (t, 1H), 6.99-6.96 (m, 1H) and 2.73-2.70 (m, 8H) | 8.292 | 6.731 | 457 | B | D |
| 29 | 1-[4-(Benzylamino-methyl)-phenyl]-3-(5-cyano-pyrazin-2-yl)-urea | G | (DMSO d$_6$) δ 10.28 (s, 1H), 9.71 (s, 1H), 9.21 (s, 1H), 9.18 (br s, 1H), 8.90 (s, 1H), 7.59 (d, 2H), 7.54-7.36 (m, 7H) and 4.23-4.08 (m, 2H) | 8.766 | | 359 | B | A |
| 30 | 1-(5-Cyano-pyrazin-2-yl)-3-{4-[2-(2,4-difluoro-benzylamino)-ethyl]-2-methoxy-phenyl}-urea | D | (DMSO d$_6$) δ 10.69 (s, 1H), 9.82 (s, 1H), 9.03 (s, 1H), 8.92-91 (s, 1H), 8.07-8.03 (d, 1H), 7.55-7.49 (q, 1H), 7.27-7.22 (t, 1H), 7.12-7.08 (t, 1H), 6.93 (s, 1H), 6.80-6.78 (d, 1H), 3.89 (s, 3H), 3.87 (s, 2H), 2.87 (m, 2H) and 2.77-2.76 (m, 2H) | 8.673 | 5.943 | 439 | B | D |
| 31 | 1-(5-Cyano-pyrazin-2-yl)-3-(4-{2-[2-(4-fluoro-phenyl)-ethylamino]-ethyl}-2-methoxy-phenyl)-urea | D | (DMSO d$_6$) δ 9.80 (s, 1H), 9.03 (s, 1H), 8.91 (s, 1H), 8.02-8.00 (d, 1H), 7.24-7.20 (q, 2H), 7.09-7.05 (t, 2H), 6.90 (s, 1H), 6.77-6.75 (d, 1H), 3.88 (s, 3H), 2.76-2.73 (t, 4H) and 2.69-2.64 (t, 4H) | 8.943 | 6.283 | 435 | B | D |
| 32 | 1-[4-(2-Benzylamino-ethyl)-2-methoxy-phenyl]-3-(5-methyl-pyrazin-2-yl)-urea hydrochloride | D | (DMSO d$_6$) δ 9.98 (s, 2H), 9.20 (s, 1H), 8.78 (s, 1H), 8.22 (s, 1H), 8.12-8.09 (d, 1H), 7.56-7.54 (d, 2H), 7.47-7.43 (d, 3H), 6.94 (s, 1H), 6.81-6.79 (d, 1H), 4.19-4.16 (t, 2H), 3.90 (s, 3H), 3.16 (s, 2H, —CH2), 2.96-2.92 (t, 2H) and 2.42 (s, 3H) | 6.890 | | 392 | B | A |
| 33 | 1-(5-Cyano-pyrazin-2-yl)-3-{4-[2-(2,4-difluoro- | C | (DMSO d$_6$) δ 10.58 (s, 1H), 9.66 (s, 1H), 9.01 (s, 1H), 8.89 (s, 1H), 7.97-7.94 (d, 1H), 7.55-7.49 | 8.529 | 6.789 | 455 | B | D |

TABLE 2-continued

| Ex No. | Name | Synthetic method | ¹H NMR | HPLC (RT) | LC (RT) | MS(M⁺) | Method HPLC | MS |
|---|---|---|---|---|---|---|---|---|
| | benzylamino)-ethoxy]-2-methoxy-phenyl}-urea | | (q, 1H), 7.21-7.16 (m, 1H), 7.09-7.04 (m, 1H), 6.65 (s, 1H), 6.53-6.50 (d, 1H), 4.04-4.01 (t, 2H), 3.88 (s, 3H), 3.78 (s, 2H) and 2.86-2.83 (t, 2H) | | | | | |
| 34 | 1-(5-Cyano-pyrazin-2-yl)-3-{3-[2-(4-fluoro-benzylamino)-ethyl]-phenyl}-urea | | (DMSO d₆) δ 9.48 (s, 1H), 9.19 (s, 1H), 8.87 (s, 1H), 7.36-7.31 (m, 4H), 7.26-7.22 (t, 1H), 7.14-7.09 (t, 2H), 6.93-6.91 (d, 1H), 3.70 (s, 2H) and 2.71 (s, 4H) | 7.481 | | 391 | B | A |
| 35 | 1-(3-Chloro-4-{2-[4-(4-methyl-piperazin-1-yl)-benzylamino]-ethyl}-phenyl)-3-(5-cyano-pyrazin-2-yl)-urea | D | (DMSO d₆) δ 10.37 (s, 1H), 9.90 (s, 1H), 9.20 (s, 1H), 8.89 (s, 1H), 7.78-7.77 (d, 1H), 7.40-7.38 (d, 2H), 7.34-7.32 (d, 2H), 7.08-7.05 (d, 2H), 4.12 (s, 2H), 3.87 (s, 2H), 3.50 (s, 2H), 3.08-3.05 (m, 8H) and 2.85 (s, 3H). | 7.328 | 4.323 | 505 | B | D |
| 36 | 1-(5-Cyano-pyrazin-2-yl)-3-{4-[2-(4-fluoro-benzylamino)-ethyl]-3-methyl-phenyl}-urea hydrochloride | D | (DMSO d₆) δ 10.37 (s, 1H), 9.91 (s, 1H), 9.25 (br s, 1H), 9.24 (s, 1H), 8.87 (s, 1H), 7.64-7.60 (q, 2H), 7.34-7.28 (m, 4H), 7.13-7.10 (d, 1H), 4.19 (s, 2H), 3.03 (t, 2H), 2.95-2.92 (t, 2H) and 2.29 (s, 3H) | 8.665 | 6.245 | 405 | B | D |
| 37 | 1-{5-Chloro-4-[2-(4-fluoro-benzylamino)-ethyl]-2-methoxy-phenyl}-3-(5-cyano-pyrazin-2-yl)-urea hydrochloride | H | (DMSO d₆) δ 10.83 (s, 1H), 10.03 (s, 1H), 9.25 (s, 1H), 9.04 (S, 1H), 8.94 (s, 1H), 8.26 (s, 1H), 7.63-7.60 (q, 2H), 7.33-7.29 (t, 2H), 7.10 (s, 1H), 4.22-4.19 (t, 2H), 3.94 (s, 3H) and 3.14-3.07 (t, 4H) | 8.032 | 7.995 | 455 | B | C |
| 38 | 1-(3-Chloro-4-{2-[3-(4-methyl-piperazin-1-yl)-benzylamino]-ethyl}-phenyl)-3-(5-cyano-pyrazin-2-yl)-urea | D | (DMSO d₆) δ 9.73 (s, 1H), 9.18 (s, 1H), 8.88 (s, 1H), 7.72 (s, 1H), 7.30 (s, 2H), 7.14 (s, 1H), 6.91 (s, 1H), 6.80-6.75 (dd, 2H), 3.75 (s, 2H), 3.09 (s, 4H), 2.83-2.78 (d, 4H), 2.44 (s, 4H) and 2.20 (s, 3H) | 7.459 | 4.167 | 505 | B | D |
| 39 | 1-{3-Chloro-4-[2-(3-morpholin-4-yl-benzylamino)-ethyl]-phenyl}-3-(5-cyano-pyrazin-2-yl)-urea | D | (DMSO d₆) δ 9.65 (s, 1H), 9.18 (s, 1H), 8.89 (s, 1H), 7.72 (s, 1H), 7.31 (s, 2H), 7.18-7.14 (t, 1H), 6.91 (s, 1H), 6.82-6.76 (m, 2H), 3.74-3.72 (d, 6H), 3.08-3.06 (t, 4H), 2.83 (t, 2H) and 2.74 (t, 2H) | 10.360 | | 492 | B | A |
| 40 | 1-{3-Chloro-4-[2-(3,4-difluoro-benzylamino)-ethyl]-phenyl}-3-(5-cyano-pyrazin-2-yl)-urea | D | (DMSO d₆) δ 9.66 (s, 1H), 9.17 (s, 1H), 8.88 (s, 1H), 7.71 (s, 1H), 7.39-7.34 (q, 2H), 7.29 (s, 2H), 7.16 (s, 1H), 3.73 (s, 2H), 2.83-2.79 (t, 2H) and 2.70-2.67 (t, 2H) | 7.952 | | 443 | B | A |
| 41 | 1-{3-Bromo-4-[2-(4-fluoro-benzylamino)-ethyl]-phenyl}-3-(5-cyano-pyrazin-2-yl)-urea hydrochloride | D | (DMSO d₆) δ 10.82 (s, 1H), 10.02 (s, 1H), 9.20 (br s, 1H), 9.04 (s, 1H), 8.95 (s, 1H), 8.42 (s, 1H), 7.63-7.60 (q, 2H), 7.33-7.29 (t, 2H), 7.10 (s, 1H), 4.21 (s, 2H), 3.94 (s, 3H) and 3.14-3.07 (t, 4H) | 8.988 | 6.710 | 470 | B | D |
| 42 | 1-{5-Bromo-4-[2-(4-fluoro-benzylamino)-ethyl]-2-methoxy-phenyl}-3-(5-cyano-pyrazin-2-yl)-urea hydrochloride | H | (DMSO d₆) δ 10.82 (s, 1H), 10.02 (s, 1H), 9.20 (br s, 1H), 9.04 (s, 1H), 8.95 (s, 1H), 8.42 (s, 1H), 7.63-7.60 (q, 2H), 7.33-7.29 (t, 2H), 7.10 (s, 1H), 4.21 (s, 2H), 3.94 (s, 2H) and 3.14-3.07 (t, 4H) | 8.024 | | 499 | B | A |
| 43 | 1-(5-Cyano-pyrazin-2-yl)-3-(4-{2-[(R)-1-(4-fluoro-phenyl)-ethylamino]-ethyl}-2-methoxy-phenyl)-urea | F | (DMSO d₆) δ 10.67 (s, 1H), 9.79 (s, 1H), 9.02 (s, 1H), 8.91 (s, 1H), 8.01-7.99 (d, 1H), 7.36 (q, 2H), 7.13 (t, 2H), 6.85 (s, 1H), 6.73-6.71 (d, 1H), 3.87 (s, 3H), 3.74 (d, 1 H), 2.67 (t, 2H), 2.61 (t, 2H) and 1.24 (d, 3H) | 8.988 | 6.571 | 435 | B | D |
| 44 | 1-(5-Cyano-pyrazin-2-yl)-3-(4-{2-[(S)-1-(4-fluoro-phenyl)-ethylamino]-ethyl}-2-methoxy-phenyl)-urea | F | (DMSO d₆) δ 9.79 (s, 1H), 9.02 (s, 1H), 8.92 (s, 1H), 8.01-7.99 (d, 1H), 7.36-7.32 (q, 2H), 7.13-7.09 (t, 2H), 6.85 (s, 1H), 6.73-6.71 (d, 1H, -ArH), 3.87 (s, 3H, —CH3), 3.74 (d, 1H, —CH), 2.67 (t, 2H), 2.63-2.60 (t, 2H) and 1.24-1.20 (d, 3H) | 8.655 | 6.571 | 435 | B | D |
| 45 | 1-{5-Chloro-2-ethoxy-4-[2-(4-fluoro-benzylamino)-ethyl]-phenyl}-3-(5-cyano-pyrazin-2-yl)-urea hydrochloride | H | (DMSO d₆) δ 11.00 (s, 1H), 10.14 (s, 1H), 9.21 (br s, 1H), 8.95 (s, 1 H), 8.86 (s, 1 H), 8.28 (s, 1H), 7.63-7.59 (q, 2H), 7.33-7.29 (t, 2H), 7.08 (s, 1H), 4.20 (s, 2H), 4.19-4.14 (q, 2H), 3.13 (t, 2H), 3.07-3.05 (t, 2H) and 1.47-1.45 (t, 3H) | 9.48 | 6.927 | 469 | B | D |
| 46 | 1-{5-Chloro-4-[2-(4-fluoro-benzylamino)-ethyl]-2-isopropoxy-phenyl}-3-(5-cyano-pyrazin-2-yl)-urea hydrochloride | H | (DMSO d₆) δ 11.03 (s, 1H), 10.07 (s, 1H), 9.09 (br s, 1H), 8.93 (s, 1H), 8.87 (s, 1H), 8.30 (s, 1H), 7.61-7.58 (q, 2H), 7.34-7.29 (t, 2H), 7.11 (s, 1H), 4.75-4.70 (m, 1H), 4.21 (s, 2H), 3.15 (t, 2H), 3.06-3.04 (t, 2H) and 1.38-1.36 (d, 6H) | 9.479 | 7.049 | 483 | B | D |
| 47 | 1-{5-Chloro-4-[2-(4-fluoro-benzylamino)-ethoxy]-2-methoxy-phenyl}-3-(5-cyano-pyrazin-2-yl)-urea hydrochloride | C | (DMSO d₆) δ 10.74 (s, 1H), 9.91 (s, 1H), 9.32 (br s, 1H), 9.03 (s, 1H), 8.93 (s, 1H), 8.22 (s, 1H), 7.64-7.61 (q, 2H), 7.34-7.30 (t, 2H), 6.99 (s, 1H), 4.41-4.39 (t, 2H), 4.32 (s, 2H) and 3.97 (s, 3H) | 9.057 | 5.298 | 471 | B | C |

TABLE 2-continued

| Ex No. | Name | Synthetic method | ¹H NMR | HPLC (RT) | LC (RT) | MS(M⁺) | Method HPLC | MS |
|---|---|---|---|---|---|---|---|---|
| 48 | 1-{5-Chloro-2-methoxy-4-[2-(3-methoxy-benzylamino)-ethyl]-phenyl}-3-(5-cyano-pyrazin-2-yl)-urea hydrochloride | H | (DMSO d₆) δ 10.33 (s, 1H), 10.28 (s, 1H), 9.91 (s, 1H), 9.20-9.19 (s, 1H), 8.89 (s, 1H), 7.79 (s, 1H), 7.43-7.41 (s, 2H), 7.30 (t, 1H), 7.18-7.16 (d, 2H), 4.70-4.66 (d, 2H), 4.38 (s, 1H), 3.82 (s, 1H) and 3.25-3.13 (t, 4H) | 9.337 | 5.356 | 467 | B | C |
| 49 | 1-{5-Chloro-2-methoxy-4-[2-(4-methoxy-benzylamino)-ethyl]-phenyl}-3-(5-cyano-pyrazin-2-yl)-urea hydrochloride | H | (DMSO d₆) δ 10.83 (s, 1H), 10.04 (s, 1H), 9.09 (s, 1H), 9.04 (s, 1H), 8.95 (s, 1H), 8.28-8.26 (s, 1H), 7.48-7.46 (d, 2H), 7.08 (s, 1H), 7.02-7.00 (d, 2H), 4.14 (s, 2H), 3.94 (s, 3H), 3.77 (s, 3H) and 3.11-3.07 (t, 4H) | 8.021 | 5.387 | 467 | B | C |
| 50 | 1-(5-Chloro-2-methoxy-4-{2-[4-(4-methyl-piperazin-1-yl)-benzylamino]-ethyl}-phenyl)-3-(5-cyano-pyrazin-2-yl)-urea hydrochloride | I | (DMSO d₆) δ 11.00 (s, 1H), 10.88 (s, 1H), 10.03 (s, 1H), 9.39 (s, 2H), 9.05 ( s, 1H), 8.94 (s, 1H), 8.24 (s, 1H), 7.47-7.44 (d, 2H), 7.11 (s, 1H), 7.06-7.04 (d, 2H), 4.08 (s, 2H), 3.93 (s, 3H), 3.88-3.86 (d, 2H), 3.49-3.47 (d, 2H), 3.16-3.09 (m, 8H) and 2.81-2.80 (d, 3H) | 5.120 | 3.424 | 535 | D | E |
| 51 | 1-(5-Cyano-pyrazin-2-yl)-3-(2-methoxy-4-{2-[4-(4-methyl-piperazin-1-yl)-benzylamino]-ethyl}-phenyl)-urea | F | (DMSO d₆) δ 9.79 (s, 1H), 9.03 (s, 1H), 8.92 (s, 1H), 8.02-8.00 (d, 1H), 7.15-7.13 (d, 2H), 6.90 (s, 1H), 6.87-6.85 (d, 2H), 6.78-6.75 (d, 1H), 3.89 (s, 3H), 3.61 (s, 2H), 3.09-3.07 (t, 4H), 2.70 (t, 4H), 2.45-2.42 (t, 4H) and 2.21 (s, 3H) | 5.268 | | 501 | B | A |
| 52 | 1-(5-Chloro-2-methoxy-4-{2-[(S)-1-(4-piperazin-1-yl-phenyl-ethylamino]-ethyl}-phenyl)-3-(5-cyano-pyrazin-2-yl)-urea hydrochloride | I | (DMSO d₆) δ 10.82 (s, 1H), 10.01 (s, 1H), 9.52 (s, 1H), 9.20 (s, 1H), 9.03-8.93 (s, 3H), 8.21 (s, 1H), 7.46-7.44 (d, 2H), 7.06-7.04 (m, 3H), 4.4 (s, 1H), 3.91 (s, 3H), 3.21 (s, 3H), 3.06 (m, 3H) and 1.58-1.56 (t,3 H) | 5.088 | | 535 | D | A |
| 53 | 1-(5-Chloro-2-methoxy-4-{2-[(S)-1-(4-methoxy-phenyl)-ethylamino]-ethyl}-phenyl)-3-(5-cyano-pyrazin-2-yl)-urea hydrochloride | I | (DMSO d₆) δ 9.95 (s, 1H), 9.02-8.92 (d, 2H), 8.16 (s,1H), 7.23-7.21 (d, 2H), 6.97 (s, 1H), 6.85-6.83 (d, 2H) 3.88 (s, 3H), 3.71 (s, 3H) 2.74-2.67 (d, 2H) 1.89 (q, 1H) and 1.22-1.20 (d, 7H) | | 3.967 | 481 | | E |
| 54 | 1-(4-{2-[(Benzo[1,3]-dioxol-5-ylmethyl)-amino]-ethyl}-5-chloro-2-methoxy-phenyl)-3-(5-cyano-pyrazin-2-yl)-urea hydrochloride | I | (DMSO d₆) δ 10.84 (s, 1H), 10.03 (s, 1H), 9.25 (s, 2H), 9.04 (s, 1H), 8.94 (s, 1H), 8.25 (s, 1H), 7.17-6.97 (m, 4H) 6.06 (s, 2H), 4.10 (s, 2H), 3.94 (s, 3H) and 3.08 (s, 4H) | | 6.385 | 480 | | F |
| 55 | 1-{5-Chloro-2-methoxy-4-[2-(2-methoxy-benzylamino)-ethyl]-phenyl}-3-(5-cyano-pyrazin-2-yl)-urea hydrochloride | I | (DMSO d₆) δ 10.85 (s, 1H), 10.03 (s, 1H), 9.12 (m, 2H), 9.04 (s, 1H), 8.93 (s, 1H), 8.24 (s, 1H), 7.50 (d, 1H, J 6.8 Hz), 7.45 (t, 1H, J 8 Hz), 7.03 (t, 1H, J 7.2 Hz), 4.17 (s, 2H), 3.94 (s, 3H), 3.85 (s, 3H) and 3.11 (m, 4H) | | 6.569 | 467 | | F |
| 56 | 1-[4-(Benzylamino-methyl)-5-chloro-2-methoxy-phenyl]-3-(5-cyano-pyrazin-2-yl)-urea hydrochloride | J | (DMSO d₆) δ 10.86 (s, 1H), 10.14 (s, 1H), 9.37 (br s, 1H), 9.04 (s, 1H), 8.96 (s, 1H), 8.33 (s, 1H), 7.56-7.41 (m, 6H), 4.23 (s, 4H) and 3.96 (s, 3H) | 7.881 | 7.168 | 423 | C | D |
| 57 | 1-(5-Cyano-pyrazin-2-yl)-3-{4-[(4-fluoro-benzylamino)-methyl]-2-methoxy-phenyl}-urea hydrochloride | G | (DMSO d₆) δ 10.78 (s, 1H), 9.99 (s, 1H), 9.31 (br, 2H), 9.04 (s, 1H), 8.94 (s, 1H), 8.22-8.20 (d, 1H), 7.59-7.56 (t, 2H), 7.32-7.28 (t, 3H), 7.08-7.06 (d, 1H), 4.15-4.11 (s, 4H) and 3.94 (s, 3H) | 8.491 | | 407 | B | A |
| 58 | 1-(5-Cyano-pyrazin-2-yl)-3-{4-[(3-fluoro-benzylamino)-methyl]-2-methoxy-phenyl}-urea hydrochloride | G | (DMSO d₆) δ 10.80 (s, 1H), 9.99 (s, 1H), 9.52 (s, 1H), 9.04 (s, 1H), 8.94 (s, 1H), 8.21-8.19 (d, 1H), 7.53-7.44 (m, 2H), 7.39-7.37 (d, 1H), 7.34 (s, 1H), 7.30-7.26-(t, 1H), 7.08-7.06 (d, 1H), 4.20-4.17 (t, 2H), 4.13 (t, 2H) and 3.94-3.93 (s, 3H) | 8.575 | 6.672 | 407 | B | D |
| 59 | 1-(5-Cyano-pyrazin-2-yl)-3-{4-[(2-fluoro-benzylamino)-methyl]-2-methoxy-phenyl}-urea hydrochloride | G | (DMSO d₆) δ 10.69 (br s, 1H), 9.84 (s, 1H), 9.04 (s, 1H), 8.93 (s, 1H), 8.08-8.06 9d, 1H), 7.53-7.49 (t, 1H), 7.31-7.28 (q, 1H), 7.21-7.13 (m, 2H), 7.09 (s, 1H), 6.92-6.90 (d, 1H), 3.91 (s, 3H), 3.72 (s, 2H) and 3.69 (s, 2H) | 8.398 | | 407 | B | |
| 60 | 1-(5-Cyano-pyrazin-2-yl)-3-{2-methoxy-4-[(4-methoxy-benzylamino)-methyl]-phenyl}-urea | G | (DMSO d₆) δ 10.71 (br s, 1H), 9.87 (s, 1H), 9.03 (s, 1H), 8.93 (s, 1H), 8.1-8.08 (d, 1H), 7.30-7.28 (d, 2H), 7.09 (s, 1H), 6.93-6.89 (t, 3H), 3.91 (s, 3H), 3.86 (s, 3H) and 3.70 (s, 4H) | 8.437 | 6.358 | 419 | B | D |
| 61 | 1-(5-Cyano-pyrazin-2-yl)-3-{2-methoxy-4-[(3-methoxy-benzylamino)- | G | (DMSO d₆) δ 10.81 (s, 1H), 9.99 (s, 1H), 9.452 (s, 1H), 9.05 (s, 1H), 8.94 (s, 1H), 8.21-8.19 (d, 1H), 7.38-7.33 (m, 2H), 7.17 (s, 1H), 7.09-7.07 | 8.602 | 6.411 | 419 | B | D |

TABLE 2-continued

| Ex No. | Name | Synthetic method | ¹H NMR | HPLC (RT) | LC (RT) | MS(M⁺) | Method HPLC | Method MS |
|---|---|---|---|---|---|---|---|---|
| | methyl]-phenyl}-urea hydrochloride | | (d, 2H), 7.00-6.98 (d, 1H), 4.12 (s, 4H), 3.94 (s, 3H) and 3.56 (s, 3H) | | | | | |
| 62 | 1-(5-Cyano-pyrazin-2-yl)-3-{2-methoxy-4-[(2-methoxy-benzylamino)-methyl]-phenyl}-urea | G | (DMSO $d_6$) δ 10.84 (s, 1H), 10.00 (s, 1H), 9.32 (s, 1H), 9.06 (s, 1H), 8.94 (s, 1H), 8.20-8.18 (d, 1H), 7.44-7.38 (m, 3H), 7.11-7.09 (t, 2H), 7.02-6.98 (t, 1H), 4.13 (s, 2H), 4.04 (s, 2H), 3.95 (s, 3H) and 3.81 (s, 3H) | 8.696 | 6.106 | 419 | B | D |
| 63 | 1-{5-Chloro-4-[(4-fluoro-benzylamino)-methyl]-2-methoxy-phenyl}-3-(5-cyano-pyrazin-2-yl)-urea hydrochloride | J | (DMSO $d_6$) δ 10.83 (s, 1H), 10.40 (br s, 1H), 10.04 (s, 1H), 9.12 (br s, 1H), 9.04 (s, 1H), 8.95 (s, 1H), 8.25 (s, 1H), 7.44-7.42 (d, 2H), 7.09 (s, 1H), 7.08-7.05 (d, 2H), 4.11 (s, 2H), 3.94 (s, 3H), 3.90-3.87 (d, 2H), 3.49-3.48 (t, 2H), 3.17-3.00 (m, 8H) and 2.84 (s, 3H) | 7.913 | 7.168 | 441 | B | D |
| 64 | 1-{5-Chloro-2-methoxy-4-[2-(4-piperazin-1-yl-benzylamino)-ethyl]-phenyl}-3-(5-cyano-pyrazin-2-yl)-urea hydrochloride | I | (DMSO $d_6$) δ 10.86 (s, 1H), 10.03 (s, 1H), 9.32 (s, 2H), 9.04 (s, 1H), 8.93 (s, 1H), 8.24 (s, 1H), 7.46-7.43 (d, 2H), 7.11 (s, 1H), 7.05-7.03 (d, 2H), 4.09 (s, 2H), 3.93 (s, 3H), 3.47-3.42 (m, 4H), 3.20-3.14 (s, 4H) and 3.08 (s, 4H) | 5.250 | | 521 | D | A |
| 65 | 1-(5-Chloro-2-methoxy-4-{2-[(S)-1-(3-methoxy-phenyl)-ethylamino]-ethyl}-phenyl)-3-(5-cyano-pyrazin-2-yl)-urea hydrochloride | I | (DMSO $d_6$) δ 10.82 (s, 1H), 10.01 (s, 1H), 9.72 (s, 1H), 9.34 (s, 1H), 9.03 (s, 1H), 8.93 (s, 1H), 8.21 (s, 1H), 7.38-7.34 (t, 1H), 7.22 (s, 1H), 7.13-7.12 (d, 1H), 7.05 (s, 1H), 6.98-6.96 (d, 1H), 4.39 (s, 1H), 3.91 (s, 3H), 3.78 (s, 3H), 3.03 (t, 2H), 2.83 (t, 2H) and 1.59 (s, 3H) | | 3.865 | 481 | | E |

[a]Example 5 was prepared using the Synthetic Method B except for the last step where the method described for Example 22F was used
[b]Example 7 was purified using Preparative HPLC Method 2
Synthetic Routes A, B, C, D, E, F, G, H, I and J are described below.

Synthetic Route A
(Illustrated with reference to Example 1: 1-[4-(2-Benzylamino-ethyl)-phenyl]-3-(5-cyano-pyrazin-2-yl)-urea)

Example 1

1A. Benzyl-[2-(4-nitro-phenyl)-ethyl]-carbamic acid tert-butyl ester 2-(4-Nitro-phenyl)-ethylamine (20 mmol) and benzaldehyde (20 mmol) were mixed in N,N-dimethylacetamide (50 ml) and acetic acid (5 ml) was added followed by NaBH(OAc)₃ (22 mmol). The mixture was stirred overnight. Saturated NaHCO₃ (100 ml) was then added carefully, followed by Boc₂O (22 mmol), and the reaction mixture was then stirred at room temperature for two hours. The product was extracted with DCM (3×), and the organic layers were combined and washed with brine (3×). The organic extract was dried (Na₂SO₄), concentrated and purified by column chromatography using a gradient of 0-50% EtOAc in hexanes to afford benzyl-[2-(4-nitro-phenyl)-ethyl]-carbamic acid tert-butyl ester.

1B. [2-(4-Amino-phenyl)-ethyl]-benzyl-carbamic acid tert-butyl ester

Benzyl-[2-(4-nitro-phenyl)-ethyl]-carbamic acid tert-butyl ester (100 mmol) was dissolved in THF (20 ml) and hydrogenated under a pressure of one atmosphere overnight. The reaction mixture was filtered and washed with THF. The filtrate was concentrated to dryness and was used directly in the procedure for Example 1D.

1C. (5-Cyano-pyrazin-2-yl)-carbamic acid phenyl ester

2-Amino 5-cyano pyrazine (0.25 g, 2.08 mmol) was dissolved in THF and DCM (3:1, 40 mL) and pyridine (0.49 g, 6.2 mmol) was added. The mixture was stirred for 15 minutes. Phenylchloroformate (0.97 g, 6.2 mmol) was added and the reaction mixture was heated at 50° C. for 2 hours. The reaction mixture was cooled to RT and DCM (40 mL) and water (25 mL) were added. The separated organic layer was washed with water (2×25 mL), brine (25 mL), dried (Na₂SO₄) and the solvents evaporated under reduced pressure. The product was purified by column chromatography on neutral silica gel using 15-20% EtOAc in hexane to give the title compound (0.29 g, 54%).

1D. Benzyl-(2-{4-[3-(5-cyano-pyrazin-2-yl)-ureido]-phenyl}-ethyl)-carbamic acid tert-butyl ester 2-(4-Amino-phenyl)-ethyl]-benzyl-carbamic acid tert-butyl ester (2 mmol) was mixed with (5-cyano-pyrazin-2-yl)-carbamic acid phenyl ester (2 mmol) in 1,4-dioxane and the mixture was subjected to microwave heating at 130° C. for 15 minutes. The reaction mixture was then concentrated and purified by column chromatography on neutral silica using 0-100% ethyl acetate in hexanes to afford the title compound benzyl-(2-{4-[3-(5-cyano-pyrazin-2-yl)-ureido]-phenyl}-ethyl)-carbamic acid tert-butyl ester.

1E. 1-[4-(2-Benzylamino-ethyl)-phenyl]-3-(5-cyano-pyrazin-2-yl)-urea

Benzyl-(2-{4-[3-(5-cyano-pyrazin-2-yl)-ureido]-phenyl}-ethyl)-carbamic acid tert-butyl ester (1 mmol) was treated with 4N HCl in dioxane (10 ml) and stirred overnight at room temperature. The product was precipitated by addition of dry ether. The crude was purified by column using 0-100% 7 N NH₃/MeOH in DCM to afford the title compound as a free base.

Synthetic Route B
(Illustrated with reference to Example 4: 1-{3-Chloro-4-[2-(4-fluoro-benzylamino)-ethyl]-phenyl}-3-(5-cyano-pyrazin-2-yl)-urea)

Example 4

4A. 2-(2-Chloro-4-nitro-phenyl)-malonic acid dimethyl ester

3-Chloro 4-fluoro nitrobenzene (5.0 g, 28.48 mmol) and dimethyl malonate (3.3 mL, 36.17 mmol) were dissolved in N-methylpyrrolidinone (131.5 mL). Sodium hydroxide (2.4 g, 60 mmol) was added at RT and the solution was heated at 80° C. for 2 hours. The reaction mixture was cooled to 5° C. and 1N HCl solution was added to give a pH of 2. Water (526 mL) was added and the resulting mixture was stirred for 15 minutes during which a pale yellow solid precipitated out. The precipitate was collected by filtration and then washed with water (2×10 mL). The resulting solid mass was dissolved in DCM (50 mL), dried ($Na_2SO_4$) and then the volatiles were removed under reduced pressure to afford the title compound (5.5 g, 67%). The product was used as such in the next step without purification.

4B. (2-Chloro-4-nitro-phenyl)-acetic acid methyl ester 2-(2-Chloro-4-nitro-phenyl)-malonic acid dimethyl ester (6.0 g, 20.9 mmol) and sodium chloride (2.2 g, 37.6 mmol) were added to a mixture of DMSO (100 mL) and water (0.38 mL, 20.9 mmol) and the reaction mixture was heated for 8 hours at 110° C. The reaction mixture was cooled to RT and poured into water (500 mL). EtOAc (200 mL) was added to the mixture which was then stirred for 15 minutes. The separated aqueous phase was extracted with EtOAc (100 mL). The combined organic extracts were washed with brine (100 mL), dried ($Na_2SO_4$) and the solvents removed under reduced pressure. The residue was purified by column chromatography on neutral silica gel using 3-6% EtOAc in hexane to give the title compound (2.9 g, 60%).

4C. 2-(2-Chloro-4-nitro-phenyl)-ethanol (2-Chloro-4-nitro-phenyl)-acetic acid methyl ester (17 g, 74 mmol) was dissolved in dry THF (85 mL) and cooled to 0° C. A solution of $LiBH_4$ in THF (2M, 75 mL, 148 mmol) was added drop-wise at 0° C. and the reaction mixture was maintained for 5 hours at RT. After completion of reaction, $NH_4Cl$ solution (2 mL) was added to the reaction mixture which was then stirred for 15 minutes. EtOAc (170 mL) and water (85 mL) were added and stirred for 10 minutes. The separated aqueous layer was extracted with EtOAc (85 mL), then the combined organic extracts were dried ($Na_2SO_4$) and evaporated under reduced pressure to give a yellow oil. The oil was purified by column chromatography on neutral silica gel using 5-10% EtOAc in hexane to give the title compound (10 g, 55%).

4D. (2-Chloro-4-nitro-phenyl)-acetaldehyde

To a stirred suspension of 1,1,1-tris(acetyloxy)-1,1-dihydro-1,2-N-benzodioxol-3(1H)-one (Dess-Martin periodinane) (25.24 g, 59 mmol) in DCM (92 mL) was added a solution of 2-(2-chloro 4-nitro-phenyl)ethanol (10 g, 49 mmol) in DCM (30 mL) at RT. The reaction mixture was stirred for 3 hours at RT. After completion of reaction, sodium bicarbonate solution was added and the mixture was stirred for 15 minutes. The separated organic layer was washed with water (2×50 mL), dried ($Na_2SO_4$) and the solvent removed under reduced pressure to afford the title compound (9.5 g, 95%).

4E. [2-(2-Chloro-4-nitro-phenyl)-ethyl]-(4-fluoro-benzyl)-amine 2-(2-Chloro 4-nitro-phenyl)acetaldehyde (3.0 g, 15.03 mmol) and 4-fluorobenzylamine (1.88 g, 15.02 mmol) were added to methanol (45 mL) at RT and stirred for 15 minutes. The reaction mixture was cooled to 0° C. and acetic acid (15 mL) followed by solid $NaBH_4$ (0.56 g, 15.0 mmol) were added. The reaction mixture was allowed to warm to RT and stirring continued for 2 hours. The volatiles were then removed under reduced pressure. Dichloromethane (60 mL) and water (60 mL) were added and the mixture was stirred for 15 minutes. The separated organic layer was washed with water (60 mL), brine (60 mL), dried ($Na_2SO_4$) and the solvents removed under reduced pressure to afford the title compound (3.1 g, 67%) which was used in the next step without further purification.

4F. [2-(2-Chloro-4-nitro-phenyl)-ethyl]-(4-fluoro-benzyl)-amine hydrochloride To a suspension of [2-(2-chloro-4-nitro-phenyl)-ethyl]-(4-fluoro-benzyl)-amine (3.1 g, 10 mmol) in DCM (31 mL) was added 15% HCl in dioxane (2.4 mL, 10 mmol) at 0° C. and the mixture was maintained for 1 hour at 0° C. After completion of salt formation, the volatiles were removed under reduced pressure. A mixture of 4:1 hexane and ethyl acetate (50 mL) was added to the residue and this was stirred for 15 minutes. The solvent was removed by filtration under suction and the solid was dried under reduced pressure to afford crude title product (2.8 g, 80%).

4G. [2-(2-Chloro-4-nitro-phenyl)-ethyl]-(4-fluoro-benzyl)-carbamic acid tert-butyl ester To a suspension of N-[2-(2-chloro-4-nitro-phenyl)-ethyl]-(4-fluoro-benzyl)-amine hydrochloride (2.2 g, 6.38 mmol) in DCM (22 mL) was added triethylamine (1.78 mL, 12.7 mmol) followed by $Boc_2O$ (1.67 g, 7.6 mmol). The mixture was stirred for 1 hour at RT, then DCM (22 mL) and water (11 mL) were added and the reaction mixture was stirred for 15 minutes. The separated organic layer was washed with water (11 mL), dried ($Na_2SO_4$) and the solvents removed under reduced pressure. The crude product was purified by column chromatography on neutral silica using 1-3% EtOAc in hexane to give the title compound (1.2 g, 46%).

4H. [2-(4-Amino-2-chloro-phenyl)-ethyl]-(4-fluoro-benzyl)-carbamic acid tert-butyl ester To a solution of [2-(2-chloro-4-nitro-phenyl)ethyl]-(4-fluoro-benzyl)-carbamic acid tert-butyl ester (0.6 g, 1.4 mmol) in methanol (18 mL) was added a saturated solution of $NH_4Cl$ (18 mL), followed by zinc powder (0.41 g, 7.3 mmol) and the reaction mixture was heated at 45° C. for 1 hour. The reaction mixture was cooled to RT, filtered and EtOAc (60 mL) and water (100 mL) were added to the filtrate and the mixture was stirred for 15 minutes. The separated organic phase was washed with water (80 mL), brine (80 mL), dried ($Na_2SO_4$) and the solvents removed under reduced pressure to afford the title compound (0.49 g, 88%).

4I. (2-{2-Chloro-4-[3-(5-cyano-pyrazin-2-yl)-ureido]-phenyl}-ethyl)-(4-fluoro-benzyl)-carbamic acid tert-butyl ester 2-(4-Amino-2-chloro-phenyl)ethyl]-(4-fluoro-benzyl)-carbamic acid tert-butyl ester (0.49 g, 1.29 mmol) and (5-cyano-pyrazin-2-yl)-carbamic acid phenyl ester (0.46 g, 1.94 mmol) (Example 10) were dissolved in DMF (4.9 mL) and heated at 75° C. for 10 hours. The reaction mixture was cooled to RT, water (24 mL) and EtOAc (12 mL) was added to the reaction mixture and the organic layer was separated. The organic layer was washed with water (24 mL), brine (24 mL), dried (Na$_2$SO$_4$) and the volatiles removed under reduced pressure. The product was purified by column chromatography on neutral silica gel using 10-20% EtOAc in hexane to give the title compound (0.29 g, 42.7%).

4J. 1-{3-Chloro-4-[2-(4-fluoro-benzylamino)-ethyl]-phenyl}-3-(5-cyano-pyrazin-2-yl)-urea TFA (0.26 mL, 3.4 mmol) was added to a solution of (2-{2-chloro-4-[3-(5-cyano-pyrazin-2-yl)-ureido]-phenyl}-ethyl)-(4-fluoro-benzyl)-carbamic acid tert-butyl ester (0.18 g, 0.34 mmol) in DCM (18 mL) at 10° C. The mixture was stirred for four hours then the solvents were removed under reduced pressure. A mixture of hexane (8 mL) and EtOAc (2 mL) was added and the resulting mixture was stirred for 15 minutes. The solvent was decanted off and the volatiles were removed under vacuum at 40° C. to afford title compound as the TFA salt (0.12 g, 84%).

The TFA salt was converted to the free base by the following procedure.

1-{3-Chloro-4-[2-(4-fluoro-benzylamino)-ethyl]-phenyl}-3-(5-cyano-pyrazin-2-yl)-urea trifluoroacetate (0.11 g, 0.2 mmol) was dissolved in EtOAc (11 mL) and the mixture was cooled to 0° C. A solution of NH$_3$ in IPA (0.11 mL, 1.0 mmol) was added to the reaction mixture and the temperature was maintained at 0° C. for 1 hour. The volatiles were removed under reduced pressure, water (1 mL) was added and reaction mixture was stirred for 15 minutes to give a precipitate. The precipitate was collected, washed with water (2×0.2 mL) and then dried under reduced pressure at 40° C. to afford the title compound (0.075 g, 95%).

Synthetic Route C
(Illustrated with reference to Example 6: 1-{3-Chloro-4-[2-(2,4-difluoro-benzylamino)-ethoxy]-phenyl}-3-(5-cyano-pyrazin-2-yl)-urea)

Example 6

6A. 2-(2,4-difluorobenzylamino)ethanol

Reference: WO2003106440

Ethanolamine (0.86 g, 14.07 mmol) was added to a solution of 2,4-difluorobenzaldehyde (2.0 g, 14.07 mmol) in methanol (50 mL) at RT. Sodium bicarbonate (7.0 g, 83.33 mmol) was added and the reaction mixture was stirred at reflux for 24 hours. The mixture was cooled to 0° C. and sodium borohydride (0.32 g, 8.42 mmol) was then added in lots, maintaining the temperature of the mixture at 0-5° C. The reaction mixture was allowed to warm to RT over a period of 4 hours. The reaction mixture was then diluted with DCM (50 mL), washed with brine (2×30 mL), dried (Na$_2$SO$_4$) and the solvents removed under reduced pressure to afford the title compound (1.79 g, 69%). The product was used in the next step without further purification.

6B. tert-Butyl 2,4-difluorobenzyl(2-hydroxyethyl)carbamate

Reference: WO/2005/026111

To 1M sodium hydroxide solution (14 mL) was added 2-(2,4-difluorobenzylamino) ethanol (1.79 g, 9.57 mmol) and the resulting mixture was cooled to 0° C. Di-t-butyl dicarbonate (2.08 g, 9.57 mmol) and DCM (50 mL) were added at a temperature of −5° C. and the reaction mixture was stirred vigorously for 6 hours gradually allowing the temperature to rise to RT. The separated organic layer was washed with water (3×30 mL), dried (Na$_2$SO$_4$) and evaporated under reduced pressure to give the title compound (2.34 g, 90%) as a colourless oil.

6C. tert-butyl 2-(2-chloro-4-nitrophenoxy)ethyl(2,4-difluorobenzyl)carbamate Reference: EP1852423 A1

Sodium hydride (0.101 g, 3.83 mmol, 95% in oil) was added to N,N-dimethyl formamide (20 mL) at −5 to 0° C. under nitrogen. The suspension was stirred for 10 minutes and to the resulting cooled mixture was added a solution of tert-butyl 2,4-difluorobenzyl(2-hydroxyethyl)carbamate (1.1 g, 4.21 mmol) in N,N-dimethylformamide (10 mL), maintaining the temperature at −5 to 0° C. during addition. The reaction mixture was stirred further for 20 minutes and then a solution of 3-chloro-4-fluoro-nitrobenzene (0.67 g, 3.83 mmol) in N,N-dimethyl formamide (10 mL), was added dropwise, maintaining the temperature in the range −5 to 0° C. The reaction mixture was allowed to warm to room temperature and stirred for 30 minutes. Water (300 mL) was then added to the reaction mixture and the resulting mixture was extracted with EtOAc (3×50 mL). The combined organic extracts were washed with brine (2×30 mL), dried (Na$_2$SO$_4$) and evaporated under reduced pressure. The residue was purified by column chromatography on neutral silica gel using 5-20% EtOAc in hexane to give the title compound (1.8 g, 60%).

6D. tert-Butyl 2-(4-amino-2-chlorophenoxy)ethyl(2,4-difluorobenzyl)carbamate To a solution of tert-butyl 2-(2-chloro-4-nitrophenoxy) ethyl-(2,4-difluorobenzyl)-carbamate (1.8 g, 4.06 mmol) in 70% aqueous ethanol (30 mL) was added sodium dithionite (2.87 g, 16.25 mmol), and the reaction mixture was heated to reflux for 3 hours. The hot reaction mixture was filtered and the residue washed with EtOAc (30 mL). The combined organic extracts were washed with brine (2×20 mL), dried (Na$_2$SO$_4$) and concentrated to give the title product (1.6 g, 95%) which was used in the next step without further purification.

6E. tert-Butyl 2-(2-chloro-4-(3-(5-cyanopyrazin-2-yl)ureido)phenoxy)ethyl(2,4-difluorobenzyl)carbamate To a solution of tert-butyl 2-(4-amino-2-chlorophenoxy) ethyl(2,4-difluorobenzyl)-carbamate (1.6 g, 3.87 mmol) in N,N-dimethylformamide (4 mL) at RT were phenyl 5-cyanopyrazin-2-ylcarbamate (1.39 g, 5.81 mmol) (Example 10) and N,N,N-diisopropylethylamine (0.751 g, 5.81 mmol) added. The reaction mixture was heated at 60° C. for 1.5 hours then the reaction mixture was poured into ice-water (100 mL) and allowed to stand for 30 minutes. The resulting precipitate was collected, washed with water and air dried. The crude product was purified by column chromatography on neutral silica gel using 0-2% methanol in DCM to give the title compound (0.53 g, 26% yield).

6F. 1-{3-Chloro-4-[2-(2,4-difluoro-benzylamino)-ethoxy]-phenyl}-3-(5-cyano-pyrazin-2-yl)-urea To a solution of tert-butyl 2-(2-chloro-4-(3-(5-cyanopyrazin-2-yl)ureido)phenoxy)ethyl-(2,4-difluorobenzyl)carbamate (0.53 g, 0.95 mmol) in tetrahydrofuran (5 mL) at 0° C. was added trifluoroacetic acid (1.19 g, 9.5 mmol), and the resulting mixture was heated at 40° C. for 12 hours. The solvent was removed under reduced pressure to leave a residue that was purified by preparative HPLC (Preparative HPLC Method 1) to give the title compound (44 mg, 10%).

Synthetic Route D
(Illustrated with reference to Example 13: 1-{3-Chloro-4-[2-(3-chloro-benzylamino)-ethyl]-phenyl}-3-(5-cyano-pyrazin-2-yl)-urea hydrochloride)

Example 13

13A. 1-(2-Bromoethyl)-2-chloro-4-nitrobenzene

The title compound was prepared by bromination of 2-(2-chloro-4-nitro-phenyl)-ethanol (Example 4C).

13B. 2-(2-Chloro-4-nitrophenyl)-N-(3-chlorobenzyl) ethanamine

To a solution of 1-(2-bromoethyl)-2-chloro-4-nitrobenzene (0.6 g, 1.84 mmol) in DMSO (20 mL), 3-chlorobenzylamine (1.21 g, 4.61 mmol) was added at room temperature. The reaction mixture was stirred for 3 hours at room temperature. After the completion of reaction, water (80 mL) was added and reaction mass was extracted with EtOAc (2×50 mL). The combined organic extracts were washed with water (50 mL), brine (50 mL) and the solvents removed under reduced pressure. The product was purified by column chromatography on neutral silica gel using 5-15% EtOAc in hexane to give the title compound (0.43 g, 55%) as a solid.

13C. 1-{3-Chloro-4-[2-(3-chloro-benzylamino)-ethyl]-phenyl}-3-(5-cyano-pyrazin-2-yl)-urea hydrochloride The synthesis was completed using the synthetic steps and chemistry described for Example 4.

Synthetic Route E
(Illustrated with reference to Example 19: 1-{5-Chloro-4-[2-(3-fluoro-benzylamino)-ethyl]-2-methoxy-phenyl}-3-(5-cyano-pyrazin-2-yl)-urea hydrochloride)

Example 19

19A. 1-Chloro-2-fluoro-4-methoxy-5-nitrobenzene

To a mixture of potassium tert-butoxide (3.0 g, 26.9 mmol) in DMF (20 mL), methanol (0.79 g, 24.8 mmol) was added at 0° C. The reaction mixture was stirred at 0° C. for 15 minutes then a solution of 1-chloro-2,4-difluoro-5-nitrobenzene (4.0 g, 20.7 mmol) in DMF (20 mL) was added at 0° C. and the reaction mass stirred for 3 hours at room temperature. Water (200 mL) was added to the reaction mixture and reaction mass was extracted with EtOAc (3×50 mL). The combined organic extracts were washed with water (80 mL), brine (80 mL), dried ($Na_2SO_4$) and concentrated under reduced pressure. The product was purified by column chromatography on neutral silica gel using 20-25% EtOAc in hexane to give the desired product (3 g, 71%) as a solid.

19B. Dimethyl 2-(2-chloro-5-methoxy-4-nitrophenyl)malonate 1-chloro-2-fluoro-4-methoxy-5-nitrobenzene (3.05 g, 14.83 mmol) and dimethyl malonate (2.5 g, 18.84 mmol) were added to N-methylpyrrolidinone (50 mL) at room temperature. Sodium hydroxide (1.25 g, 31.14 mmol) was added and the temperature was raised to 80° C. and maintained for 2 hours. The reaction mass was cooled to 5° C. then 1 N HCl solution was added to adjust the pH to 2. Water (300 mL) was added and the mixture stirred for 15 minute at 5° C. The precipitate was collected by filtration, washed with water (2×10 mL), dissolved in DCM (60 mL), dried ($Na_2SO_4$) and the solvent removed under reduced pressure. The residue was purified by column chromatography on neutral silica gel using 10-20% EtOAc in hexane to give the title compound (3.2 g, 68%) as a solid.

19C. 2-(2-Chloro-5-methoxy-4-nitrophenyl)acetic acid methyl ester

A mixture of dimethyl 2-(2-chloro-5-methoxy-4-nitrophenyl)malonate (3.0 g, 9.44 mmol) and sodium chloride (0.99 g, 16.99 mmol) in DMSO (50 mL) and water (0.17 mL, 9.44 mmol) was heated for 5 hours at 120° C. The reaction mass was allowed to cool to room temperature and water (400 mL) and EtOAc (50 mL) were added and stirring continued for 15 minutes. The separated aqueous layer was extracted with EtOAc (50 mL), and then the combined organic layers were washed with brine (50 mL), dried ($Na_2SO_4$) and concentrated under reduced pressure. The crude residue was purified by column chromatography on neutral silica gel using 15-25% EtOAc in hexane to give the desired material (1.5 g, 61%) as a solid.

19D. 2-(2-Chloro-5-methoxy-4-nitrophenyl)ethanol

A solution of $LiBH_4$ (2.0 M in THF, 3.8 mL, 7.7 mmol) was added to a solution of 2-(2-chloro-5-methoxy-4-nitrophenyl) ethanol (1.0 g, 3.85 mmol) at 0° C. in THF (20 mL). The solution was allowed to warm to room temperature and stirring continued for 5 hours. $NH_4Cl$ solution was added, stirring continued for 15 minutes then EtOAc (25 mL) and water (25 mL) were added. The separated aqueous layer was extracted with EtOAc (25 mL) then the combined organic extracts were dried ($Na_2SO_4$) and concentrated under reduced pressure. The residue was purified by column chromatography on neutral silica gel using 20-30% EtOAc in hexane to give the desired compound (0.65 g, 73%) as a solid.

19E. 1-(2-Bromoethyl)-2-chloro-5-methoxy-4-nitrobenzene

To a solution of 2-(2-chloro-5-methoxy-4-nitrophenyl) ethanol (0.85 g, 3.67 mmol) in DCM (20 mL), triphenylphosphine (1.54 g, 5.9 mmol) and carbon tetrabromide (1.46 g, 4.4 mmol) were added. The reaction mixture was maintained for 7 hours at room temperature then partitioned between water (50 mL) and EtOAc (80 mL). The separated aqueous phase was extracted with EtOAc (80 mL), then the combined organic extracts were dried ($Na_2SO_4$) and concentrated under reduced pressure. The product was purified by column chromatography on neutral silica gel using 5-15% EtOAc in hexane to give the title compound (0.9 g, 83%) as a solid.

19F. 2-(2-Chloro-5-methoxy-4-nitrophenyl)-N-(3-fluorobenzyl)ethanamine

To a solution of 1-(2-bromoethyl)-2-chloro-5-methoxy-4-nitrobenzene (0.8 g, 2.71 mmol) in DMSO (20 mL), 3-fluorobenzyl amine (0.85 g, 6.8 mmol) was added at room temperature. The reaction mixture was stirred for 5 hours at room temperature then water (80 mL) was added and the mixture extracted with EtOAc (2×50 mL). The combined organic extracts were washed with water (50 mL), brine (50 mL), dried ($Na_2SO_4$) and concentrated under reduced pressure. The residue was purified by column chromatography on neutral silica gel using 10-15% EtOAc in hexane to give the title compound (0.7 g, 87%) as a solid.

19G. Tert-butyl-2-chloro-5-methoxy-4-nitrophenethyl(3-fluorobenzyl)carbamate To a suspension of 2-(2-chloro-5-methoxy-4-nitrophenyl)-N-(3-fluorobenzyl)-ethanamine (0.7 g, 2.07 mmol) in dichloromethane (20 mL), triethylamine (0.52 g, 5.16 mmol) and BOC anhydride (0.54 g, 2.5 mmol) were added and the mixture was stirred for 1 hour at room temperature. The mixture was partitioned between DCM (50 mL) and water (50 mL), and then the separated organic phase was washed with water (50 mL), dried ($Na_2SO_4$) and concentrated under reduced pressure. The residue was purified by column chromatography on neutral silica gel using 6-8% EtOAc in hexane to give the title compound (0.8 g, 88%) as solid.

19H. Tert-butyl 4-amino-2-chloro-5-methoxyphenethyl(3-fluorobenzyl)carbamate To a solution of tert-butyl 2-chloro-5-methoxy-4-nitrophenethyl(3-fluorobenzyl)-carbamate (0.7 g, 1.59 mmol) in methanol (30 mL), saturated solution of $NH_4Cl$ (30 mL) was added followed by zinc powder (0.52 g, 7.98 mmol) and the mixture heated to 45° C. for 1.0 h. The mixture was allowed to cool to room temperature, filtered through celite then partitioned between EtOAc (25 mL) and water (50 mL). The separated aqueous phase was extracted with EtOAc (50 mL), then the combined organic extracts were washed with water (50 mL), brine (50 mL), dried ($Na_2SO_4$) and concentrated under reduced pressure to give the title compound (0.48 g, 74%).

19I. Tert-butyl 2-chloro-4-(3-(5-cyanopyrazin-2-yl)ureido)-5-methoxyphenethyl(3-fluorobenzyl)carbamate A solution of tert-butyl 4-amino-2-chloro-5-methoxyphenethyl(3-fluorobenzyl)-carbamate (0.3 g, 0.74 mmol) and phenyl-5-chloropyrazin-2-ylcarbamate (0.18 g, 0.74 mmol) in DMF (30 mL) was heated to 100° C. for 2 hours. The mixture was partitioned between water (200 mL) and EtOAc (50 mL) and the separated aqueous layer was extracted with EtOAc (50 mL). The combined organic extracts were washed with water (200 mL), brine (200 mL), dried ($Na_2SO_4$) and concentrated under reduced pressure. The crude product was purified by column chromatography on neutral silica gel using 20-30% EtOAc in hexane to give the title compound (0.19 g, 47%) as a solid.

19J. 1-(5-chloro-4-(2-(3-fluorobenzylamino)ethyl)-2-methoxyphenyl)-3-(5-cyanopyrazin-2-yl)urea hydrochloride A solution of HCl in 1,4-dioxane (0.5 mL) was added to a solution of tert-butyl 2-chloro-4-(3-(5-cyanopyrazin-2-yl)ureido)-5-methoxyphenethyl(3-fluorobenzyl)carbamate (0.22 g 0.4 mmol) in DCM (30 mL) at 0° C. and the mixture stirred at 10° C. for 2 hours. The solvents were removed under reduced pressure to leave a solid residue that was washed with methanol (2×5 mL) and dried under reduced pressure to give the title compound (100 mg, 51%) as an off-white solid.

Synthetic Route F
(Illustrated with reference to Example 20:1-(5-Cyano-pyrazin-2-yl)-3-{4-[2-(4-fluoro-benzylamino)-ethyl]-2-methoxy-phenyl}-urea)

Example 20

20A. 2-(3-methoxy-4-nitrophenyl)acetic acid

The title compound was prepared using methods described in *J. Med. Chem.* 2007, 50, 3841-3850.

20B. Methyl 2-(3-methoxy-4-nitrophenyl)acetate

A solution of 2-(3-methoxy-4-nitrophenyl)acetic acid (4.6 g, 21.78 mmol) and concentrated $H_2SO_4$ (2 drops) in methanol (200 mL) was heated to reflux for 3 hours. The mixture was allowed to cool to room temperature then the solvents were removed under reduced pressure. The residue was partitioned between water (100 mL) and EtOAc (100 mL), then the separated organic layer was washed with sodium bicarbonate solution (100 mL), brine (200 mL), dried ($Na_2SO_4$) and evaporated under reduced pressure to give the title compound (4.5 g, 92%) as a solid.

20C. Tert-butyl 4-(3-(5-cyanopyrazin-2-yl)ureido)-3-methoxyphenethyl (4-fluorobenzyl)carbamate The title compound was prepared using the synthetic steps and chemistry described for the synthesis of examples 19D, 19E, 19F, 19G, 19H, 19I

20D. N-(4-(3-(5-cyanopyrazin-2-yl)ureido)-3-methoxyphenethyl)-2,2,2-trifluoro-N-(4-fluorobenzyl)acetamide trifluoroacetate TFA (1.64 g, 14.42 mmol) was added to a solution of tert-butyl 4-(3-(5-cyanopyrazin-2-yl)ureido)-3-methoxyphenethyl (4-fluorobenzyl)carbamate (1.5 g, 2.88 mmol) in DCM (100 mL) at 10° C. and the reaction stirred for 4 hours. The solvents were removed under reduced pressure to give the title compound (1.5 g, 97%).

20E. Tert-butyl 2-chloro-4-(3-(5-cyanopyrazin-2-yl)ureido)phenethyl(2-methoxybenzyl)carbamate Liquid $NH_3$ (5.0 mL) was added to a solution of N-(4-(3-(5-cyanopyrazin-2-yl)ureido)-3-methoxyphenethyl)-2,2,2-trifluoro-N-(4-fluorobenzyl)acetamide trifluoroacetate (1.5 g, 2.80 mmol) in DCM (80 mL) at 0° C. and the mixture maintained for 1 hour at 0° C. The mixture was partitioned between water (100 mL) and EtOAc (100 mL) and the separated organic layer was washed with water (100 mL), brine (150 mL), dried ($Na_2SO_4$) and evaporated under reduced pressure to give the title compound (0.80 g, 68%).

20F. Tert-butyl 2-chloro-4-(3-(5-cyanopyrazin-2-yl)ureido)phenethyl(2-methoxybenzyl)carbamate hydrochloride A solution of HCl in 1,4-dioxane (3.5 mL) was added to a solution of tert-butyl 2-chloro-4-(3-(5-cyanopyrazin-2-yl)ureido)phenethyl(2-methoxybenzyl)carbamate (1.1 g, 2.61 mmol) in DCM (80 mL) at −10° C. The mixture was stirred at −10° C. for 1 hour then pentane (100 mL) was added. The resulting precipitate was collected by filtration and dried under reduced pressure to give the title compound (0.95 g, 92%) as a white solid.

Synthetic Route G
(Illustrated with reference to Example 22: 1-[4-(Benzylamino-methyl)-2-methoxy-phenyl]-3-(5-cyano-pyrazin-2-yl)-urea)

Example 22

22A. 4-Bromomethyl-2-methoxy-1-nitro-benzene

A solution of 4-nitro-3-methoxybenzyl alcohol (1.0 g, 5.46 mmol) in THF (5 ml) was cooled to 0° C. and carbon tetrabromide (3.62 g, 10.92 mmol) and triphenylphosphine (1.57 g, 6.00 mmol) were added. The reaction mixture was stirred at 0° C. for 2 hours then the solvents were removed under reduced pressure. The residue was purified by column chromatography on neutral silica gel using 5-8% EtOAc in hexane to give the title compound (1.25 g, 93%).

22B. Benzyl-(3-methoxy-4-nitro-benzyl)-amine

To a solution of 4-(bromomethyl)-2-methoxy-1-nitrobenzene (1.0 g, 4.06 mmol) in THF (15 ml), triethylamine (1.23 g, 12.19 mmol) and benzyl amine (1.3 g, 12.19 mmol) were added at RT and the reaction was stirred for 2 hours. The reaction mixture was partitioned between water (50 ml) and EtOAc (25 ml) and the separated aqueous layer was extracted with EtOAc (15 ml). The combined organic extracts were dried ($Na_2SO_4$) and concentrated under reduced pressure. The crude product was purified by column chromatography on neutral silica gel using 15-25% EtOAc in hexane to give the title compound (1.0 g, 91%).

22C. Benzyl-(3-methoxy-4-nitro-benzyl)-carbamic acid tert-butyl ester

To a suspension of benzyl-(3-methoxy-4-nitro-benzyl) amine (1.0 g, 3.67 mmol) in DCM (5 mL), Boc anhydride (0.96 g 4.4 mmol) was added and the mixture stirred for 18 hours at RT. DCM (5 mL) and a saturated solution of sodium bicarbonate (10 mL) were added and the mixture was stirred for 15 minutes. The layers were separated and the aqueous layer was extracted with dichloromethane (5 ml). The combined organic extracts were washed with brine (10 mL), dried ($Na_2SO_4$) and concentrated under reduced pressure to give the title compound (3 g, 95%).

22D. (4-Amino-3-methoxy-benzyl)-benzyl-carbamic acid tert-butyl ester

To a solution of benzyl-(3-methoxy-4-nitro-benzyl)-carbamic acid tert-butyl ester (1.2 g, 3.22 mmol) in methanol (24 mL) was added a saturated aqueous solution of $NH_4Cl$ (24 mL) and zinc powder (1.05 g 16.11 mmol). The reaction was heated to 60° C. for 2 hours then the reaction mass was cooled to room temperature and filtered through celite. The solvents were removed under reduced pressure then the residue was partitioned between EtOAc (24 mL) and water (24 mL). The separated aqueous layer was extracted with EtOAc (12 ml), and then the combined organic extracts were washed with water (24 mL), brine (24 mL), dried ($Na_2SO_4$) and concentrated under reduced pressure to give the title compound (0.94 g, 85%).

22E. Benzyl-{4-[3-(5-cyano-pyrazin-2-yl)-ureido]-3-methoxy-benzyl}-carbamic acid tert-butyl ester (4-Amino-3-methoxy-benzyl)-benzyl-carbamic acid tert-butyl ester (0.25 g, 0.73 mmol) and phenyl 5-cyanopyrazin-2-ylcarbamate (0.21 g 0.87 mmol) (Example 10) were dissolved in DMF (2.5 mL) and heated at 80° C. for 2 hours. The mixture was allowed to cool to room temperature then partitioned between water (15 mL) and EtOAc (25 mL). The separated aqueous layer was extracted with EtOAC (25 ml), and then the combined organic extracts were washed with water (15 mL), brine (10 mL), dried ($Na_2SO_4$) and concentrated under reduced pressure. The residue was purified by column chromatography on neutral silica gel using 15-25% EtOAc in hexane to afford the title compound (0.24 g, 67%).

22F. 1-[4-(Benzylamino-methyl)-2-methoxy-phenyl]-3-(5-cyano-pyrazin-2-yl)-urea

TFA (0.097 mL, 1.28 mmol) was added to a solution of benzyl-{4-[3-(5-cyano-pyrazin-2-yl)-ureido]-3-methoxy-benzyl}-carbamic acid tert-butyl ester (0.125 g, 0.25 mmol) in DCM (12.5 mL). The solution was stirred for 2 hours then the solvents were removed under reduced pressure.

The TFA salt (85 mg) was dissolved in methanol (17 mL) and tetraalkylammonium carbonate resin (119 mg) was added to the reaction mixture at RT. The reaction mixture was stirred for 2 hours then the reaction mixture was filtered and the resin washed with methanol (8.5 ml). The filtrate was concentrated under reduced pressure to afford the title product (60 mg, 91%) as a white solid.

Synthetic Route H
(Illustrated with reference to Example 37: 1-{5-Chloro-4-[2-(4-fluoro-benzylamino)-ethyl]-2-methoxy-phenyl}-3-(5-cyano-pyrazin-2-yl)-urea)

37A. 1-Chloro-2-fluoro-4-methoxy-5-nitrobenzene

To a suspension of potassium tert-butoxide (15.07 g, 134.3 mmol) in toluene (100 mL), and the appropriate alcohol, in this case methanol (3.80 g, 118.7 mmol), was added at 0° C. and stirred for 15 minutes. A solution of the appropriate 1-substituted 2,4-difluoro-5-nitrobenzene, in this case 1-chloro-2,4-difluoro-5-nitrobenzene (20.0 g, 103.3 mmol), in toluene (50 mL) was added at 0° C. and stirred for 5 hours at room temperature. Water (1000 mL) was added and the mixture was extracted with EtOAc (3×100 mL). The combined organic extracts were washed with water (150 mL), brine (150 mL), dried ($Na_2SO_4$) and concentrated under reduced pressure. The crude residue was purified by column chromatography on neutral silica gel using 5-10% EtOAc in hexane to give the title compound (11.0 g, 52%) as a solid.

37B. Dimethyl 2-(2-chloro-5-methoxy-4-nitrophenyl)malonate

Sodium hydroxide (4.49 g, 112.3 mmol) was added at room temperature to a stirred solution of 1-chloro-2-fluoro-4-methoxy-5-nitrobenzene (11.0 g, 53.5 mmol) and dimethyl malonate (8.976 g, 67.9 mmol) in N-methylpyrrolidinone (110 mL). The mixture was heated to 80° C. for 2 hours then cooled to 5° C. The pH of the mixture was adjusted to 2 using aq. 1N HCl solution then water (600 mL) was added gradually with stirring over 15 minute at 5° C. The precipitated solid was collected by filtration and washed with water (2×20 mL). The filtered solid was dissolved in dichloromethane (150 mL), dried (Na$_2$SO$_4$) and concentrated under reduced pressure to give the title compound (15.5 g, 91%).

37C. 2-(2-chloro-5-methoxy-4-nitrophenyl)ethanol

A solution of dimethyl 2-(2-chloro-5-methoxy-4-nitrophenyl)malonate (15.5 g, 48.7 mmol), sodium chloride (5.70 g, 97.5 mmol) and water (0.876 mL, 48.7 mmol) in DMSO (200 mL) was heated to 120° C. for 2 hours. The cooled reaction mixture was partitioned between water (1000 mL) and EtOAc (200 mL) and the separated aqueous phase was extracted with EtOAc (200 mL). The combined organic extracts were washed with brine (150 mL), dried (Na$_2$SO$_4$) and concentrated under reduced pressure. The crude product was purified by column chromatography on neutral silica gel using 3-10% EtOAc in hexane to give the title compound (10.2 g, 86%) as a solid.

37D. 2-(2-Chloro-5-methoxy-4-nitrophenyl)ethanol

Methyl 2-(2-chloro-5-methoxy-4-nitrophenyl)acetate (10.2 g, 41.86 mmol) was dissolved in dry THF (200 mL) and cooled to 0° C. A 2M solution of LiBH$_4$ in THF (41.86 mL, 83.73 mmol) was added at 0° C. over 20 minutes then the mixture was allowed to warm to room temperature and stirred for 5 hours. Saturated NH$_4$Cl solution was added to the reaction cautiously and stirred further for 15 minutes then EtOAc (150 mL) and water (150 mL) were added. The separated aqueous phase was extracted with EtOAc (100 mL) then the combined organic extracts were dried (Na$_2$SO$_4$) and concentrated under reduced pressure. The residue was purified by column chromatography on neutral silica gel using 0-2% methanol in DCM to give the title compound (7.0 g, 72%) as a solid.

37E. 1-(2-Bromoethyl)-2-chloro-5-methoxy-4-nitrobenzene

A solution of 2-(2-chloro-5-methoxy-4-nitrophenyl)ethanol (7.0 g, 30.22 mmol), triphenylphosphine (12.68 g, 48.3 mmol) and carbon tetrabromide (14.03 g, 42.3 mmol) in DCM (150 mL) was stirred at room temperature for 2 hours. The mixture was partitioned between water (150 mL) and EtOAc (100 mL), and then the separated aqueous phase was extracted with EtOAc (100 mL). The combined organic extracts were washed with water (80 mL), brine (80 mL), dried (Na$_2$SO$_4$) and concentrated under reduced pressure. The crude product was purified by column chromatography on neutral silica gel using 0-1% methanol in DCM to give the title compound (8.0 g, 90%) as a solid.

37F. 2-(2-Chloro-5-methoxy-4-nitrophenyl)-N-(4-fluorobenzyl)methanamine

To a solution of 1-(2-bromoethyl)-2-chloro-5-methoxy-4-nitrobenzene (7.0 g, 23.7 mmol) in DMSO (100 mL), triethylamine (8.25 mL, 59.2 mmol) and 4-fluorobenzylamine (3.56 g, 28.5 mmol) were added at room temperature and the mixture stirred for 5 hours. After completion of the reaction, water (500 mL) was added and the mixture was extracted with EtOAc (2×150 mL). The combined organic extracts were washed with water (100 mL), brine (100 mL), dried (Na$_2$SO$_4$) and concentrated under reduced pressure. The crude product was purified by column chromatography on neutral silica gel using 15-20% EtOAc in hexane to give the title compound (1.5 g, 19%) as a solid.

37G. Tert-butyl 2-chloro-5-methoxy-4-nitrophenethyl(4-fluorobenzyl)carbamate To a suspension of 2-(2-chloro-5-methoxy-4-nitrophenyl)-N-(4-fluorobenzyl)-ethanamine (2.5 g, 7.3 mmol) in DCM (40 mL), triethylamine (1.87 g, 18.4 mmol) and Boc anhydride (1.90 g, 8.7 mmol) were added at room temperature and the mixture stirred for 1 hour. The mixture was partitioned between DCM (80 mL) and water (80 mL) then the separated organic phase was washed with water (80 mL), dried (Na$_2$SO$_4$) and concentrated under reduced pressure. The residue was purified by column chromatography on neutral silica gel using 0-2% methanol in DCM to give the title compound (3.0 g, 93%).

37H. Tert-butyl 4-amino-2-chloro-5-methoxyphenethyl (4-fluorobenzyl)carbamate To a solution of tert-butyl 2-chloro-5-methoxy-4-nitrophenethyl(4-fluorobenzyl)-carbamate (3.0 g, 6.84 mmol) in methanol (120 mL), saturated solution of NH$_4$Cl (90 mL) was added at room temperature. Zinc powder (2.23 g, 34.2 mmol) was added at room temperature and the temperature was raised to 45° C. and maintained for one hour. The reaction mass was cooled to room temperature and filtered through a pad of celite. The filtrate was partitioned between EtOAc (250 mL) and water (500 mL) then the separated aqueous phase was extracted with EtOAc (100 mL). The combined organic extracts were washed with water (100 mL), brine (100 mL), dried (Na$_2$SO$_4$) and concentrated under reduced pressure to afford the title compound (2.7 g, 92%).

37I. Tert-butyl 2-chloro-4-(3-(5-cyanopyrazin-2-yl)ureido)-5-methoxyphenethyl (4-fluorobenzyl)carbamate A solution of tert-butyl 4-amino-2-chloro-5-methoxyphenethyl (4-fluorobenzyl)carbamate (2.7 g, 6.61 mmol) and phenyl 5-chloropyrazin-2-ylcarbamate (3.172 g, 13.22 mmol) in DMF (100 mL) was heated to 100° C. for 2 hours. The mixture was allowed to cool to room temperature and partitioned between water (200 mL) and EtOAc (200 mL). The separated aqueous phase was extracted with EtOAc (200 mL) and the combined organic extracts washed with water (200 mL), brine (200 mL), dried (Na$_2$SO$_4$) and concentrated under reduced pressure. The residue was purified by column chromatography on neutral silica gel using 0-3% methanol in DCM to give the title compound (2.24 g, 61%) as a solid.

37J. 1-(5-chloro-4-(2-(4-fluorobenzylamino)ethyl)-2-methoxyphenyl)-3-(5-cyanopyrazin-2-yl)urea hydrochloride A solution of HCl in 1,4-dioxane (0.05 mL) was added to a solution of tert-butyl 2-chloro-4-(3-(5-cyanopyrazin-2-yl)ureido)-5-methoxyphenethyl(4-fluorobenzyl)-carbamate (0.03 g, 0.4 mmol) in DCM (5 mL) at 0° C. The solution was allowed to warm to 10° C. and stirred at this temperature for one hour. The solvents were removed under reduced pressure and the residue was washed with methanol (2×5 mL) to give the title compound (0.017 g, 68%) as a white solid.

Synthetic Route I
(Illustrated with reference to Example 50: 1-(5-chloro-2-methoxy-4-(2-(4-(4-methylpiperazin-1-yl)benzylamino)ethyl)phenyl)-3-(5-cyanopyrazin-2-yl)urea hydrochloride)

Example 50

50A. 1-bromo-2-chloro-5-fluoro-4-nitrobenzene

Potassium nitrate (2.91 g, 28.8 mmol) was gradually added to a stirred solution of 1-bromo-2-chloro-5-fluorobenzene (5 g, 24 mmol) in concentrated sulphuric acid (50 mL) at −5° C. The reaction was stirred for 10 hours then slowly poured in to crushed ice with stirring. The formed precipitate was collected by filtration and dried under reduced pressure to give the title compound (4.7 g, 77%) as a solid.

50B. 1-bromo-2-chloro-5-fluoro-4-nitrobenzene

Sodium methoxide (0.043 g, 0.8 mmol) was slowly added to a stirred solution of 1-bromo-2-chloro-5-fluoro-4-nitrobenzene (0.2 g, 0.8 mmol) in methanol (2 mL) at 0° C. The reaction was stirred at 0° C. for 1.5 hours then water (30 mL) was added and the mixture was extracted with EtOAc (2×20 mL). The combined organic extracts were dried ($Na_2SO_4$) and concentrated under reduced pressure to give the title compound (0.15 g, 75%).

50C. 1-chloro-4-methoxy-5-nitro-2-vinylbenzene

A mixture of 1-bromo-2-chloro-5-fluoro-4-nitrobenzene (13.0 g, 49.24 mmol), $PdCl_2$(dppf).DCM (0.804 g, 0.98 mmol), potassium ethenyl(trifluoro)borate (7.88 g, 59.09 mmol) and triethylamine (6.87 mL, 49.24 mmol) in n-propanol (130 mL) was heated to reflux for 4 hours. The mixture was allowed to cool to room temperature and poured into water (500 mL). The mixture was extracted with DCM (2×300 mL) then the combined organic extracts were dried ($Na_2SO_4$) and the solvent removed under reduced pressure. The residue was purified by column chromatography on neutral silica gel using 1-2% ethyl acetate in hexane to give the title compound (7.8 g, 75%) as a white solid.

50D. 2-(2-chloro-5-methoxy-4-nitrophenyl)-N-(4-(4-methylpiperazin-1-yl)benzyl)ethanamine A mixture of 1-chloro-4-methoxy-5-nitro-2-vinylbenzene (0.42 g, 1.95 mmol), 4-(4-methyl-piperazin-1-yl)-benzylamine (1.2 g, 5.85 mmol) and quinol (0.043 g, 0.39 mmol) in n-butanol (8 mL) was heated to reflux for 12 hours under a $N_2$ atmosphere. Water (100 mL) was added and the reaction mixture extracted with EtOAc (3×100 mL). The combined organic extracts were washed with brine (50 mL), dried ($Na_2SO_4$) and concentrated under reduced pressure. The residue was purified by column chromatography on neutral silica gel using 3-5% methanol in DCM to give the title compound (0.35 g, 43%) as a solid.

50E. Tert-butyl-2-chloro-4-(3-(5-cyanopyrazin-2-yl)ureido)-5-methoxyphenethyl (4-(4-methylpiperazin-1-yl)benzyl)carbamate The title compound was prepared using the synthetic steps and chemistry described for the synthesis of examples 19G, 19H, 19I

50F. 1-(5-Chloro-2-methoxy-4-(2-(4-(4-methylpiperazin-1-yl)benzylamino)ethyl)phenyl)-3-(5-cyanopyrazin-2-yl)urea hydrochloride A 3 N HCl solution in 1,4-dioxane (10 mL) was added to a stirred solution of tert-butyl-2-chloro-4-(3-(5-cyanopyrazin-2-yl)ureido)-5-methoxyphenethyl(4-(4-methylpiperazin-1-yl)benzyl)carbamate (0.5 g) in acetonitrile (50 mL) at 5° C. The reaction mixture was allowed to warm to room temperature and stirring continued for 1 hour. Diethylether (150 ml) was added and the precipitated solid collected by filtration. The solid was triturated with diethylether, methanol, diethylether then dried at reduced pressure to yield the title compound (0.35 g, 70%) as a yellow solid.

Synthetic Route J
(Illustrated with reference to Example 56: 1-[4-(Benzylamino-methyl)-5-chloro-2-methoxy-phenyl]-3-(5-cyano-pyrazin-2-yl)-urea hydrochloride).

Example 56

56A. 1-chloro 4-methoxy-2-methyl-5-nitrobenzene

To a suspension of sodium hydride (1.2 mmol) in DMF (6 mL), 4-chloro 3-methyl 6-nitrophenol (1.0 mmol) was added at 0° C. The reaction mixture was stirred at 0° C. for 15 minute then methyliodide was added at 0° C. and the mixture was stirred for 4 hours at room temperature. Water (60 mL) was added and the mixture extracted with EtOAc (3×50 mL). The combined organic extracts were washed with water (50 mL), brine (50 mL), dried ($Na_2SO_4$) and concentrated under reduced pressure. The residue was purified by column chromatography on silica using 5-8% EtOAc in hexane to give the title compound (87%) as a solid.

56B. 2-chloro-5-methoxy-4-nitrobenzoic acid

A solution of 1-chloro-4-methoxy-2-methyl-5-nitrobenzene (1 mmol) and potassium permanganate (4 mmol) in water (100 mL) was heated at reflux temperature for 48 hours. The mixture was allowed to cool to room temperature and the pH was adjusted 2. The solution was extracted with EtOAc (2×100 mL), then the combined organic extracts was dried ($Na_2SO_4$) and concentrated under reduced pressure to give the title compound (78%) as a solid.

56C. Methyl 2-chloro-5-methoxy-4-nitrobenzoate

A solution of 2-chloro-5-methoxy-4-nitrobenzoic acid (1 mmol) and concentrated sulfuric acid (0.02 mmol) in methanol (200 mL) was heated to reflux for 42 hours. The solvents were evaporated under reduced pressure then the residue partitioned between EtOAc (25 mL) and water (25 mL). The separated aqueous phase was extracted with EtOAc (3×25 mL), then the combined organic extracts were dried ($Na_2SO_4$) and concentrated under reduced pressure to afford the title compound (71%) as a solid.

56D. (2-Chloro-5-methoxy-4-nitro-phenyl)-methanol

A 2M solution of $LiBH_4$ in THF (2 mmol) was added drop-wise to a stirred solution of methyl 2-chloro-5-methoxy-4-nitrobenzoate (1 mmol) in dry THF (10 mL) at 0° C. The mixture was allowed to warm to room temperature and stirred for 5 hours. EtOAc (10 mL) was added to the mixture followed by saturated $NH_4Cl$ solution (2 mL) and stirring continued for 15 minutes. The mixture was partitioned between EtOAc (10 mL) and water (10 mL) and the separated aqueous phase was extracted with EtOAc (10 mL). The combined organic extracts were dried ($Na_2SO_4$) and concentrated under reduced pressure to afford the title compound (89%) which was used without further purification.

56E. 1-[4-(Benzylamino-methyl)-5-chloro-2-methoxy-phenyl]-3-(5-cyano-pyrazin-2-yl)-urea hydrochloride The title compound was prepared using the synthetic steps and chemistry described for the synthesis of Examples 22A, 22B, 22C, 22D, 22E, 22F

56F. 1-[4-(Benzylamino-methyl)-5-chloro-2-methoxy-phenyl]-3-(5-cyano-pyrazin-2-yl)-urea hydrochloride A saturated solution of HCl in 1,4-dioxane (1.2 mmoL) was added to a solution of 1-(5-chloro-4-((4-fluorobenzylamino)methyl)-2-methoxyphenyl)-3-(5-cyanopyrazin-2-yl) urea (1 mmol) in DCM (50 mL) at 5° C. The reaction mixture was stirred at 5° C. for 2 hours then n-pentane (100 mL) was added and stirring continued for 15 minutes. The resulting solid was collected by filtration then washed with methanol (2×10 mL), followed by n-pentane (10 mL) and dried under reduced pressure to give the title compound (56%) as a white solid.

Example 34

1-(5-Cyano-pyrazin-2-yl)-3-{3-[2-(4-fluoro-benzylamino)-ethyl]-phenyl}-urea

34A. (E)-1-(2-methoxyvinyl)-3-nitrobenzene

A mixture of (methoxymethyl)triphenylphosphonium chloride (6.79 g, 19.85 mmol) in anhydrous THF (50 mL) was cooled to −20° C. and potassium tert-butoxide (2.67 g, 23.82 mmol) was added in lots to give a red reaction mass. The mixture was cooled to −30° C. and a solution of 3-nitrobenzaldehyde (2.0 g, 12.12 mmol) in toluene (15 mL) was added gradually over 30 minutes. The mixture was stirred for 1 hour then EtOAc (2 mL) followed by saturated ammonium chloride were added at 0° C. The reaction mixture was extracted with EtOAc (2×75 mL). The combined organic extracts were washed with brine (25 mL), dried ($Na_2SO_4$) and concentrated under reduced pressure. The crude compound was purified by column chromatography on neutral silica gel using DCM to afford the title compound (1.8 g, 76%) as a solid.

34B. 2-(3-nitrophenyl)acetaldehyde

To a solution of 1-(2-methoxyvinyl)-3-nitrobenzene (1.8 g, 10.06 mmol) in THF (60 mL), was added 6N HCl (6.03 mL) and the mixture was heated at 100° C. for 2 hours. The reaction mixture was allowed to cool to room temperature and the solvents were evaporated under reduced pressure to afford a solid. The solid was dissolved in EtOAc (45 mL) and water (50 mL) was added and the mixture stirred for 15 minutes. The separated aqueous phase was extracted with EtOAc (30 mL), and then the combined organic extracts were washed with 5% sodium bicarbonate (25 mL), brine (30 mL), dried ($Na_2SO_4$) and the solvents removed under reduced pressure. The crude compound was purified by column chromatography on neutral silica gel using 15-20% EtOAc in hexane to afford the title compound (1.2 g, 90%).

34C. N-(4-fluorobenzyl)-2-(3-nitrophenyl)ethanamine 2-(3-nitrophenyl)acetaldehyde (1.2 g, 7.33 mmol) was dissolved in methanol (50 mL) and 4-fluorobenzylamine (1.88 g, 14.67 mmol) was added at 15° C. followed by 1-2 drops of glacial acetic acid. The reaction was stirred at room temperature for 2 hours then sodium borohydride (0.14 g, 3.6 6 mmol) was added in lots at 0-10° C. and the solution allowed to warm to room temperature and stirred for a further 2 hours. The reaction mixture was poured into sodium bicarbonate solution (75 mL) and stirred for 15 minutes. The mixture was extracted with EtOAc (2×60 mL) then the combined organic extracts were washed with brine (50 mL) and dried ($Na_2SO_4$). The solvents were removed under reduced pressure to afford the crude compound which was purified by column chromatography on neutral silica gel using 1-2% methanol in DCM to afford the title compound (0.793 g, 40%).

34D. Tert-butyl 4-fluorobenzyl (3-nitrophenethyl)carbamate

To a solution of N-(4-fluorobenzyl)-2-(3-nitrophenyl) ethanamine (0.793 g, 2.89 mmol) in DCM (25 mL), triethylamine (0.584 g, 5.79 mmol) and Boc anhydride (0.757 g, 3.47 mmol) were added at room temperature and the mixture stirred for 1 hour. DCM (22 mL) and water (15 mL) were added and stirring continued for 15 minutes. The separated organic phase was washed with water (15 mL), dried ($Na_2SO_4$) and concentrated under reduced pressure to afford the title compound (0.9 g, 83%) which was used without further purification.

34E. Tert-butyl 3-aminophenethyl (4-fluorobenzyl)carbamate

To a solution of tert-butyl 4-fluorobenzyl (3-nitrophenethyl)carbamate (0.9 g, 2.41 mmol) in methanol (18 mL), a saturated solution of $NH_4Cl$ (18 mL) was added at room temperature. Zinc powder (0.784 g, 12.1 mmol) was added and the temperature was raised to 45° C. and the reaction mixture maintained at that temperature for 1 hour. The reaction mass was allowed to cool to room temperature and the solution was filtered through celite. EtOAc (60 mL) and water (100 mL) were added and stirring continued for a further 15 minutes. The separated aqueous phase was extracted with EtOAc (20 mL) and the combined organic extracts were washed with water (80 mL), brine (100 mL), dried ($Na_2SO_4$) and the solvents were removed under reduced pressure to afford the title compound (0.7 g, 86%) which was used without further purification.

34F. Tert-butyl-3-(3-(5-cyanopyrazin-2-yl)ureido) phenethyl(4-fluorobenzyl)carbamate A solution of tert-butyl-3-aminophenethyl(4-fluorobenzyl) carbamate (0.5 g, 1.45 mmol) and phenyl 5-cyanopyrazin-2-ylcarbamate (0.313 g, 1.30 mmol) in DMF (10 mL) was heated to 80° C. for 2 hours. The reaction was allowed to cool to room temperature then water (25 mL) and EtOAc (25 mL) were added and the mixture stirred for 15 minutes. The separated aqueous phase was extracted with EtOAc (25 mL), then the combined organic extracts were washed water (25 mL), brine (25 mL), dried ($Na_2SO_4$) and concentrated under reduced pressure. The residue was purified by column chromatography on neutral silica gel using 10-20% EtOAc in hexane to give the title compound (0.3 g, 42%).

34G. 1-(5-cyanopyrazin-2-yl)-3-(3-(2-(4-fluorobenzylamino)ethyl)phenyl)urea (TFA salt)

Tert-butyl-3-(3-(5-cyanopyrazin-2-yl)ureido)phenethyl-(4-fluorobenzyl)carbamate (0.3 g, 0.61 mmol) was dissolved in dichloromethane (20 mL) and the reaction mixture was cooled to 10° C. TFA (0.69 g, 6.11 mmol) was added to the stirred reaction mixture at 10° C. and maintained for 4 hours at 10° C. The solvents were removed under reduced pressure to afford the crude TFA salt. Hexane (8 mL) and EtOAc (2 mL) were added and the mixture stirred for 15 minutes. The solvent was decanted and the volatiles were removed under reduced pressure to afford the title compound (0.23 g, 75%) as a white solid.

34H. 1-(5-cyanopyrazin-2-yl)-3-(3-(2-(4-fluorobenzylamino)ethyl)phenyl)urea 1-(5-cyanopyrazin-2-yl)-3-(3-(2-(4-fluorobenzylamino) ethyl)phenyl)urea (TFA salt) (0.23 g, 0.46 mmol) was added in DCM (15 mL) and reaction mass was cooled to 0° C. 15% $NH_3$ in THF (0.3 mL) was added to the reaction mass at 0° C. and stirred for 1 hour at 0° C. The volatiles were removed under reduced pressure to afford crude final compound. Water (10 mL) and EtOAc (25 mL) were added and the mixture stirred for 15 minutes. The separated aqueous phase was extracted with EtOAc (25 mL), and then the combined organic extracts were washed with brine (15 mL) and the solvents removed under reduced pressure to afford the crude product. The residue was purified by solvent purification to give the title compound (100 mg, 56%) as a white solid.

Example 52

1-(5-Chloro-2-methoxy-4-{2-[(S)-1-(4-piperazin-1-yl-phenyl)-ethylamino]-ethyl}-phenyl)-3-(5-cyanopyrazin-2-yl)-urea hydrochloride

52A. [(S)-1-(4-Bromo-phenyl)-ethyl]-[2-(2-chloro-5-methoxy-4-nitro-phenyl)-ethyl]-amine A solution of (S)-1-(4-bromophenyl)ethylamine (0.94 g, 4.69 mmol), 1-chloro-4-methoxy-5-nitro-2-vinylbenzene (Example 50C) (0.5 g, 2.34 mmol) and quinol (0.1 g, 0.94 mmol) in n-butanol (6 mL) was heated to reflux for 18 hours. The reaction mixture was concentrated under reduced pressure then the residue partitioned between EtOAc (40 mL) and water (30 mL). The separated aqueous phase was extracted with EtOAc (3×40 mL), and then the combined organic extracts were washed with brine, dried ($Na_2SO_4$) and concentrated under reduced pressure. The crude product was purified by column chromatography on silica gel using 0-1% MeOH in DCM to give the title compound (0.55 g, 57%).

52B. [(S)-1-(4-Bromo-phenyl)-ethyl]-[2-(2-chloro-5-methoxy-4-nitro-phenyl)-ethyl]-carbamic acid tert-butyl ester To a solution of [(S)-1-(4-bromo-phenyl)-ethyl]-[2-(2-chloro-5-methoxy-4-nitro-phenyl)-ethyl]-amine (0.55 g, 1.33 mmol) in DCM (6 mL), triethylamine (0.56 mL, 4.0 mmol) and BOC anhydride (0.436 g, 2.0 mmol) were added at room temperature and mixture was stirred for 6 hours. After completion of reaction, DCM (30 mL) and water (30 mL) were added and stirring continued for 15 minutes. The separated and organic phase was washed with water (2×20 mL), dried ($Na_2SO_4$) and concentrated under reduced pressure to give the title compound (0.66 g, 97%).

52C. 4-[4-((S)-1-{tert-Butoxycarbonyl-[2-(2-chloro-5-methoxy-4-nitro-phenyl)-ethyl]-amino}-ethyl)-phenyl]-piperazine-1-carboxylic acid tert-butyl ester A solution of [(S)-1-(4-bromo-phenyl)-ethyl]-[2-(2-chloro-5-methoxy-4-nitro-phenyl)-ethyl]-carbamic acid tert-butyl ester (0.66 g, 1.17 mmol), N-Boc piperazine (0.44 g, 2.34 mmol), cesium carbonate (0.96 g, 2.92 mmol) and devphos (46.1 mg, 0.117 mmol) in 1,4-dioxane (5 mL) was degassed with argon. $Pd_2(dba)_3$ (0.054 g, 0.058 mmol) was added and the mixture heated to reflux for 3 hours under an argon atmosphere. The mixture was allowed to cool to room temperature, diluted with water (30 mL) and extracted with EtOAc (3×30 mL). The combined organic extracts were washed with brine, dried ($Na_2SO_4$) and concentrated under reduced pressure. The residue was purified by column chromatography on silica gel using 20% EtOAc in hexane to give the title compound (0.33 g, 46%).

52D. 4-[4-((S)-1-{[2-(4-Amino-2-chloro-5-methoxyphenyl)-ethyl]-tert-butoxycarbonyl-amino}-ethyl)-phenyl]-piperazine-1-carboxylic acid tert-butyl ester To a solution of 4-[4-((S)-1-{tert-butoxycarbonyl-[2-(2-chloro-5-methoxy-4-nitro-phenyl)-ethyl]amino}-ethyl)phenyl]-piperazine-1-carboxylic acid tert-butyl ester (0.32 g, 0.53 mmol) in methanol (12 mL), a saturated solution of $NH_4Cl$ (8 mL) and zinc powder (0.175 g, 2.66 mmol) were added at room temperature and the reaction was stirred at 80° C. for 2 hours. The mixture was allowed to cool to room temperature and then filtered through cotton wool. Water (50 mL) was added and the mixture extracted with EtOAc (2×30 mL). The combined organic extracts were washed with brine (20 mL), dried ($Na_2SO_4$) and concentrated under reduced pressure to give the title compound (0.28 g, 89%) which was used without further purification.

52E. 4-(4-{(S)-1-[tert-Butoxycarbonyl-(2-{2-chloro-4-[3-(5-cyano-pyrazin-2-yl)-ureido]-5-methoxyphenyl}-ethyl)-amino]-ethyl}-phenyl)-piperazine-1-carboxylic acid tert-butyl ester A stirred solution of 4-[4-((S)-1-{[2-(4-amino-2-chloro-5-methoxy-phenyl)-ethyl]-tert-butoxycarbonyl-amino}ethyl)-phenyl]piperazine-1-carboxylic acid tert-butyl ester (0.28 g, 0.475 mmol) and phenyl 5-cyanopyrazin-2-ylcarbamate (0.091 g, 0.38 mmol) in DMF (18 mL) was heated to 100° C. for 1 hour. The mixture was allowed to cool to room temperature, diluted with water (50 mL) and extracted with EtOAc (2×40 mL). The combined organic extracts were washed with water (3×40 mL), brine (40 mL), dried ($Na_2SO_4$) and concentrated under reduced pressure. The residue was purified with column chromatography on neutral silica gel using 25% EtOAc in hexane to give the title compound (0.16 g, 46%).

52F. 1-(5-Chloro-2-methoxy-4-{2-[(S)-1-(4-piperazin-1-yl-phenyl)-ethylamino]-ethyl}-phenyl)-3-(5-cyano-pyrazin-2-yl)-urea dihydrochloride A 4N HCl solution in EtOAc (18 mL) was added slowly to a stirred solution of 4-(4-{(S)-1-[tert-butoxycarbonyl-(2-{2-chloro-4-[3-(5-cyano-pyrazin-2-yl)-ureido]-5-methoxyphenyl}-ethyl)-amino]ethyl}-phenyl)-piperazine-1-carboxylic acid tert-butyl ester (0.1 g) in EtOAc (100 mL) at 0° C. The mixture was allowed to warm to room temperature and stirred for 8 hours. Diethyl ether (50 mL) was added and stirring continued for 15 minutes. The supernatant was decanted and the isolated solid triturated again with diethyl ether (50 mL). The solid was dried under reduced pressure then dissolved in methanol and precipitated back out of solution using diethyl ether. The isolated solid was further triturated with diethyl ether then dried under reduced pressure. The obtained solid was triturated with ethyl acetate, acetone, ethanol followed by diethyl ether and dried at reduced pressure to give the title compound (0.025 g, 34%) as a white solid.

Example 64

1-{5-Chloro-2-methoxy-4-[2-(4-piperazin-1-yl-benzylamino)-ethyl]-phenyl}-3-(5-cyano-pyrazin-2-yl)-urea hydrochloride

64A. Tert-butyl 4-(4-((2-chloro-5-methoxy-4-nitro-phenethylamino)methyl)phenyl)piperazine-1-carboxylate A stirred solution of 4-(4-aminomethyl-phenyl)-piperazine-1-carboxylic acid tert-butyl ester (0.531 g, 1.82 mmol), 1-chloro-4-methoxy-5-nitro-2-vinylbenzene (Example 50C) (0.3 g, 1.40 mmol) and quinol (61.8 mg, 0.562 mmol) in isopropyl alcohol (16 mL) was heated to 100° C. for 30 hours. The mixture was allowed to cool to room temperature and concentrated under reduced pressure. The residue was purified by column chromatography on neutral silica gel using 2% methanol in DCM to give the title compound (0.460 g, 65%)

64B. Tert-butyl 4-(4-(((tert-butoxycarbonyl (2-chloro-5-methoxy-4-nitrophenethyl)amino)methyl)phenyl)piperazine-1-carboxylate To a solution of tert-butyl 4-(4-((2-chloro-5-methoxy-4-nitrophenethylamino)methyl)phenyl)piperazine-1-carboxylate (0.460 g, 0.91 mmol) in DCM (10 mL), triethylamine (0.380 mL, 2.75 mmol) and BOC anhydride (0.3 g, 1.37 mmol) were added at room temperature and the mixture stirred for 1 hour. After completion of reaction, DCM (10 mL) and water (20 mL) were added and stirring continued for 15 minutes. The separated organic phase was washed with water (2×30 mL), dried (Na$_2$SO$_4$) and concentrated under reduced pressure. The residue was purified column chromatography on neutral silica gel using 30% EtOAc in hexane to give the title compound (0.480 g, 86%).

64C. Tert-butyl-4-(4-(((4-amino-2-chloro-5-methoxyphenethyl)(tert-butoxycarbonyl)amino)methyl)phenyl)piperazine-1-carboxylate To a solution of tert-butyl 4-(4-((tert-butoxycarbonyl (2-chloro-5-methoxy-4-nitrophenethyl)amino)methyl)phenyl)piperazine-1-carboxylate (0.480 g, 0.793 mmol) in methanol (15 mL), a saturated solution of NH$_4$Cl (10 mL) and zinc powder (0.257 g, 3.96 mmol) were added at room temperature and the reaction stirred at 70-80° C. for 1 hour. The mixture was allowed to cool to room temperature and filtered through a celite pad. Water (40 mL) was added to the filtrate and the mixture extracted with EtOAc (2×30 mL). The combined organic extracts were washed with brine (10 mL), dried (Na$_2$SO$_4$) and concentrated under reduced pressure to give the title compound (0.440 g, 97%).

64D. Tert-butyl 4-(4-((tert-butoxycarbonyl (2-chloro-4-(3-(5-cyanopyrazin-2-yl) ureido)-5-methoxy-phenethyl)amino)methyl)phenyl)piperazine-1-carboxylate A stirred solution of tert-butyl-4-(4-(((4-amino-2-chloro-5-methoxyphenethyl)(tert-butoxycarbonyl)amino)methyl)phenyl)piperazine-1-carboxylate (0.46 g, 0.800 mmol) and phenyl 5-cyanopyrazin-2-ylcarbamate (0.153 g, 0.64 mmol) in DMF (18 mL) was heated to 100° C. for 1.5 hours. The mixture was allowed to cool to room temperature, diluted with water (40 mL) and extracted with EtOAc (2×30 mL). The combined organic extracts were washed with water (3×15 mL), brine (10 mL), dried (Na$_2$SO$_4$) and concentrated under reduced pressure. The residue was purified with column chromatography on neutral silica gel using 1.5% methanol in DCM to give the title compound (0.25 g, 43%).

64E. 1-(5-chloro-2-methoxy-4-(2-(4-(piperazin-1-yl) benzylamino)ethyl)phenyl)-3-(5-cyanopyrazin-2-yl) urea dihydrochloride A 3 N HCl solution in 1,4-dioxane (0.4 mL) was slowly added to a solution of tert-butyl 4-(4-((tert-butoxycarbonyl (2-chloro-4-(3-(5-cyanopyrazin-2-yl)ureido)-5-methoxy-phenethyl)amino)methyl)phenyl)piperazine-1-carboxylate (0.1 g) in acetonitrile (5 mL) at 0° C. The mixture was allowed to warm to room temperature and then stirring continued for one hour. Diethyl ether (25 mL) was added and after stirring continued for 15 minutes then the supernatant was decanted and the resulting solid was triturated with diethyl ether (25 mL) and dried under reduced pressure to yield a yellow solid. The solid was further triturated with methanol followed by diethyl ether and dried under reduced pressure to give the title compound (0.05 g, 60%) as an off-white solid.

BIOLOGICAL ACTIVITY

Example 66

Chk-1 Kinase Inhibiting Activity

The compounds of the invention were tested for activity against Chk-1 kinase using the materials and protocols set out below.
Reaction Buffer:
Base Reaction buffer: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO
*Required cofactors are added individually to each kinase reaction
Reaction Procedure:
(i) Prepare indicated substrate in freshly prepared Base Reaction Buffer
(ii) Deliver any required cofactors to the substrate solution above
(iii) Deliver indicated kinase into the substrate solution and gently mix
(iv) Deliver compounds in DMSO into the kinase reaction mixture
(v) Deliver $^{33}$P-ATP (specific activity 0.01 μCi/μl final) into the reaction mixture to initiate the reaction.
(vi) Incubate kinase reaction for 120 minutes at room temperature
(vii) Reactions are spotted onto P81 ion exchange paper (Whatman #3698-915)
(viii) Wash filters extensively in 0.1% phosphoric acid.
(ix) Dry filters and measure counts in scintillation counter
Kinase Information:
CHK-1—Genbank Accession #AF016582
Recombinant full length construct, N-terminal GST tagged, purified from insect cells.
No special measures were taken to activate this kinase.
Final concentration in assay=0.5 nM Substrate: CHKtide
Peptide sequence: [KKKVSRSGLYRSPSMPENLNRPR]
Final concentration in assay=20 μM
No additional cofactors are added to the reaction mixture From the results obtained by following the above protocol, the $IC_{50}$ values against Chk-1 kinase of each of the compounds of Examples 1 to 65 were determined.

The compounds of Examples 1 to 64 all had $IC_{50}$ values of less than 1 μM. Of these, the compounds of Examples 9, 15, 19, 20, 21, 30, 31, 33, 35, 37, 38, 40, 42, 43, 44, 45, 46, 47, 48, 49, 50, 51, 52, 53, 54, 55, 56, 57, 60, 61, 62, 63, 64 and 65 all had $IC_{50}$ values of less than 0.01 μM. The compounds of Examples 2, 4, 5, 6, 7, 8, 10, 12, 13, 14, 16, 17, 18, 22, 23, 24, 25, 26, 27 and 28 all had $IC_{50}$ values in the range from 0.01 to 0.1 μM, and the compounds of Examples 1, 3, 11 and 29 all had $IC_{50}$ values in the range from 0.1 to 1 μM.

The compounds of each of Examples 1 to 65 have the $IC_{50}$ values shown in Table 3.

TABLE 3

| Example | $IC_{50}$ (μM) |
|---|---|
| 1 | 0.200 |
| 2 | 0.044 |
| 3 | 0.179 |
| 4 | 0.015 |
| 5 | 0.038 |
| 6 | 0.026 |
| 7 | 0.016 |
| 8 | 0.011 |
| 9 | 0.002 |
| 10 | 0.062 |
| 11 | 0.146 |
| 12 | 0.011 |
| 13 | 0.037 |
| 14 | 0.068 |
| 15 | 0.0035 |
| 16 | 0.013 |
| 17 | 0.078 |
| 18 | 0.021 |
| 19 | 0.0012 |
| 20 | 0.0028 |
| 21 | 0.0041 |
| 22 | 0.099 |
| 23 | 0.011 |
| 24 | 0.013 |
| 25 | 0.018 |
| 26 | 0.021 |
| 27 | 0.033 |
| 28 | 0.047 |
| 29 | 0.320 |
| 30 | 0.0064 |
| 31 | 0.0027 |
| 32 | 0.027 |
| 33 | 0.0030 |
| 34 | 0.069 |
| 35 | 0.0014 |
| 36 | 0.010 |
| 37 | 0.0016 |
| 38 | 0.0091 |
| 39 | 0.012 |
| 40 | 0.0079 |
| 41 | 0.019 |
| 42 | 0.00045 |
| 43 | 0.0033 |
| 44 | 0.0051 |
| 45 | 0.0012 |
| 46 | 0.00032 |
| 47 | 0.0084 |
| 48 | 0.00047 |
| 49 | 0.00028 |
| 50 | 0.00045 |
| 51 | 0.0033 |
| 52 | 0.00013 |
| 53 | 0.00056 |
| 54 | 0.00023 |
| 55 | 0.00048 |
| 56 | 0.0028 |
| 57 | 0.0089 |
| 58 | 0.021 |
| 59 | 0.013 |
| 60 | 0.0016 |
| 61 | 0.0075 |
| 62 | 0.0078 |
| 63 | 0.0098 |
| 64 | 0.00003 |
| 65 | 0.00073 |

Sensitisation of Cancer Cells to the DNA Damaging Effects of Anti-Cancer Drugs

Many anti-cancer drugs achieve their anti-cancer effects by causing DNA damage but resistance to such drugs can be a significant problem. One mechanism responsible for drug resistance is the prevention of cell cycle progression through the control of critical activation of a checkpoint pathway which arrests the cell cycle to provide time for repair, and induces the transcription of genes to facilitate repair, thereby avoiding immediate cell death. Chk-1 kinase is involved in controlling checkpoint arrests and, by inhibiting the activity of Chk-1, it should be possible to prevent checkpoint arrests, thereby enhancing the action of DNA damaging agents by allowing mitosis to occur before DNA repair is complete.

The following are non-limiting examples of cancer cells with either p53 gene deletions or p53 gene mutations.

| Cancer cell line | Type |
|---|---|
| MDA-MB-231 | Breast |
| SW620 | Colon |
| HT29 | Colon |
| HL60 | Colon |
| Colo205 | Colon |
| DLD-1 | Colon |
| U373MG | Glioma |
| K562 | Leukaemia |
| Calu-6 | Lung |
| H322 | Lung |
| NCI-H1299 | Lung |
| Skov-3 | Ovarian |
| Panc-1 | Pancreatic |
| MIA PaCa-2 | Pancreatic |
| DU-145 | Prostate |
| PC-3 | Prostate |

Example 67

Studies were carried out to test the sensitising effect of compounds of the invention on the ability of the DNA damaging compound 7-ethyl-10-hydroxycamptothecin (SN38), an active metabolite of the anti-cancer drug irinotecan, to inhibit cell growth in HT29 cells.

The following protocol was used:
(a) HT29 cells were seeded in 96-well plates at a concentration of 3000 cells per well and allowed to adhere overnight prior to addition of compound or vehicle control.
(b) SN38 was prepared from a 10 mM DMSO stock to give a final concentration range of 1 μM, 300 nM, 100 nM, 30 nM, 10 nM, 3 nM, 1 nM, and vehicle control.
(c) Test compounds were prepared from 10 mM DMSO stocks to typically give a final concentration range of 3 μM, 1 μM, 0.3 μM. 0.1 μM, 0.03 μM and vehicle control. The final DMSO content was 0.4%.

(d) Test compounds were incubated with the cells for 72 h at 37° C. 5% $CO_2$ in a humidified atmosphere.
(e) Alamar blue 10% (v/v) was then added and incubated for a further 6 h, and fluorescent product detected using the BMG FLUOstar plate reader.
(f) Data were analysed using a 4-parameter logistic equation in GraphPad Prism.

Sensitisation is determined by the enhancement in $IC_{50}$ of SN38 by the addition of the Chk-1 kinase inhibitor. In the protocol described above, the $IC_{50}$ for SN-38 is determined the presence of varying doses of the Chk-1 inhibitor. The fold shift represents a decrease in $IC_{50}$ for SN-38 at a dose of Chk-1 inhibitor that has no effect by itself.

Each of the compounds of Examples 1, 2, 3, 4, 5, 6, 8, 9, 10, 11, 12, 14, 15, 20, 22, 23, 26, 27, 31, 33, 34, 38, 39, 40 and 60 produced at least a three fold shift in the $IC_{50}$ value of SN38 at a concentration of 3 μM or, in the case of Example 4, 1.25 μM. The compounds of each of Examples 7, 13, 16, 17, 18, 35, 37, 42, 48, 49, 50 and 57 produced at least a two fold shift in the $IC_{50}$ value of SN38 at a concentration of 1 μM. The compound of Example 29 produced a four fold shift in the $IC_{50}$ value of SN38 at a concentration of 10 μM. The compounds of Examples 8, 9, 12, 15, 20, 22, 23, 37, 42, 48, 49, 57 and 60 produced a greater than ten fold shift in the $IC_{50}$ value of SN38 at concentrations of 3 μM.

The results demonstrate that the compounds of this invention can sensitise HT29 cell cultures to the DNA damage induced by the action of SN-38. This sensitisation is in line with a mechanism involving Chk-1 inhibition leading to G2/M abrogation and sensitisation of p53 compromised cells. Although the sensitising action of the compounds of the invention has been exemplified using HT29 cells, it is not limited to this cell type and it is envisaged that other cell types (e.g. p53 compromised cell types) will also be sensitised to DNA damaging agents by the compounds of the invention. Examples of such cell types include Colo205, SKMel28, H322, OvCar3, MDA MB231 & U373MG.

Example 68

Sensitisation of Cancer Cells to the DNA Damaging Effects of Etoposide, Gemcitabine and SN-38

Using the general protocol set out in Example 67, the compound of Example 4 was tested in potentiation assays against a variety of cell lines in combination with several different DNA damaging anti-cancer agents. The results are set out in the table below.

| Cell Line | Cancer Type | DNA-Damaging Agent | Potentiation factor | Concentration of compound of Example 4 (μM) |
|---|---|---|---|---|
| Calu 6 | human lung adenocarcinoma | etoposide | 7.6 | 8 |
| SW620 | human colon adenocarcinoma | etoposide | 2.6 | 1 |
| Calu 6 | human lung adenocarcinoma | gemcitabine | 6.1 | 8 |
| SW620 | human colon adenocarcinoma | gemcitabine | 2.5 | 2 |
| HT29 | human colon cancer | gemcitabine | 18 | 4 |
| Calu 6 | human lung adenocarcinoma | SN-38 | 3.7 | 8 |
| SW620 | human colon adenocarcinoma | SN-38 | 16.4 | 4 |

Example 69

Studies were carried out to test the effect of compounds on the inhibition of cell growth in MOLM-13 and MV4-11 cells.
The following protocol was used:
(a) Cells were seeded in 96-well plates at cell densities of 2500/well (MOLM-13) and 10,000/well (MV4-11). Cells were then incubated overnight prior to addition of compound or vehicle control.
(b) Test compounds were prepared from 10 mM DMSO stocks to give a final concentration range of 10 μM, 3 μM, 1 μM, 0.3 μM, 0.1 μM, 0.03 μM, 0.01 μM, 0.03 μM, 0.01 μM and vehicle control. The DMSO content was constant at 0.1%.
(c) Test compounds were incubated with the cells for 72 h at 37° C. 5% $CO_2$ in a humidified atmosphere.
(d) Alamar blue 10% (v/v) was then added and incubated for a further 4 h, and fluorescent product detected using the BMG FLUOstar plate reader.
(e) Media only background values were subtracted and the data analysed using a 4-parameter logistic equation in GraphPad Prism.

From the results obtained by following the above protocol, the $IC_{50}$ values against MOLM-13 and MV4-11 cells of the compounds of Examples 20, 21, 22, 25, 33, 35, 37, 38, 44, 48, 49, 50, 51, 53, 54 and 55 were determined.

The compounds of each of selected have $IC_{50}$ values shown in Table 4.

TABLE 4

| Example | MOLM-13 $IC_{50}$ (μM) | MV4-11 $IC_{50}$ (μM) |
|---|---|---|
| 20 | 0.500 | 0.810 |
| 21 | 1.30 | 1.29 |
| 22 | >3.0 | >3.0 |
| 25 | 1.79 | 1.71 |
| 33 | 1.3 | 1.29 |
| 35 | 1.3 | 3.9 |
| 37 | 0.57 | 1.0 |
| 38 | 0.61 | 2.44 |
| 44 | 0.85 | 0.96 |
| 48 | 0.100 | 0.190 |
| 49 | 0.060 | 0.120 |
| 50 | 0.070 | 0.310 |
| 51 | 0.240 | 0.860 |
| 53 | 0.030 | 0.288 |
| 54 | 0.014 | 0.052 |
| 55 | 0.034 | 0.254 |

Example 70

Comparative Tests (i) Effect of Replacing a Methylpyrazinyl Group with a Cyanopyrazinyl Group
WO 02/070494 (Icos) discloses a class of diarylurea Chk-1 kinase inhibitors. Compound 338 in WO 02/070494 has the following structure:

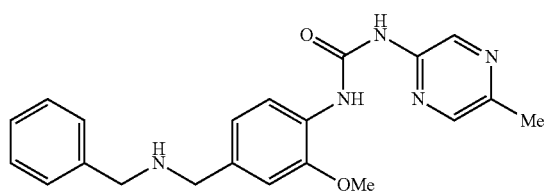 [SMILES: COc1cc(CNCc2ccccc2)ccc1NC(=O)Nc1cnc(C)cn1]

The compounds of the present invention have been tested against Compound 338 in both the Chk-1 kinase assay and the SN38 sensitisation assay in HT-29 cells described above. A comparison of the effect of replacing the methylpyrazinyl ring of Compound 33 with a cyanopyrazinyl ring according to the present invention is shown in the table below.

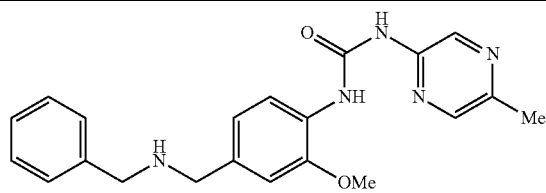

Compound 338 (WO02/070494)
Chk-1 $IC_{50}$ = 0.099 μM
Cell potentiation factor: 5 fold at 3 μM

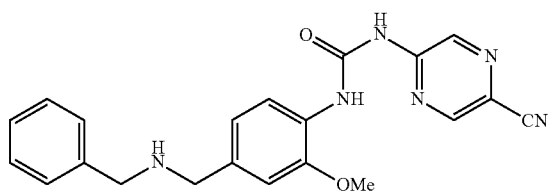 [SMILES: COc1cc(CNCc2ccccc2)ccc1NC(=O)Nc1cnc(C#N)cn1]

Example 19
Chk-1 $IC_{50}$ = 0.008 μM
Cell potentiation factor: 50 fold at 3 μM

The data illustrate that changing the methyl group for a cyano group results in an approximately 12 fold improvement in potency against the Chk-1 enzyme and a 10 fold improvement in cell potentiation at the same concentration of Chk-1 inhibitor compound.

(ii) Effect of Increasing the Chain Length of the Arylaminoalkyl Side Chain

Compound 338 of WO02/070494 has a benzylaminomethyl side chain. It has been found that extending the side chain by one or more carbon atoms results in a substantial and unexpected increase in activity, as illustrated in the table below.

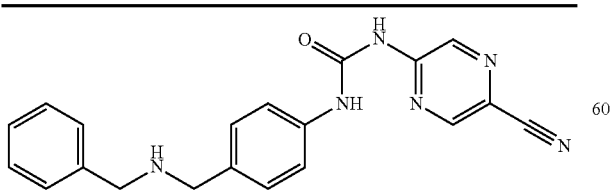

Example 30
Chk-1 $IC_{50}$ = 0.320 μM
Cell potentiation factor: 4 fold at 10 μM

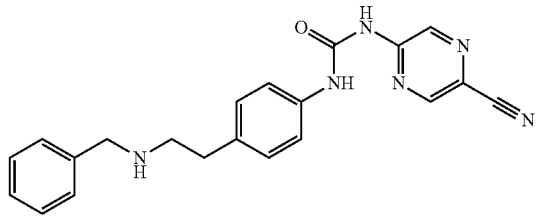 [SMILES: N#Cc1cnc(NC(=O)Nc2ccc(CCNCc3ccccc3)cc2)cn1]

Example 1
Chk-1 $IC_{50}$ = 0.099 μM
Cell potentiation factor: 4 fold at 3 μM

The data for Example 30 and Example 1 show that increasing the length of the alkylene chain between the central benzene ring and the amino group from 1 to 2 carbon atoms gives approximately a 3 fold improvement in potency against Chk-1 enzyme and the same cell potentiation at a lower concentration of inhibitor.

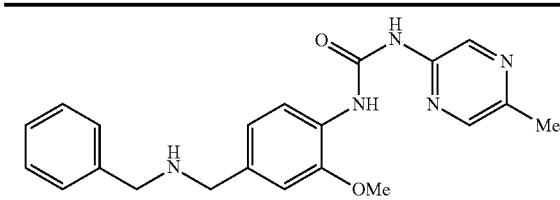

Compound 338 (WO02/070494)
Chk-1 $IC_{50}$ = 0.099 μM

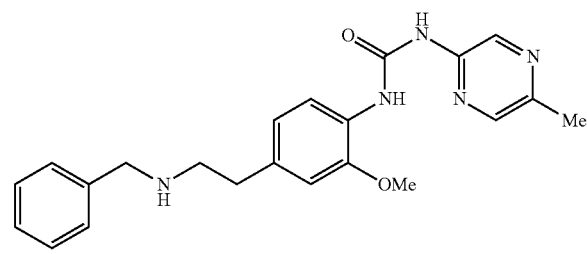 [SMILES: COc1cc(CCNCc2ccccc2)ccc1NC(=O)Nc1cnc(C)cn1]

Example 32
Chk-1 $IC_{50}$ = 0.027 μM

The data for Compound 338 of WO02/070494 and Example 32 of the present application show that increasing the length of the alkylene chain between the central benzene ring and the amino group from 1 to 2 carbon atoms gives approximately a 3 fold improvement in potency against Chk-1.

Example 71

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

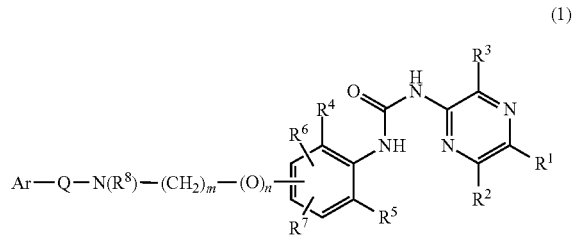

(1)

or a salt, N-oxide or tautomer thereof,
wherein $R^1$ is cyano or $C_{1-4}$ alkyl;
$R^2$ is hydrogen or $C_{1-4}$ alkyl;
$R^3$ is hydrogen or $C_{1-4}$ alkyl;
$R^4$ and $R^5$ are the same or different and each is selected from hydrogen, saturated $C_{1-4}$ hydrocarbyl and saturated $C_{1-4}$ hydrocarbyloxy;
$R^6$ and $R^7$ are the same or different and each is selected from hydrogen, halogen, CN, $C_{1-4}$ alkyl and $C_{1-4}$ alkoxy wherein the $C_{1-4}$ alkyl and $C_{1-4}$ alkoxy are each optionally substituted with hydroxy, $C_{1-2}$ alkoxy or by one or more flourine atoms;
$R^8$ is hydrogen or $C_{1-4}$ alkyl;
Q is an alkylene chain of 1 to 4 carbon atoms in length between the moiety Ar and the nitrogen atom N, wherein one or more of the 1 to 4 carbon atoms of the alkylene chain may optionally be substituted with one or two $C_{1-4}$ alkyl groups, or wherein one carbon atom of the 1 to 4 carbon atoms of the alkylene chain may optionally be substituted with a group —$CH_2CH_2$— which together with the said one carbon atom forms a cyclopropyl group;
m is 1, 2, 3 or 4;
n is 0 or 1; and
Ar is a monocyclic or bicyclic aryl or heteroaryl group of 5 to 10 ring members containing 0, 1, 2, 3 or 4 heteroatom ring members selected from O, N and S, the aryl or heteroaryl group being optionally substituted with one to four substituents $R^{13}$ which are the same or different;
$R^{13}$ is selected from:
halogen;
cyano;
nitro;
a carbocyclic or heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; and
a group $R^a$-$R^b$;
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;
$R^b$ is:
hydrogen;
a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; wherein one or more but not all of the carbon atoms of the acyclic $C_{1-12}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is:
hydrogen;
a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; wherein one or more but not all of the carbon atoms of the acyclic $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, $N(C_{1-4}$ alkyl)C(O), $C(O)N(C_{1-4}$ alkyl)
$X^1$ is O, S or $NR^c$; and
$X^2$ is =O, =S or =$NR^c$;
wherein $R^{14}$ is selected from $R^{13}$ provided that when the substituents $R^{14}$ contain a carbocyclic or heterocyclic group, the said carbocyclic or heterocyclic group is unsubstituted or substituted with one or more substituents $R^{15}$; and
$R^{15}$ is selected from $R^{13}$ except that any carbocyclic or heterocyclic groups constituting or forming part of $R^{15}$ may not bear a substituent containing or consisting of a carbocyclic or heterocyclic group;
provided that when m is 1, n is O and $R^1$ is cyano.

2. A compound according to claim 1 of the formula (1):

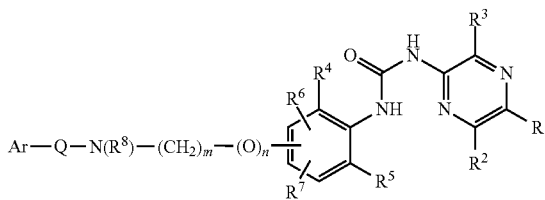

(1)

or a salt, N-oxide or tautomer thereof,
wherein $R^1$ is cyano or $C_{1-4}$ alkyl;
$R^2$ is hydrogen or $C_{1-4}$ alkyl;
$R^3$ is hydrogen or $C_{1-4}$ alkyl;
$R^4$ and $R^5$ are the same or different and each is selected from hydrogen, $C_{1-4}$ alkyl and $C_{1-4}$ alkoxy;
$R^6$ and $R^7$ are the same or different and each is selected from hydrogen, halogen, CN, $C_{1-4}$ alkyl and $C_{1-4}$ alkoxy wherein the $C_{1-4}$ alkyl and $C_{1-4}$ alkoxy are each optionally substituted with hydroxy, $C_{1-2}$ alkoxy or by one or more flourine atoms;

$R^8$ is hydrogen or $C_{1-4}$ alkyl;
Q is an alkylene chain of 1 to 4 carbon atoms in length between the moiety Ar and the nitrogen atom N, wherein one or more of the 1 to 4 carbon atoms of the alkylene chain may optionally be substituted with one or two methyl groups;
m is 1, 2 or 3;
n is 0 or 1; and
Ar is a monocyclic or bicyclic aryl or heteroaryl group of 5 to 10 ring members containing 0, 1, 2, 3 or 4 heteroatom ring members selected from O, N and S, the aryl or heteroaryl group being optionally substituted with one to four substituents $R^{13}$ which are the same or different;
$R^{13}$ is selected from:
halogen;
cyano;
nitro;
a carbocyclic or heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; and
a group $R^a$-$R^b$;
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;
$R^b$ is:
hydrogen;
a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; wherein one or more but not all of the carbon atoms of the $C_{1-12}$ acyclic hydrocarbyl group may optionally be replaced by O, S, SO, $SO_2$, $NR^c$, $X^1C(X^2)$, $C(X^2)X^1$ or $X^1C(X^2)X^1$;

$R^c$ is:
hydrogen;
a carbocyclic and heterocyclic group having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$;
an acyclic $C_{1-12}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 12 ring members, of which 0, 1, 2, 3 or 4 are heteroatom ring members selected from O, N and S and oxidised forms thereof, the carbocyclic or heterocyclic group being optionally substituted with one or more substituents $R^{14}$; wherein one or more but not all of the carbon atoms of the $C_{1-12}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$ alkyl)C(O), C(O)N($C_{1-4}$ alkyl)

$X^1$ is O, S or $NR^c$; and $X^2$ is =O, =S or =$NR^c$;

wherein $R^{14}$ is selected from $R^{13}$ provided that when the substituents $R^{14}$ contain a carbocyclic or heterocyclic group, the said carbocyclic or heterocyclic group is unsubstituted or substituted with one or more substituents $R^{15}$; and $R^{15}$ is selected from $R^{13}$ except that any carbocyclic or heterocyclic groups constituting or forming part of $R^{15}$ may not bear a substituent containing or consisting of a carbocyclic or heterocyclic group;

provided that when m is 1, n is O and $R^1$ is cyano.

3. A compound according to claim 1, or a salt, N-oxide or tautomer thereof, wherein Ar is selected from optionally substituted phenyl and optionally substituted five and six membered heteroaryl groups containing one, two or three heteroatom ring members selected from O, N and S.

4. A compound according to claim 3, or a salt, N-oxide or tautomer thereof, wherein Ar is optionally substituted phenyl.

5. A compound according to claim 1, or a salt, N-oxide or tautomer thereof, wherein each $R^{13}$ is independently selected from a group $R^{13a}$ consisting of halogen; cyano; nitro; a monocyclic carbocyclic or heterocyclic group having from 3 to 10 ring members, of which 0, 1, 2, 3 or 4 are heteroatom ring members selected from O, N and S and oxidised forms thereof, the carbocyclic or heterocyclic group being and optionally substituted with one or more substituents $R^{14a}$; or a group $R^{a1}$-$R^{b1}$;

$R^{a1}$ is a bond, O, CO, $X^{1a}C(X^{2a})$, $C(X^{2a})X^{1a}$, $X^{1a}C(X^{2a})X^{1a}$, S, SO, $SO_2$, $NR^{c1}$, $SO_2NR^{c1}$ or $NR^{c1}SO_2$;

$R^{b1}$ is:

hydrogen;

a carbocyclic and heterocyclic group having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$;

an acyclic $C_{1-8}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and monocyclic carbocyclic and heterocyclic groups having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$; wherein one or more carbon atoms of the acyclic $C_{1-8}$ hydrocarbyl group may optionally be replaced by O, S, SO, $SO_2$, $NR^{c1}$, $X^{1a}C(X^{2a})$, $C(X^{2a})X^{1a}$ or $X^{1a}C(X^{2a})X^{1a}$;

$R^{c1}$ is:

hydrogen;

a carbocyclic and heterocyclic group having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$;

an acyclic $C_{1-8}$ hydrocarbyl group optionally substituted with one or more substituents selected from hydroxy; oxo; halogen; cyano; nitro; carboxy; amino; mono- or di-$C_{1-8}$ non-aromatic hydrocarbylamino; and carbocyclic and heterocyclic groups having from 3 to 10 ring members, of which 0, 1, 2, 3 or 4 are heteroatom ring members selected from O, N and S and oxidised forms thereof, the carbocyclic or heterocyclic group being optionally substituted with one or more substituents $R^{14a}$; wherein one or more but not all of the carbon atoms of the acyclic $C_{1-8}$ hydrocarbyl group may optionally be replaced by O, S, SO, $SO_2$, NH, N—$C_{1-4}$ alkyl, C(O)O, OC(O), NH(CO), C(O)NH, NH(CO)NH, N($C_{1-4}$ alkyl)C(O), C(O)N($C_{1-4}$ alkyl)

$X^{1a}$ is O, S or $NR^{c1}$; and $X^{2a}$ is =O, =S or =$NR^{c1}$;

wherein $R^{14a}$ is selected from $R^{13a}$ provided that when the substituents $R^{14a}$ contain a monocyclic carbocyclic or heterocyclic group having from 3 to 10 ring members, the said carbocyclic or heterocyclic group is unsubstituted or substituted with one or more substituents $R^{15a}$; and $R^{15a}$ is selected from $R^{13a}$ except that any carbocyclic or heterocyclic groups constituting or forming part of $R^{15a}$ may not bear a substituent containing or consisting of a carbocyclic or heterocyclic group.

6. A compound according to claim 5, or a salt, N-oxide or tautomer thereof, wherein each $R^{13a}$ is independently selected from chlorine; fluorine; cyano; a 3 to 8 membered non-aromatic carbocyclic or heterocyclic ring containing 1 or two heteroatom ring members selected from O, N and S and being optionally substituted with one or more substituents $R^{14a}$; a five or six membered aryl or heteroaryl group containing 1, 2 or 3 heteroatom ring members selected from O, N and S and being optionally substituted with one or more substituents $R^{14a}$; and a group $R^{a1}$-$R^{b1}$.

7. A compound according to claim 6, or a salt, N-oxide or tautomer thereof, wherein each $R^{13a}$ is independently selected from chlorine, fluorine, $C_{1-4}$ alkyl, $C_{1-4}$ alkoxy, $C_{1-4}$ acylamino, amino, mono-$C_{1-4}$ alkylamino, di-$C_{1-4}$ alkylamino, carbamoyl, $C_{1-4}$ alkylcarbamoyl, di-$C_{1-4}$ alkylcarbamoyl, cyano, $C_{1-4}$ alkoxycarbonyl, morpholinyl, piperidinyl, piperazinyl, homopiperazinyl, N—$C_{1-3}$-alkylpiperazinyl, N—$C_{1-3}$-alkylhomopiperazinyl, phenyl, pyridyl, furanyl, thienyl and pyrazolyl, wherein the $C_{1-4}$ alkyl and $C_{1-4}$ alkoxy substituents are each optionally further substituted with one or more fluorine atoms or by hydroxy or $C_{1-2}$ alkoxy, and wherein the phenyl, pyridyl, furanyl, thienyl and pyrazolyl substituents are each optionally further substituted with one or more halogen, $C_{1-4}$ alkyl or $C_{1-4}$ alkoxy groups.

8. A compound according to claim 1, or a salt, N-oxide or tautomer thereof, wherein $R^1$ is cyano.

9. A compound according to claim 1, or a salt, N-oxide or tautomer thereof, wherein $R^2$ is hydrogen.

10. A compound according to claim 1, or a salt, N-oxide or tautomer thereof, wherein $R^3$ is hydrogen.

11. A compound according to claim 1, or a salt, N-oxide or tautomer thereof, wherein $R^4$ is hydrogen or methoxy.

12. A compound according to claim 1, or a salt, N-oxide or tautomer thereof, wherein $R^5$ is hydrogen or methoxy.

13. A compound according to claim 1, or a salt, N-oxide or tautomer thereof, wherein $R^6$ is hydrogen or chlorine.

14. A compound according to claim 1, or a salt, N-oxide or tautomer thereof, wherein $R^7$ is hydrogen.

15. A compound according to claim 1, or a salt, N-oxide or tautomer thereof, wherein m is 1, n is O and $R^1$ is cyano.

16. A compound according to claim 1 wherein the compound of formula (1) has the formula (2):

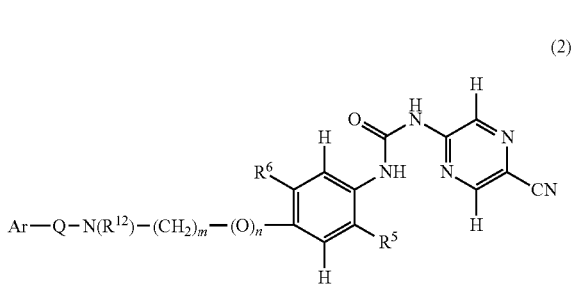

(2)

or a salt, N-oxide or tautomer thereof wherein $R^{12}$ is selected from hydrogen and methyl.

17. A compound according to claim 16 wherein the compound of formula (2) has the formula (3):

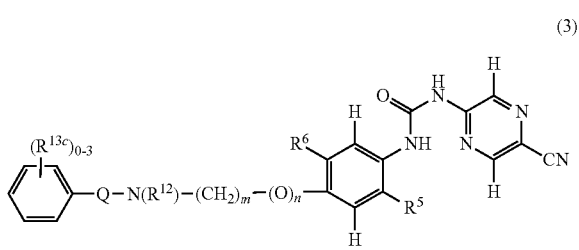

(3)

or a salt, N-oxide or tautomer thereof;
wherein $R^{13c}$ is a group $R^{13}$.

18. A compound according to claim 17 wherein the compound of formula (3) has the formula (4):

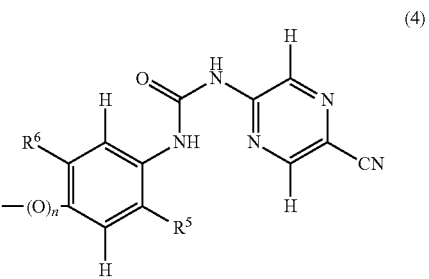

(4)

or a salt, N-oxide or tautomer thereof;
wherein w is 1 or 2; y is 0, 1, 2, 3 or 4; $R^{16}$ is hydrogen or $C_{1-3}$ alkyl; and $R^{17}$ is $C_{1-3}$ alkyl.

19. A compound according to claim 1 which is selected from the compounds:

1-[4-(2-benzylamino-ethyl)-phenyl]-3-(5-cyano-pyrazin-2-yl)-urea;
  1-(5-cyano-pyrazin-2-yl)-3-{4-[2-(4-fluoro-benzylamino)-ethyl]-phenyl}-urea;
  1-(5-cyano-pyrazin-2-yl)-3-{4-[2-(2,4-difluoro-benzylamino)-ethyl]-phenyl}-urea;
  1-{3-chloro-4-[2-(4-fluoro-benzylamino)-ethyl]-phenyl}-3-(5-cyano-pyrazin-2-yl)-urea;
  1-{3-chloro-4-[2-(2,4-difluoro-benzylamino)-ethyl]-phenyl}-3-(5-cyano-pyrazin-2-yl)-urea;
  1-{3-chloro-4-[2-(2,4-difluoro-benzylamino)-ethoxy]-phenyl}-3-(5-cyano-pyrazin-2-yl)-urea;
  1-(3-chloro-4-(2-(4-fluorophenethylamino)ethyl)phenyl)-3-(5-cyanopyrazin-2-yl)-urea;
  1-{3-chloro-4-[2-(4-chloro-benzylamino)-ethyl]-phenyl}-3-(5-cyano-pyrazin-2-yl)-urea;
  1-{3-chloro-4-[2-(3-fluoro-benzylamino)-ethyl]-phenyl}-3-(5-cyano-pyrazin-2-yl)-urea;
  1-{3-chloro-4-[2-(2-chloro-benzylamino)-ethyl]-phenyl}-3-(5-cyano-pyrazin-2-yl)-urea;
  1-(3-chloro-4-{2-[(4-fluoro-benzyl)-methyl-amino]-ethyl}-phenyl)-3-(5-cyano-pyrazin-2-yl)-urea;
  1-{3-chloro-4-[2-(3-methoxy-benzylamino)-ethyl]-phenyl}-3-(5-cyano-pyrazin-2-yl)-urea;
  1-{3-chloro-4-[2-(3-chloro-benzylamino)-ethyl]-phenyl}-3-(5-cyano-pyrazin-2-yl)-urea;
  1-{3-chloro-4-[2-(4-trifluoromethoxy-benzylamino)-ethyl]-phenyl}-3-(5-cyano-pyrazin-2-yl)-urea;
  1-{3-chloro-4-[2-(4-methoxy-benzylamino)-ethyl]-phenyl}-3-(5-cyano-pyrazin-2-yl)-urea;
  1-{3-chloro-4-[2-(2-methoxy-benzylamino)-ethyl]-phenyl}-3-(5-cyano-pyrazin-2-yl)-urea;
  1-{3-chloro-4-[2-(4-trifluoromethyl-benzylamino)-ethyl]-phenyl}-3-(5-cyano-pyrazin-2-yl)-urea;
  1-(3-chloro-4-{2-[(S)-1-(4-fluoro-phenyl)-ethylamino]-ethyl}-phenyl)-3-(5-cyano-pyrazin-2-yl)-urea;
  1-[4-(benzylamino-methyl)-2-methoxy-phenyl]-3-(5-cyano-pyrazin-2-yl)-urea;
  1-{5-chloro-4-[2-(3-fluoro-benzylamino)-ethyl]-2-methoxy-phenyl}-3-(5-cyano-pyrazin-2-yl)-urea;
  1-(5-cyano-pyrazin-2-yl)-3-{4-[2-(4-fluoro-benzylamino)-ethyl]-2-methoxy-phenyl}-urea;
  1-(5-cyano-pyrazin-2-yl)-3-{4-[2-(4-fluoro benzylamino)-ethoxy]-2-methoxy-phenyl}-urea;
  1-{3-chloro-4-[2-(2-fluoro-benzylamino)-ethyl]-phenyl}-3-(5-cyano-pyrazin-2-yl)-urea;
  1-(3-chloro-4-{2-[(R)-1-(4-fluoro-phenyl)-ethylamino]-ethyl}-phenyl)-3-(5-cyano-pyrazin-2-yl)-urea;
  1-{3-chloro-4-[2-(4-morpholin-4-yl-benzylamino)-ethyl]-phenyl}-3-(5-cyano-pyrazin-2-yl)-urea;
  1-{3-chloro-4-[2-(4-fluoro-benzylamino)-ethoxy]-phenyl}-3-(5-cyano-pyrazin-2-yl)-urea;
  1-(3-chloro-4-{2-[2-(2,4-difluoro-phenyl)-ethylamino]-ethyl}-phenyl)-3-(5-cyano-pyrazin-2-yl)-urea;
  1-(3-chloro-4-{2-[(4-fluoro-benzyl)-methyl-amino]-ethyl}-phenyl)-3-(5-cyano-pyrazin-2-yl)-urea;
  1-[4-(benzylamino-methyl)-phenyl]-3-(5-cyano-pyrazin-2-yl)-urea;
  1-(5-cyano-pyrazin-2-yl)-3-{4-[2-(2,4-difluoro-benzylamino)-ethyl]-2-methoxy-phenyl}-urea;
  1-(5-cyano-pyrazin-2-yl)-3-(4-{2-[2-(4-fluoro-phenyl)-ethylamino]-ethyl}-2-methoxy-phenyl)-urea;
  1-[4-(2-benzylamino-ethyl)-2-methoxy-phenyl]-3-(5-methyl-pyrazin-2-yl)-urea;
  1-(5-cyano-pyrazin-2-yl)-3-{4-[2-(2,4-difluoro-benzylamino)-ethoxy]-2-methoxy-phenyl}-urea;
  1-(5-Cyano-pyrazin-2-yl)-3-{3-[2-(4-fluoro-benzylamino)-ethyl]-phenyl}-urea;

1-(3-Chloro-4-{2-[4-(4-methyl-piperazin-1-yl)-benzylamino]-ethyl}-phenyl)-3-(5-cyano-pyrazin-2-yl)-urea;
1-(5-Cyano-pyrazin-2-yl)-3-{4-[2-(4-fluoro-benzylamino)-ethyl]-3-methyl-phenyl}-urea;
1-{5-Chloro-4-[2-(4-fluoro-benzylamino)-ethyl]-2-methoxy-phenyl}-3-(5-cyano-pyrazin-2-yl)-urea;
1-(3-Chloro-4-{2-[3-(4-methyl-piperazin-1-yl)-benzylamino]-ethyl}-phenyl)-3-(5-cyano-pyrazin-2-yl)-urea;
1-{3-Chloro-4-[2-(3-morpholin-4-yl-benzylamino)-ethyl]-phenyl}-3-(5-cyano-pyrazin-2-yl)-urea;
1-{3-Chloro-4-[2-(3,4-difluoro-benzylamino)-ethyl]-phenyl}-3-(5-cyano-pyrazin-2-yl)-urea;
1-{3-Bromo-4-[2-(4-fluoro-benzylamino)-ethyl]-phenyl}-3-(5-cyano-pyrazin-2-yl)-urea;
1-{5-Bromo-4-[2-(4-fluoro-benzylamino)-ethyl]-2-methoxy-phenyl}-3-(5-cyano-pyrazin-2-yl)-urea;
1-(5-Cyano-pyrazin-2-yl)-3-(4-{2-[(R)-1-(4-fluoro-phenyl)-ethylamino]-ethyl}-2-methoxy-phenyl)-urea;
1-(5-Cyano-pyrazin-2-yl)-3-(4-{2-[(S)-1-(4-fluoro-phenyl)-ethylamino]-ethyl}-2-methoxy-phenyl)-urea;
1-{5-Chloro-2-ethoxy-4-[2-(4-fluoro-benzylamino)-ethyl]-phenyl}-3-(5-cyano-pyrazin-2-yl)-urea;
1-{5-Chloro-4-[2-(4-fluoro-benzylamino)-ethyl]-2-isopropoxy-phenyl}-3-(5-cyano-pyrazin-2-yl)-urea;
1-{5-Chloro-4-[2-(4-fluoro-benzylamino)-ethoxy]-2-methoxy-phenyl}-3-(5-cyano-pyrazin-2-yl)-urea;
1-{5-Chloro-2-methoxy-4-[2-(3-methoxy-benzylamino)-ethyl]-phenyl}-3-(5-cyano-pyrazin-2-yl)-urea;
1-{5-Chloro-2-methoxy-4-[2-(4-methoxy-benzylamino)-ethyl]-phenyl}-3-(5-cyano-pyrazin-2-yl)-urea;
1-(5-Chloro-2-methoxy-4-{2-[4-(4-methyl-piperazin-1-yl)-benzylamino]-ethyl}-phenyl)-3-(5-cyano-pyrazin-2-yl)-urea;
1-(5-Cyano-pyrazin-2-yl)-3-(2-methoxy-4-{2-[4-(4-methyl-piperazin-1-yl)-benzylamino]-ethyl}-phenyl)-urea;
1-(5-Chloro-2-methoxy-4-{2-[(S)-1-(4-piperazin-1-yl-phenyl)-ethylamino]-ethyl}-phenyl)-3-(5-cyano-pyrazin-2-yl)-urea;
1-(5-Chloro-2-methoxy-4-{2-[(S)-1-(4-methoxy-phenyl)-ethylamino]-ethyl}-phenyl)-3-(5-cyano-pyrazin-2-yl)-urea;
1-(4-{2-[(Benzo[1,3]-dioxol-5-ylmethyl)-amino]-ethyl}-5-chloro-2-methoxy-phenyl)-3-(5-cyano-pyrazin-2-yl)-urea;
1-{5-Chloro-2-methoxy-4-[2-(2-methoxy-benzylamino)-ethyl]-phenyl}-3-(5-cyano-pyrazin-2-yl)-urea;
1-[4-(Benzylamino-methyl)-5-chloro-2-methoxy-phenyl]-3-(5-cyano-pyrazin-2-yl)-urea;
1-(5-Cyano-pyrazin-2-yl)-3-{4-[(4-fluoro-benzylamino)-methyl]-2-methoxy-phenyl}-urea;
1-(5-Cyano-pyrazin-2-yl)-3-{4-[(3-fluoro-benzylamino)-methyl]-2-methoxy-phenyl}-urea;
1-(5-Cyano-pyrazin-2-yl)-3-{4-[(2-fluoro-benzylamino)-methyl]-2-methoxy-phenyl}-urea;
1-(5-Cyano-pyrazin-2-yl)-3-{2-methoxy-4-[(4-methoxy-benzylamino)-methyl]-phenyl}-urea;
1-(5-Cyano-pyrazin-2-yl)-3-{2-methoxy-4-[(3-methoxy-benzylamino)-methyl]-phenyl}-urea;
1-(5-Cyano-pyrazin-2-yl)-3-{2-methoxy-4-[(2-methoxy-benzylamino)-methyl]-phenyl}-urea;
1-{5-Chloro-4-[(4-fluoro-benzylamino)-methyl]-2-methoxy-phenyl}-3-(5-cyano-pyrazin-2-yl)-urea;
1-{5-Chloro-2-methoxy-4-[2-(4-piperazin-1-yl-benzylamino)-ethyl]-phenyl}-3-(5-cyano-pyrazin-2-yl)-urea and;
1-(5-Chloro-2-methoxy-4-{2-[(S)-1-(3-methoxy-phenyl)-ethylamino]-ethyl}-phenyl)-3-(5-cyano-pyrazin-2-yl)-urea;
and salts and tautomers thereof.

20. A pharmaceutical composition comprising a compound as defined in claim 1, or a salt, N-oxide or tautomer thereof, and a pharmaceutically acceptable carrier.

21. A compound according to claim 16, or a salt or tautomer thereof, wherein $R^5$ is hydrogen or methoxy; $R^6$ is hydrogen or chlorine; $R^{12}$ is hydrogen; n is 0; m is 2; Q is a group —CHMe—; and Ar is a phenyl group which is unsubstituted or bears one or two substituents $R^{13a}$ independently selected from fluorine and methoxy.

22. A compound according to claim 21, or a salt or tautomer thereof, wherein $R^5$ is methoxy; $R^6$ is hydrogen; and Ar bears a single fluorine atom substituent.

* * * * *